(12) United States Patent
Srinivasan et al.

(10) Patent No.: US 11,884,984 B2
(45) Date of Patent: Jan. 30, 2024

(54) KITS AND METHODS FOR ASSESSING A CONDITION OR A RISK OF DEVELOPING A CONDITION, AND RELATED METHODS OF TREATMENT

(71) Applicant: FRED HUTCHINSON CANCER RESEARCH CENTER, Seattle, WA (US)

(72) Inventors: Sujatha Srinivasan, Redmond, WA (US); David N. Fredricks, Seattle, WA (US)

(73) Assignee: FRED HUTCHINSON CANCER RESEARCH CENTER, Seattle, WA (US)

(*) Notice: Subject to any disclaimer, the term of this patent is extended or adjusted under 35 U.S.C. 154(b) by 139 days.

(21) Appl. No.: 16/927,897

(22) Filed: Jul. 13, 2020

(65) Prior Publication Data
US 2021/0010067 A1 Jan. 14, 2021

Related U.S. Application Data

(60) Provisional application No. 62/873,817, filed on Jul. 12, 2019.

(51) Int. Cl.
| | | |
|---|---|---|
| C12Q 1/689 | (2018.01) |
| A61K 31/4164 | (2006.01) |
| A61K 31/546 | (2006.01) |
| A61K 31/65 | (2006.01) |
| A61K 31/7052 | (2006.01) |
| A61K 31/496 | (2006.01) |
| C12Q 1/70 | (2006.01) |
| C12Q 1/6893 | (2018.01) |
| A61K 31/5383 | (2006.01) |

(52) U.S. Cl.
CPC .......... *C12Q 1/689* (2013.01); *A61K 31/4164* (2013.01); *A61K 31/496* (2013.01); *A61K 31/5383* (2013.01); *A61K 31/546* (2013.01); *A61K 31/65* (2013.01); *A61K 31/7052* (2013.01); *C12Q 1/6893* (2013.01); *C12Q 1/701* (2013.01); *C12Q 1/705* (2013.01); *C12Q 2600/112* (2013.01); *C12Q 2600/16* (2013.01)

(58) Field of Classification Search
CPC ...... C12Q 1/689; C12Q 1/6893; C12Q 1/701; C12Q 1/705; C12Q 2600/112; C12Q 2600/16; A61K 31/416; A61K 31/496; A61K 31/5383; A61K 31/546; A61K 31/65; A61K 31/7052
USPC ....................................................... 514/29
See application file for complete search history.

(56) References Cited

U.S. PATENT DOCUMENTS 7,625,704 B2 12/2009 Fredricks et al.

FOREIGN PATENT DOCUMENTS

WO 2016168284 A1 10/2016

OTHER PUBLICATIONS

Kondo et al. GyrA and/or ParC alterations of Haemophilus influenzae strains isolated from the urethra of men with acute urethritis. J Infect Chemother 24 (2018) 232-235, Available online Nov. 11, 2017. (Year: 2018).*
Frolund et al. Urethritis-associated Pathogens in Urine from Men with Nongonococcal Urethritis: A Case-control Study. Acta Derm Venereol 2016; 96: 689-695, and Appendix S1. (Year: 2016).*
Srinivasan et al. The Urethral Microbiota in Nongonococcal Urethritis. Sex Transm Infect 2017;93(Suppl 2):A1- A272, p. A14, Abstract #O06.6. (Year: 2017).*
"16S Metagenomic Sequencing Library Preparation: Preparing 16S Ribosomal RNA Gene Amplicons for the Illumina MiSeq System," URL=https://support.illumina.com/documents/documentation/chemistry_documentation/16s/16s-metagenomic-library-prep-guide-15044223-b.pdf, download date Jul. 17, 2020, 28 pages.
Abdool Karim et al., "Safety and effectiveness of BufferGel and 0.5% PRO2000 gel for the prevention of HIV infection in women," *AIDS* 25(7):957-966, 2011.
Abdool Karim et al., "The genital tract and rectal microbiomes: their role in HIV susceptibility and prevention in women," *Journal of the International AIDS Society* 22:e25300, 2019. (12 pages).
Achilles et al., "Impact of contraceptive initiation on vaginal microbiota," *Am. J. Obstet. Gynecol.* 218(6):622.e1-622.e10, 2018.
Achwoka et al., "Uptake and correlates of contraception among postpartum women in Kenya: results from a national cross-sectional survey," *Contraception.* 97(3):227-235, Mar. 2018.
Aghaizu et al., "Frequency and risk factors for incident and redetected *Chlamydia trachomatis* infection in sexually active, young, multi-ethnic women: a community based cohort study," *Sex. Transm. Infect.* 90(7):524-528, 2014.
Altschul et al., "Gapped BLAST and PSI-BLAST: a new generation of protein database search programs," *Nucleic Acids Res.* 25:3389-3402, 1997.

(Continued)

*Primary Examiner* — Yih-Horng Shiao
(74) *Attorney, Agent, or Firm* — Seed IP Law Group LLP

(57) ABSTRACT

Provided herein are kits and methods for detecting, monitoring, and classifying a nongonococcal urethritis (NGU) infection in a male subject based on a genitourinary microbiome of a subject, as well as related methods of treating.

Also provided are kits and methods for classifying a risk of human immunodeficiency virus (HIV) infection in a subject based on a genitourinary microbiome of a subject, as well as related methods of preventing infection.

16 Claims, 19 Drawing Sheets
(17 of 19 Drawing Sheet(s) Filed in Color)
Specification includes a Sequence Listing.

(56) References Cited

OTHER PUBLICATIONS

Anagrius et al., "*Mycoplasma genitalium*: prevalence, clinical significance, and transmission," *Sex. Transm. Infect.* 81(6):458-462, 2005.
Anahtar et al., "Cervicovaginal bacteria are a major modulator of host inflammatory responses in the female genital tract," *Immunity* 42(5): 965-976, May 19, 2015.
Anton et al., "Evidence of a $TH_1$-shift of local vaginal inflammatory response during bacterial vaginosis," *Infection* 36(2):147-152, 2008.
Arnold et al., "Increased levels of inflammatory cytokines in the female reproductive tract are associated with altered expression of proteases, mucosal barrier proteins, and an influx of HIV-susceptible target cells," *Mucosal Immunology* 9(1):194-205, Jan. 2016.
Atashili et al., "Bacterial vaginosis and HIV acquisition: a meta-analysis of published studies," *AIDS* 22(12):1493-501, Jul. 31, 2008.
Austin et al., "*Mageeibacillus indolicus* gen. nov., sp. nov.: A Novel Bacterium Isolated from the Female Genital Tract," *Anaerobe* 32:37-42, Apr. 2015.
Austin et al., "Microbiologic Response to Treatment of Bacterial Vaginosis with Topical Clindamycin or Metronidazole," *J. Clin. Microbiol.* 43(9):4492-4497, Sep. 2005.
Balkus et al., "A multi-site comparative study to understand sources of variability in studies of the vaginal microbiota," *Sex. Transm. Infect.* 95(Suppl. 1):A262-A263, 2019.
Balkus et al., "Bacterial vaginosis and the risk of *Trichomonas vaginalis* acquisition among HIV-1 negative women," *Sex. Transm. Dis.* 41(2): 123-128, Feb. 2014.
Balkus et al., "Establishing and Sustaining a Healthy Vaginal Environment: Analysis of Data From a Randomized Trial of Periodic Presumptive Treatment for Vaginal Infections," *J. Infect. Dis.* 204(2):323-326, Jul. 15, 2011.
Balkus et al., "Impact of Periodic Presumptive Treatment for Bacterial Vaginosis on the Vaginal Microbiome among Women Participating in the Preventing Vaginal Infections Trial," *J. Infect. Dis.* 215:723-731, Mar. 1, 2017.
Balkus et al., "Lessons from Suppressive Therapy and Periodic Presumptive Treatment for Bacterial Vaginosis," *Curr Infect Dis Rep* 21(34):Aug. 31, 2019. (9 pages).
Balkus et al., "*Mycoplasma genitalium* infection in Kenyan and US women," *Sex Transm Dis* 45(8):514-521, Aug. 2018.
Balkus et al., "The post-trial effect of oral periodic presumptive treatment for vaginal infections on the incidence of bacterial vaginosis and *Lactobacillus* colonization," *Sex. Transm. Dis.* 39(5):361-365, May 2012.
Barbee et al., "An estimate of the proportion of symptomatic gonococcal, chlamydial and non-gonococcal non-chlamydial urethritis attributable to oral sex among men who have sex with men: a case-control study," *Sex. Transm. Infect.* 92(2): 155-160, 2016.
Bauer et al., "Antibiotic susceptibility testing by a standardized single disk method," *American Journal of Clinical Pathology* 45:493-496, 1966.
Bayigga et al., "Diversity of vaginal microbiota in sub-Saharan Africa and its effects on HIV transmission and prevention," *Am. J. Obstet. Gynecol.* 220(2): 155-166, Feb. 2019.
Begaud et al., "Reduced CD4 T cell activation and in vitro susceptibility to HIV-1 infection in exposed uninfected Central Africans," *Retrovirology* 3(35):1-9, Jun. 22, 2006.
Beigi et al., "Antimicrobial resistance associated with the treatment of bacterial vaginosis," *Am J Obstet Gynecol.* 191(4): 1124-1129, 2004.
Benjamini et al., "Controlling the False Discovery Rate: a Practical and Powerful Approach to Multiple Testing," *J. Royal Statistical Soc.* 57(1):289-300, 1995.
Berard et al., "Understanding mucosal and microbial functionality of the female reproductive tract by metaproteomics: Implications for HIV transmission," *Am J Reprod Immunol* 80(2):e12977, 2018. (11 pages).

Blaskewicz et al., "Structure and Function of Intercellular Junctions in Human Cervical and Vaginal Mucosal Epithelia," *Biology of Reproduction* 85(1):97-104, 2011.
Borgdorff et al., "Cervicovaginal microbiome dysbiosis is associated with proteome changes related to alterations of the cervicovaginal mucosal barrier," *Mucosal Immunology* 9(3):621-633, May 2016.
Borgdorff et al., "The Impact of Hormonal Contraception and Pregnancy on Sexually Transmitted Infections and on Cervicovaginal Microbiota in African Sex Workers," *Sex. Transm. Dis.* 42(3):143-152, Mar. 2015.
Boshier et al., "Complementing 16S rRNA gene amplicon sequencing with estimates of total bacterial load to infer absolute species concentrations in the vaginal microbiome," bioRxiv preprint, doi: 10.1101/598771, 2019. (31 pages).
Bowie et al., "Etiology of Nongonococcal Urethritis: Evidence for *Chlamydia trachomatis* and *Ureaplasma urealyticum*," *J. Clin. Invest.* 59(5):735-742, May 1977.
Bradshaw et al., "Etiologies of Nongonococcal Urethritis: Bacteria, Viruses, and the Association with Orogential Exposure," *J. Infect. Dis.* 193:336-345, Feb. 1, 2006.
Bretelle et al., "*High Atopobium vaginae and Gardnerella vaginalis* Vaginal Loads Are Associated With Preterm Birth," *Clin Infect Dis.* 60(6):860-867, Mar. 15, 2015.
Bro, "Metronidazole Pessaries Compared with Placebo in the Treatment of Bacterial Vaginosis," Scand. J. Prim. Health Care 8:219-223, 1990.
Brotman et al., "Bacterial Vaginosis Assessed by Gram Stain and Diminished Colonization Resistance to Incident Gonococcal, Chlamydial, and Trichomonal Genital Infection," *J. Infect. Dis.* 202(12):1907-1915, Dec. 15, 2010.
Brotman et al., "Interplay Between the Temporal Dynamics of the Vaginal Microbiota and Human Papillomavirus Detection," *J. Infect. Dis.* 210:1723-1733, Dec. 1, 2014.
Buck et al., "Design Strategies and Performance of Custom DNA Sequencing Primers," *BioTechniques* 27:528-536, Sep. 1999.
Callahan et al., "DADA2: High-resolution sample inference from Illumina amplicon data," *Nat. Methods* 13(7):581-583, Jul. 2016. (7 pages).
Camara et al., "Low-Level CD4+ T Cell Activation in HIV-Exposed Seronegative Subjects: Influence of Gender and Condom Use," *J. Infect. Dis.* 201(6):835-842, Mar. 15, 2010.
Card et al., "Decreased Immune Activation in Resistance to HIV-1 Infection is Associated with an Elevated Frequency of CD4+CD25+FOXP3+ Regulatory T Cells," *J. Infect. Dis.* 199:1318-1322, May 1, 2009.
Cauci et al., "Among pregnant women with bacterial vaginosis, the hydrolytic enzymes sialidase and prolidase are positively associated with interleukin-1β," *Am. J. Obstet. Gynecol.*: 132.e1-132e.7, Jan. 2008.
Cauci et al., "Interrelationships of interleukin-8 with interleukin-1β and neutrophils in vaginal fluid of healthy and bacterial vaginosis positive women," *Mol. Hum. Reprod.* 9(1):53-58, 2003.
Chambers et al., "Cross-sectional study of urethral exposures at last sexual episode associated with non-gonococcal urethritis among STD clinic patients," *Sex. Transm. Infect.* 95(3):212-218, May 2019.
Chambers et al., "Primary Syphilis in the Male Urethra: A Case Report," *Clinical Infectious Diseases* 68(7): 1231-1234, Apr. 1, 2019.
Chen et al., "A composite likelihood approach to the analysis of longitudinal clonal data on multitype cellular systems under an age-dependent branching process," *Biostatistics* 12(1):173-191, 2011.
Chen et al., "On classes of equivalence and identifiability of age-dependent branching processes," *Adv Appl Probab.* 46(3):704-718, Sep. 2014.
Cherpes et al., "Association between Acquisition of Herpes Simplex Virus Type 2 in Women and Bacterial Vaginosis," *Clin. Infect. Dis.* 37(3):319-325, Aug. 1, 2003.
Chohan et al., "A Prospective Study of Risk Factors for Herpes Simplex Virus Type 2 Acquisition among High-Risk HIV-1 Seronegative Kenyan Women," *Sex. Transm. Infect.* 85(7):489, Dec. 2009. (9 pages).

(56) References Cited

OTHER PUBLICATIONS

Cohen et al., "Bacterial vaginosis and HIV seroprevalence among female commercial sex workers in Chiang Mai, Thailand," *AIDS* 9(9):1093-1097, 1995.
Corey et al., "Differentiation of herpes simplex virus types 1 and 2 in clinical samples by a real-time taqman PCR assay," *J Med Virol* 76(3): 350-5, 2005.
Cu-Uvin et al., "Prevalence of Lower Genital Tract Infections Among Human Immunodefiniciency Virus (HIV)-Seropositive and High-Risk HIV-Seronegative Women," *Clin. Infect. Dis.* 29(5):1145-1150, 1999.
Da Costa et al., "Regulatory T cells limit unconventional memory to preserve the capacity to mount protective CD8 memory responses to pathogens," *Proc Natl Acad Sci USA* 116(20):9969-9979, 2019.
Dareng et al., "Prevalent high-risk HPV infection and vaginal microbiota in Nigerian women," *Epidemiol. Infect.* 144:123-137, 2016.
Davé et al., "Progressive differentiation of memory CD8 T cells in the cervicovaginal tissue," bioRxiv 769711, 2019.
Deguchi et al. "Antimicrobial susceptibility of Haemophilus influenzae strains isolated from the urethra of men with acute urethritis and/or epididymitis," *J Infect Chemother* 23(11): 804-7, 2017.
Deguchi et al., "Assocation of *Ureaplasma urealyticum* (*Biovar* 2) With Nongonococcal Urethritis," *Sex. Trans. Dis.* 31(3):192-195, 2004.
Demba et al., "Bacterial vaginosis, vaginal flora patterns and vaginal hygiene practices in patients presenting with vaginal discharge syndrome in The Gambia, West Africa," *BMC Infect Dis.* 5:1-12, 2005.
Dev et al., "Acceptability, feasibility and utility of a Mobile health family planning decision aid for postpartum women in Kenya," *Reprod Health* 16(1):97, 2019.
Deza et al., "Isolation of Haemophilus influenzae and Haemophilus parainfluenzae in urethral exudates from men with acute urethritis: a descriptive study of 52 cases," *Sex Transm Infect* 92(1): 29-31, 2015.
Dizzell et al., "Protective Effect of Probiotic Bacteria and Estrogen in Preventing HIV-1-Mediated Impairment of Epithelial Barrier Integrity in Female Genital Tract," *Cells* 8(10):1-18, 2019.
Doerflinger et al., "Bacteria in the Vaginal Microbiome Alter the Innate Immune Response and Barrier Properties of the Human Vaginal Epithelia in a Species-Specific Manner," *JID* 4(209):1989-1999, 2014.
Dupont et al., "Hormonal influence on HIV-1 transmission in the female genital tract: New insights from systems biology," *Am J Reprod Immunol.* 80(2):e13019, 2018.
Eastment et al., "Vaginal Microbiota and Susceptibility to HIV," *AIDS* 32(6):687-698, 2018.
Evidence for Contraceptive O, Consortium, "HIV incidence among women using intramuscular depot medroxyprogesterone acetate, a copper intrauterine device, or a levonorgestrel implant for contraception: a randomised, multicentre, open-label trial," Lancet 394:303-313, 2019.
Eyerich et al., "Defining Th-cell subsets in a classical and tissue-specific manner: Examples from the skin," *Eur. J. Immunol.* 44:3475-3483, 2014.
Farley et al., "Invasive *Haemophilus influenzae* Disease in Adults: A prospective, population-based surveillance" *Ann Intern Med* 116(10):806-812, 1992.
Ferris et al., "Treatment of Bacterial Vaginosis: A Comparison of Oral Metronidazole, Metronidazole Vaginal Gel, and Clindamycin Vaginal Cream," *J. Fam. Pract.* 41(5):443-449, 1995.
Fonck et al., "A randomized, placebo-controlled trial of monthly azithromycin prophylaxis to prevent sexually transmitted infections and HIV-1 in Kenyan sex workers: study design and baseline findings," *Int J STD AIDS* 11(12):804-811, 2000.
Fonck et al., "Pattern of Sexually Transmitted Diseases and Risk Factors Among Women Attending an STD Referral Clinic in Nairobi, Kenya" *Sex. Transm. Dis.* 27(7):417-423, 2000.

Fonck et al., "Sexually transmitted infections and vaginal douching in a population of female sex workers in Nairobi, Kenya," *Sex. Transm. Infect.* 77:271-275, 2001.
Francis et al., "Epidemiology of Curable Sexually Transmitted Infections among Women at Increased Risk of HIV in Northwestern Tanzania: Inadequacy of Syndromic Management," *PLoS ONE* 9(7):e101221, 2014.
Fredricks et al., "Changes in Vaginal Bacterial Concentrations with Intravaginal Metronidazole Therapy for Bacterial Vaginosis as Assessed by Quantitative PCR," *J. Clin. Microbio.* 47(3):721-726, 2009.
Fredricks et al., "Molecular identification of bacteria associated with bacterial vaginosis," *N Engl J Med.* 353(18):1899-911, 2005.
Fredricks et al., "Targeted PCR for the detection of vaginal bacteria associated with bacterial vaginosis," *J Clin Microbiol.* 45(10):3270-3276, 2007.
Fredricks, "Metabolite Biomarkers For Bacterial Vaginosis," Fred Hutch, Business Development and Industry Relations, Jun. 5, 2017. (2 pages).
Fredricks, "Metabolite Biomarkers For Bacterial Vaginosis: Technology Overview," Non-confidential Summary, Fred Hutchinson Cancer Research Center, Jun. 5, 2017, accessed Oct. 19, 2020, from https://www.fredhutch.org/content/dam/public/BDIR-NCS-PDF/15-024%20Fredricks_Bacterial%20vaginosis%20biomarkers.pdf?_ga=2.136198321.1012994156.1603136318-1682022668.1603136318, 1 page.
Fritz et al., "Required Sample Size to Detect the Mediated Effect," *Psychol. Sci.* 18(3):233-239, 2007.
Frolund et al., "The bacterial microbiota in first-void urine from men with and without idiopathic urethritis," *PLoS One* 13(7):e0201380, 2018.
Frolund et al., "Urethritis-associated Pathogens in Urine from Men with Non-gonococcal Urethritis: A Case-Control Study," *Acta. Derm. Venereol.* 96(5):689-694, 2016.
Gallo et al., "Risk Factors for Incident Herpes Simplex Type 2 Vrius Infection Among Women Attending a Sexually Transmitted Disease Clinic," *Sexually Transmitted Diseases* 35(7):679-685, 2008.
Golob et al., "Stool microbiota at neutrophil recovery is predictive for severe acute graft versus host disease after hematopoietic cell transplantation," *Clin Infect Dis.* 65(12):1984-1991, 2017.
Gorgos et al., "Relationship of specific bacteria in the cervical and vaginal microbiotas with cervicitis," *Sex Transm Dis.* 42(9):475-481, 2015.
Gosmann et al., "*Lactobacillus*-Deficient Cervicovaginal Bacterial Communities are Associated with Increased HIV Acquisition in Young South African Women," *Immunity* 46(1):29-37, 2017.
Gottlieb et al., "Incidence of Herpes Simplex Virus Type 2 Infection in 5 Sexually Transmitted Disease (STD) Clinics and the Effect of HIV/STD Risk-Reduction Counseling," *JID* 190:1059-1067, 2004.
Goyette et al., "Association between menopause and unprotected sex in high-risk HIV-positive women in Mombasa, Kenya," *J. Acquir. Immune Defic. Syndr.* 74(5):488-492, 2017.
Graham et al., "A mouse model of chronic West Nile virus disease," *PLoS Pathog* 12:e1005996, 2016.
Graham et al., "Antiretroviral adherence and development of drug resistance are the strongest predictors of genital HIV-1 shedding among women initiating treatment," *J Infect Dis.* 202:1538-42, 2010.
Graham et al., "Antiretroviral treatment interruptions predict female genital shedding of genotypically resistant HIV-1 RNA," *J Acquir Immune Defic Syndr.* 60(5):511-8, 2012.
Graham et al., "Extensive homeostatic T cell phenotypic variation within the Collaborative Cross," *Cell Reports* 21(8):2313-2325, 2017.
Graham et al., "Genetic diversity in the collaborative cross model recapitulates human West Nile virus disease outcomes," *Mbio* 6:e00493-15, 2015.
Graham et al., "Immune correlates of protection from West Nile virus neuroinvasion and disease," *J Infect Dis* 219(7):1162-1171, 2019.
Graham et al., Initiation of antiretroviral therapy leads to a rapid decline in cervical and vaginal HIV-1 shedding. AIDS 2007;21: 501-507. PMID: 17301569.

(56) References Cited

OTHER PUBLICATIONS

Graham et al., "Regulatory T cells shape the resident memory T cell response to virus infection in the tissues," *J Immunol* 192:683-690, 2014.
Greaves et al., "Clindamycin Versus Metronidazole in the Treatment of Bacterial Vaginosis," *Obstet. Gynecol.* 72(5):799-802, 1988.
Gupta et al., "Inverse Association of $H_2O_2$-Producing Lactobacilli and Vaginal *Escherichia coli* Colonization in Women with Recurrent Urinary Tract Infections," *J. Infect. D.* 178:446-450, 1998.
Hanin et al., "A comprehensive stochastic model of irradiated cell population in cell culture," *Journal of Theoretical Biology* 239:401-416, 2006.
Hanson et al., "Metronidazole for bacterial vaginosis. A comparison of vaginal gel vs. oral therapy," *J . Reprod. Med.* 45(11):889-96, 2000.
Harrington et al., "Engaging men in an mHealth approach to support postpartum family planning among couples in Kenya: a qualitative study," *Reprod Health.* 16(1): 17, 2019.
Hasselrot et al., "Feasibility and safety of cervical biopsy sampling for mucosal immune studies in female sex workers from Nairobi, Kenya," *PLoS One* 7(10):e47570, 2012.
Hayes et al., "In vitro antibiotic susceptibility testing of clinical isolates of *Mycoplasma penetrans* from patients with AIDS," *Antimicrobial Agents and Chemotherapy* 39(6):1386-1387, 1995.
Hedges et al., "Local and systemic cytokine levels in relation to changes in vaginal flora," *J. Infect. Dis.* 193(4):556-562, Feb. 15, 2006.
Heffron et al., "Implementation of a comprehensive safer conception intervention for HIV- serodiscordant couples in Kenya: uptake, use, and effectiveness," *Journal of the International AIDS Society (JIAS)* 22(4):e25261, 2019.
Helfgott et al., Vaginal infections in human immunodeficiency virus-infected women. *Am. J. Obstet. Gynecol.* 183(2):347-55, Aug. 2000.
Helms et al., "Interpersonal Mechanisms Contributing to the Association Between HIV-Related Internalized Stigma and Medication Adherence," *AIDS Behav.* 21(1):238-247, Jan. 2017. (19 pages).
Hemalatha et al., "Cervicovaginal inflammatory cytokines and sphingomyelinase in women with and without bacterial vaginosis," *The American journal of the medical sciences* 344(1):35-9, 2012.
Henn et al., "Modulation of Single-Cell IgG Secretion Frequency and Rates in Human Memory B Cells by CpG DNA, CD40L, IL-21, and Cell Division," *Journal of Immunology* 183:3177-3187, 2009.
Hilber et al., "Intravaginal practices, vaginal infections and HIV acquisition: systematic review and meta-analysis," *PLoS One.* 5(2):e9119, 2010.
Hilchey et al., "Rituximab immunotherapy results in the induction of a lymphoma idiotype- specific T-cell response in patients with follicular lymphoma; support for a "vaccinal effect" of rituximab," *Blood* 113:3809-3812, 2009.
Hillier et al., "Efficacy of intravaginal 0.75% metronidazole gel for the treatment of bacterial vaginosis," *Obstet. Gynecol.* 81(6):963-967, 1993.
Hillier et al., "Secnidazole Treatment of Bacterial Vaginosis: A Randomized Controlled Trial," *Obstet. Gynecol.* 130(2):379-86, 2017.
Hladik et al., "Setting the stage: HIV host invasion," *Nature Reviews Immunology* 8(6):447-57, 2008.
Hocdé et al., "Cell adhesion molecule distribution relative to neutrophil surface topography assessed by TIRFM," *Biophysical Journal* 97:379-387, 2009.
Hocdé et al., "Molecular accessibility in relation to cell surface topography and compression against a flat substrate," *Biophysical Journal* 97:369-378, 2009.
Hochmeister et al., "Evaluation of prostatespecific antigen (PSA) membrane test assays for the forensic identification of seminal fluid," *Journal of Forensic Sciences* 44(5):1057-60, 1999.
Hoffman, "barcodecop," Nov. 14, 2019, URL=https://github.com/nhoffman/barcodecop, download date Jul. 17, 2020, 4 pages.
Hoffman, "Yet Another 16S rRNA database," Nov. 18, 2019, URL=https://github.com/nhoffman/ya16sdb, download date Jul. 17, 2020, 3 pages.
Hooton et al., "Association between bacterial vaginosis and acute cystitis in women using diaphragms," *Arch. Intern. Med.* 149(9):1932-1936, 1989.
Hooton et al., "Effects of recent sexual activity and use of a diaphragm on the vaginal microflora," *Clin. Infect. Dis.* 19(2):274-278, 1994.
Hughes et al., "Analysis of a randomized trial to prevent vertical transmission of HIV-1" JASA 95(452):1032-43, 2000.
Hyman et al., "Diversity of the vaginal microbiome correlates with preterm birth," *Reproductive Sciences* 21(1):32-40, 2014.
Hyrien et al., "A Mixture model with dependent observations for the analysis of CSFE-labeling experiments," *Journal of the American Statistical Association* 103(481):222-239, 2008.
Hyrien et al., "A stochastic model to analyze clonal data on multi type cell populations," *Biometrics* 61:199-207, 2005.
Hyrien et al., "A test of homogeneity for age-dependent branching processes with immigration," *Electronic Journal of Statistics* 9:898-925, 2015.
Hyrien et al., "An age-dependent branching process model for the analysis of CFSE-labeling experiments," *Biology Direct, Mathematical Biology Section* 5:41, 2010.
Hyrien et al., "Fast nonparametric density-based clustering of large data sets using a stochastic approximation mean-shift algorithm," *Journal of Computational & Graphical Statistics* 25:899-916, 2016.
Hyrien et al., "Mathematical and experimental approaches to identify and predict the effects of chemotherapy on neuroglial precursors," American Association for *Cancer Research* 70(24): 10051-10059, 2010.
Hyrien et al., "Saddlepoint approximations to the moments of agedependent branching processes, with applications," *Biometrics* 66:567-577, 2010.
Hyrien et al., "Stochastic modeling of stress erythropoiesis using a two-type age-dependent branching process with immigration," *Journal of Mathematical Biology* 70(7):1485-1521, 2015.
Hyrien et al., "Subcritical Sevastyanov branching processes with nonhomogeneous Poisson immigration," *Journal of Applied Probability* 54:2, 569-587, 2017.
Iser et al., "Symptoms of non-gonococcal urethritis in heterosexual men: a case control study," *Sex Transm .Infect.* 81(1): 163-165, 2005.
Ito et al., "*Haemophilus influenzae* isolated from men with acute urethritis: its pathogenic roles, responses to antimicrobial chemotherapies, and antimicrobial susceptibilities," *Sex Transm. Dis.* 44(4): 205-210, 2017.
Ito et al., "Prevalence of genital mycoplasmas and ureaplasmas in men younger than 40 years-of-age with acute epididymitis," *Int. J. Urol.* 19(3): 234-238, 2012.
Jarrett et al., "Specific Vaginal Bacteria Are Associated With an Increased Risk of *Trichomonas vaginalis* Acquisition in Women," *J. Infect. Dis.* 220(9):1503-1510, 2019.
Jennes et al., "Suppressed cellular alloimmune responses in HIV-exposed seronegative female sex workers," *Clinical and Experimental Immunology* 143(3):435-44, 2006.
Jian-Ru et al., "Mycoplasmas in the urine of HIV-1 infected men," *Epidemiol. Infect.* 140(6):1141-6, 2011.
Joag et al., "Impact of Standard Bacterial Vaginosis Treatment on the Genital Microbiota, Immune Milieu, and Ex Vivo Human Immunodeficiency Virus Susceptibility" *Clin. Infect. Dis.* 68(10):675-683, 2019.
Jordan et al., "Aetiology and prevalence of mixed-infections and mono-infections in non-gonococcal urethritis in men: a case-control study," *Sex Transm. Infect.* 96:306-311, 2020.
Kapiga et al., "HIV-1 epidemic among female bar and hotel workers in northern Tanzania: risk factors and opportunities for prevention," *J. Acquir. Immune. Defic. Syndr.* 29(4):409- 17, 2002.
Kaur et al., "Crosstalk Between Female Gonadal Hormones and Vaginal Microbiota Across Various Phases of Women's Gynecological Lifecycle," *Front. Microbiol.* 11:551, 2020.

(56) References Cited

OTHER PUBLICATIONS

Kaushic, "HIV-1 infection in the female reproductive tract: role of interactions between HIV-1 and genital epithelial cells," *Am. J. Reprod. Immunol.* 65(3):253-60, 2011.
Kaushic et al., "HIV infection in the female genital tract: discrete influence of the local mucosal microenvironment," *Am. J. Reprod. Immunol.* 63(6):566-75, 2010.
Keller et al., "Impact of Herpes Simplex Virus Type 2 and Human Immunodeficiency Virus Dual Infection on Female Genital Tract Mucosal Immunity and the Vaginal Microbiome," *J. Infect. Dis.* 220(5):852-861, 2019.
Kemp et al., "Implementation of eHealth interventions across the HIV care cascade: A review of recent research," *Current HIV/AIDS Reports.* 15(6):403-413, 2018.
Kenya Ministry of Health, "Kenya National Guidelines for Prevention, Management and Control of Sexually Transmitted Infections," National AIDS and STI Control Programme, Kenyatta National Hospital (KNH Grounds), Nairobi, Kenya, 2018. (98 pages).
Kenyon et al., "The global epidemiology of bacterial vaginosis: a systematic review," *Am. J. Obstet. Gynecol.* 209(6):505-23, 2013.
Khot et al., "Development and optimization of quantitative PCR for the diagnosis of invasive aspergillosis with bronchoalveolar lavage fluid," *BMC Infect. Dis.* 8:73, 2008.
Kinuthia et al., "Cofactors for HIV-1 incidence during pregnancy and postpartum Period," *Curr HIV Res.* 8(7): 510-514, 2010.
Kinuthia et al., "HIV acquisition during pregnancy and postpartum is associated with genital infections and partnership characteristics," *AIDS* 29(15):2025-33, 2015.
Kinuthia et al., "Pre-exposure prophylaxis uptake and early continuation among pregnant and postpartum women within maternal and child health clinics in Kenya: results from an implementation programme," *Lancet HIV* 7(1):e38-e48, 2019.
Kinuthia et al., "Uptake of prevention of mother to child transmission interventions in Kenya: health systems are more influential than stigma," *J Intl AIDS Soc.* 14(61):1-9, 2011.
Kleinschmidt et al., "Injectable progestin contraceptive use and risk of HIV infection in a South African family planning cohort," *Contraception* 75(6):461-7, 2007.
Kohler et al., "Community-based evaluation of PMTCT uptake in Nyanza Province, Kenya," *PLoS One* 9(10):1-10, 2014.
Kohler et al., "Shame, guilt, and stress: Community perceptions of barriers to engaging in prevention of mother to child transmission (PMTCT) programs in western Kenya," *AIDS Patient Care STDS* 28(12):643-51, 2014.
Koumans et al., "Indications for therapy and treatment recommendations for bacterial vaginosis in nonpregnant and pregnant women: a synthesis of data," *Clin. Infect. Dis.* 35(Suppl 2): S152-72, 2002.
Koumans et al., "The prevalence of bacterial vaginosis in the United States, 2001-2004; associations with symptoms, sexual behaviors, and reproductive health," *Sex. Transm. Dis.* 34(11):864-9, 2007.
Kumar et al., "Human Tissue-Resident Memory T Cells Are Defined by Core Transcriptional and Functional Signatures in Lymphoid and Mucosal Sites," *Cell Rep.* 20(12):2921-34, 2017.
Kumwenda et al., "HIV incidence among women of reproductive age in Malawi and Zimbabwe," *Sex. Transm. Dis.* 33(11):646-51, 2006.
Kuypers et al., "Comparison of real-time PCR assays with fluorescentantibody assays for diagnosis of respiratory virus infections in children," *J. Clin. Microbiol.* 44(7): 2382-8, 2006.
Kyongo et al., "Cross-Sectional Analysis of Selected Genital Tract Immunological Markers and Molecular Vaginal Microbiota in Sub-Saharan African Women, with Relevance to HIV Risk and Prevention," *Clinical and Vaccine Immunology: CVI.* 22(5):526-38, 2015.
Lai et al., "Human immunodeficiency virus type 1 is trapped by acidic but not by neutralized human cervicovaginal mucus," *J. Virol.* 83(21):11196-111200, 2009.
Lajoie et al., "A distinct cytokine and chemokine profile at the genital mucosa is associated with HIV-1 protection among HIV-exposed seronegative commercial sex workers," *Mucosal Immunology* 5(3):277-87, 2012.
Lajoie et al., "Association of sex work with reduced activation of the mucosal immune system," *J. Infect. Dis.* 210(2):319-29, 2014.
Lajoie et al., "Preventing HIV infection without targeting the virus: how reducing HIV target cells at the genital tract is a new approach to HIV prevention," *AIDS Res. Ther.* 14:46, 2017.
Lajoie et al., "Using safe, affordable and accessible non-steroidal anti-inflammatory drugs to reduce the number of HIV target cells in the blood and at the female genital tract," *J. Int. AIDS Soc.* 21:2018, (14 pages).
Lee et al., "Autophagy-dependent viral recognition by plasmacytoid dendritic cells," *Science* 315:1398-1401, 2007.
Lin et al., "Variable selection in regression with compositional covariates," *Biometrika* 101(4):785-97, 2014.
Lokken et al., "A prospective cohort study of the association between body mass index and incident bacterial vaginosis," *Sex. Transm. Dis.* 46(1):31-6, 2019.
Lokken et al., "Association of Recent Bacterial Vaginosis With Acquisition of *Mycoplasma genitalium*," *Am. J. Epidemiol.* 186(2):194-201, 2017.
Low et al., "Intravaginal Practices, Bacterial Vaginosis, and HIV Infection in Women: Individual Participant Data Meta-analysis," *PLoS Med.* 8(2):2011, (14 pages).
Lowe et al., "A computer program for selection of ogionucleotide primers for polymerase chain reactions," *Nucleic Acids Research* 18(7):1757-1761, 1989.
Lu et al., "Optimal Recall Period and Response Task for Self-Reported HIV Medication Adherence," *AIDS Behav.* 12:86-94, 2008.
Lund et al., "Coordination of early protective immunity to viral infection by regulatory T cells," *Science* 320:1220-1224, 2008.
Lund et al., "Cutting Edge: Plasmacytoid Dendritic Cells Provide Innate Immune Protection against Mucosal Viral Infection In Situ," *J Immunol* 177:7510-7514, 2006.
Lund et al., "HIV-1-neutralizing IgA is detected in genital secretions of highly HIV-1 exposed seronegative women on oral pre-exposure prophylaxis," *J Virol* 90(21):9855-9861, 2016.
Lund et al., "Recognition of single-stranded RNA viruses by Toll-like receptor 7," *Proc Natl Acad Sci USA* 101:5598-5603, 2004.
Lund et al., "Toll-like Receptor 9-mediated Recognition of Herpes Simplex Virus-2 by Plasmacytoid Dendritic Cells," *J Exp Med* 198(3):513-520, 2003.
Mack et al., "Barriers and facilitators to pre-exposure prophylaxis (PrEP) eligibility screening and ongoing HIV testing among target populations in Bondo and Rarieda, Kenya: results of a consultation with community stakeholders," *BMC Health Serv. Res.* 14:1-12, 2014.
Magdaleno-Tapial et al., "Haemophilus species isolated in urethral exudates as a possible causative agent in acute urethritis: a study of 38 Cases," *Actas Dermosifiliogr.* 110(1):38-42, 2019.
Manhart et al., "Bacterial vaginosis-associated bacteria in men: association of Leptotrichia/Sneathia spp. With nongonococcal urethritis," *Sex Transm Dis.* 40(12):944-949, 2013.
Manhart et al., "Standard treatment regimens for nongonococcal urethritis have similar but declining cure rates: a randomized controlled trial," *Clin. Infect. Dis.* 56:934-42, 2013.
Marconi et al., "Do Atopobium vaginae, Megasphaera sp. and Leptotrichia sp. change the local innate immune response and sialidase activity in bacterial vaginosis?" *Sex. Transm. Infect.* 89:167-173, 2013.
Marrazzo et al., "Extravaginal Reservoirs of Vaginal Bacteria as Risk Factors for Incident Bacterial Vaginosis," *Journal of Infectious Diseases.* 205:1580-1588, 2012.
Marrazzo et al., "Relationship of specific vaginal bacteria and bacterial vaginosis treatment failure in women who have sex with women," *Ann Intern Med.* 149(1):20-28, 2008.
Marrazzo et al., "Tenofovir-based preexposure prophylaxis for HIV infection among African women," *N. Engl. J. Med.* 372(6):509-518, 2015.
Martin et al., "Hormonal contraception, sexually transmitted diseases, and risk of heterosexual transmission of human immunodeficiency virus type 1," *J. Infect. Dis.* 178:1053-59, 1998.

(56) References Cited

OTHER PUBLICATIONS

Martin et al., "Vaginal lactobacilli, microbial flora, and risk of human immunodeficiency virus type 1 and sexually transmitted disease acquisition," *J. Infect. Dis.* 180:1863-8, 1999.

Masese et al., "A pilot study of the feasibility of a vaginal washing cessation intervention among Kenyan female sex workers," *Sex. Transm. Infect.* 89:217-22, 2013.

Masese et al., "Changes in the Contribution of Genital Tract Infections to HIV acquisition among Kenyan High-Risk Women from 1993 to 2012," *AIDS* 29:1077-1085, 2015.

Masese et al., "Incident herpes simplex virus type 2 infection increases the risk of subsequent episodes of bacterial vaginosis," *J Infect Dis.* 209:1023-1027, 2014.

Masson et al., "Genital inflammation and the risk of HIV acquisition in women," *Clin. Infect. Dis.* 61:260-9, 2015.

Matsen et al., "pplacer: linear time maximum-likelihood and Bayesian phylogenetic placement of sequences onto a fixed reference tree," *BMC Bioinform.* 11:1-16, 2010.

Mayer et al., "Rapid and Profound Shifts in the Vaginal Microbiota Following Antibiotic Treatment for Bacterial Vaginosis," *J. Infect. Dis.* 212:793-802, 2015.

Mbizvo et al., "HIV seroprevalence and its associations with the other reproductive tract infections in asymptomatic women in Harare, Zimbabwe," *Int. J. STD. AIDS* 12:524-31, 2001.

McClelland et al., "A 15 year study of the Impact of community antiretroviral therapy coverage on HIV incidence in Kenyan female sex workers," *AIDS* 29:2279-86, 2015.

McClelland et al., "A prospective study of risk factors for bacterial vaginosis in HIV-1-seronegative African women," *Sex. Transm. Dis.* 35(6):617-23, 2008.

McClelland et al., "Evaluation of the association between the concentrations of key vaginal bacteria and the increased risk of HIV acquisition in African women from five cohorts: a nested case-control study," *Lancet Infect. Dis.* 18:554-564, 2018.

McClelland et al., "Improvement of vaginal health for Kenyan women at risk for acquisition of human immunodeficiency virus type 1: results of a randomized trial," *J. Infect. Dis.* 197:1361-8, 2008.

McClelland et al., "Infection with Trichomonas vaginalis Increases the Risk of HIV-1 Acquisition," *J. Infect. Dis.* 195:698-702, 2007.

McClelland et al., "Randomized trial of periodic presumptive treatment with high-dose intravaginal metronidazole and miconazole to prevent vaginal infections in HIV-negative women," *J. Infect. Dis.* 211:1875-1882, Jun. 2015.

McClelland et al., "Treatment with antiretroviral therapy is not associated with increased sexual risk behavior in Kenyan female sex workers," *AIDS* 24(6):891-897, 2010.

McClelland et al., "Vaginal washing and increased risk of HIV-1 acquisition among African women: a 10-year prospective study," *AIDS* 20(2):269-73, 2006.

McKinnon et al., "Optimizing Viable Leukocyte Sampling from the Female Genital Tract for Clinical Trials: An International Multi-Site Study," *PLoS One.* 9(1):e85675, Jan. 2014.

McLaren et al., "HIV-Exposed Seronegative Commercial Sex Workers Show a Quiescent Phenotype in the CD4+ T Cell Compartment and Reduced Expression of HIV-Dependent Host Factors," *J. Infect. Dis.* 202(Suppl. 3):S339-44, 2010.

Meda et al., "Sexually transmitted diseases and human immunodeficiency virus infection among women with genital infections in Burkina Faso," *Int. J. STD AIDS* 6(4):273-7, Jul./Aug. 1995.

Menard et al., "High Concentrations of Atopobium vaginae and Gardnerella vaginalis in Women Undergoing Preterm Labor," *Obstet. Gynecol.* 115(1):134-40, Jan. 2010.

Mirmonsef et al., "The Role of Bacterial Vaginosis and Trichomonas in HIV Transmission Across The Female Genital Tract," *Curr. HIV Res.* 10(3):202-210, Apr. 2012.

Mitchell et al., "Bacterial vaginosis and the cervicovaginal immune response," *Am. J. Reprod. Immunol.* 71(6):555-63, Jun. 2014.

Mitchell et al., "Interaction Between Lactobacilli, Bacterial Vaginosis-Associated Bacteria and HIV Type 1 RNA and DNA Genital Shedding in US and Kenyan Women," *AIDS Res Hum Retroviruses* 29(1):13-19, 2013.

Mitchell et al., "Vaginal Microbiota and Mucosal Immune Markers in Women With Vulvovaginal Discomfort," *Sexually Transmitted Diseases* 47(4): 269-274, Apr. 2020.

Mitov et al., "Multitype branching processes with inhomogeneous poisson immigration," Advances in Applied Probability, 50(A): 211-228, 2018.

Moi et al., "Microscopy of Stained Urethral Smear in Male Urethritis; Which Cutoff Should be Used?" *Sex. Transm. Dis.* 44(3): 189-94, Mar. 2017.

Moodley et al., "Interrelationships among Human Immunodeficiency Virus Type 1 Infection, Bacterial Vaginosis, Trichomoniasis, and the Presence of Yeasts," *J. Infect. Dis.* 185(1):69-73, Jan. 2002.

Morrison et al., "Hormonal contraception and the risk of HIV acquisition," *AIDS* 21(1):85-95, 2007.

Msuya et al., "Reproductive tract infections and the risk of HIV among women in Moshi, Tanzania," *Acta Obstet. Gynecol. Scand.* 81(9):886-93, 2002.

Munch et al., "Optimizing bacterial DNA extraction in urine," *PLoS One* 14(9): e0222962, Sep. 2019.

Murray et al., "Global, regional, and national incidence and mortality for HIV, tuberculosis, and malaria during 1990-2013: a systematic analysis for the Global Burden of Disease Study 2013," *Lancet* 384(9947):1005-70, Sep. 2014.

Myer et al., "Bacterial Vaginosis and Susceptibility to HIV Infection in South African Women: A Nested Case-Control Study," *J. Infect. Dis.* 192(8):1372-80, Oct. 2005.

Naranbhai et al., "Innate Immune Activation Enhances HIV Acquisition in Women, Diminishing the Effectiveness of Tenofovir Microbicide Gel," *J. Infect. Dis.* 206(7):993-1001, Oct. 2012.

Naslund et al., "Exosomes from breast milk inhibit HIV-1 infection of dendritic cells and subsequent viral transfer to CD4+ T cells," *AIDS* 28(2):171-80, 2014.

Nawrocki et al., "Infernal 1.1: 100-fold faster RNA homology searches," *Bioinformatics* 29(22): 2933-5, 2013.

Nduati et al., "Effect of Breastfeeding and Formula Feeding on Transmission of HIV-1: A Randomized Clinical Trial," *JAMA* 283(9):1167-1174, Mar. 2000.

Nduati et al., "Effect of breastfeeding on mortality among HIV-1 infected women: a randomised trial," *Lancet* 357(9269):1651-5, May 2001.

Nelson et al., "Early Pregnancy Changes in Bacterial Vaginosis-associated Bacteria and Preterm Delivery," *Paediatric and Perinatal Epidemiology* 28(2):88-96, Mar. 2014.

Nelson et al., "Preterm labor and bacterial vaginosis-associated bacteria among urban women," *Journal of Perinatal Medicine* 37(2):130-4, 2009.

Noecker et al., "Metabolic Model-Based Integration of Microbiome Taxonomic and Metabolomic Profiles Elucidates Mechanistic Links between Ecological and Metabolic Variation," *mSystems* 1(1): e00013-15, 2016.

Noel-Romas et al., "Microbiome-Associated Epithelial Disruption Modifies HIV Acquisition Risk in Women," Poster #271, *25th Conference on Retroviruses and Opportunistic Infections*, Boston, Massachussetts, USA, Mar. 4-7, 2018, 1 page.

Noguchi et al., "Risk of HIV-1 acquisition among women who use different types of injectable progestin contraception in South Africa: a prospective cohort study." *Lancet HIV* 2(7):e279-87, Jul. 2015.

Turner et al., "Recent Biomarker-Confirmed Unprotected Vaginal Sex, But Not Self-reported Unprotected Sex, Is Associated With Recurrent Bacterial Vaginosis," *Sex. Transm. Dis.* 43(3):172-6, Mar. 2016.

Nugent et al., "Reliability of Diagnosing Bacterial Vaginosis Is Improved by a Standardized Method of Gram Stain Interpretation," *J. Clin. Microbiol.* 29(2):297-301, Feb. 1991.

Nunn et al., "Enhanced Trapping of HIV-1 by Human Cervicovaginal Mucus Is Associated with Lactobacillus crispatus-Dominant Microbiota," *mBio.* 6(5):e01084-15, Sep./Oct. 2015.

(56) References Cited

OTHER PUBLICATIONS

O'Malley et al., "Scaling-up PrEP Delivery in Sub-Saharan Africa: What Can We Learn from the Scale-up of ART?" *Current HIV/AIDS Reports* 16(2):141-50, 2019.
Oakeshott et al., Is Mycoplasma genitalium in Women the "New Chlamydia? A Community-Based Prospective Cohort Study," *Clin. Infect. Dis.* 51(10):1160-6, Nov. 2010.
Odeny et al., "Developing Content for a mHealth Intervention to Promote Postpartum Retention in Prevention of Mother-To-Child HIV Transmission Programs and Early Infant Diagnosis of HIV: A Qualitative Study," *PLoS One* 9(9):e106383, Sep. 2014.
Odeny et al., "Participation in a clinical trial of a text messaging intervention is associated with increased infant HIV testing: A parallel-cohort randomized controlled trial," *PLoS One* 13(12): e0209854, Dec. 2018.
Odeny et al., "Text messaging for maternal and infant retention in prevention of mother-to- child HIV transmission services: A pragmatic stepped-wedge cluster-randomized trial in Kenya," *PLoS Med.* 16(10):e1002924, Oct. 2019.
Odeny et al., "Texting improves testing: a randomized trial of two-way SMS to increase postpartum prevention of mother-to-child transmission retention and infant HIV testing," *AIDS* 28:2307-2312, 2014.
Ozyurt et al., "Efficacy of 7-day treatment with metronidazole+ miconazole (Neo-Penotran)—a triple-active pessary for the treatment of single and mixed vaginal infections," *Int. J. Gynaecol. Obstet.* 74(1):35-43, 2001.
Passmore et al., "Role of vaginal microbiota in genital inflammation and enhancing HIV acquisition in women," Webcast presentation at AIDS Conference 2016, Durban, South Africa, Jul. 19, 2016, URL=http://programme.aids2016.org/Programme/Session/1257, download date Nov. 18, 2021. (3 pages).
Pattacini et al., "A pro-inflammatory CD8+ T cell subset patrols the cervicovaginal tract," *Mucosal Immunology* 12(5):1118-1129, 2019.
Pattacini et al., "Antiretroviral Pre-Exposure Prophylaxis Does Not Enhance Immune Responses to HIV in Exposed but Uninfected Persons," *J Infect Dis* 211:1943-1952, Jun. 2015.
Pattacini et al., "Enhanced and efficient detection of virus-driven cytokine expression by human NK and T cells," *J Virol Methods* 199:17-24, 2014.
Pattacini et al., "Regulatory T-Cell Activity But Not Conventional HIV-Specific T-Cell Responses Are Associated With Protection From HIV-1 Infection," *J. Acquir. Immune. Defic. Syndr.* 72(2):119-28, Jun. 2016.
Pauk et al., "Mucosal shedding of human herpesvirus 8 in men," *N. Engl. J. Med.* 343(19):1369-77, 2000.
Peebles et al., "High Global Burden and Costs of Bacterial Vaginosis: A Systematic Review and Meta-Analysis," *Sex. Transm. Dis.* 46(5):304-11, May 2019.
Pekmezovic et al., "Host-Pathogen Interactions during Female Genital Tract Infections," *Trends. Microbiol.* 27(12):982-96, Dec. 2019.
Peng et al., "A Global Estimate of the Acceptability of Pre-exposure Prophylaxis for HIV Among Men Who have Sex with Men: A Systematic Review and Meta-analysis," AIDS Behav. 22(4): 1063-74, 2017.
Pennisi et al., "An overview of reactive arthritis," *JAAPA* 32(7):25-8, Jul. 2019.
Pfau et al., "The bacterial flora of the vaginal vestibule, urethra and vagina in premenopausal women with recurrent urinary tract infections," *J. Urol.* 126(5):630-4, 1981.
Pintye et al., "Integration of PrEP services into routine antenatal and postnatal care: experiences from an implementation program in Western Kenya," *J Acquir Immune Defic Syndr* 79(5):590-595, Dec. 15, 2018.
Polis et al., "An updated systematic review of epidemiological evidence on hormonal contraceptive methods and HIV acquisition in women," *AIDS* 30(17):2665-2683, Aug. 3, 2016.
Poulin et al., "Antibiotic susceptibilities of AIDS-associated mycoplasmas," *J. Clin. Microbiol.* 32(4):1101-1103, Apr. 1994.

Psaros et al., "An intervention to support HIV preexposure prophylaxis adherence in HIV serodiscordant couples in Uganda," *J Acquir Immune Defic Syndr.* 66(5):522-529, Aug. 15, 2014.
Radtke et al., "Microbial products alter the expression of membrane-associated mucin and antimicrobial peptides in a three-dimensional human endocervical epithelial cell model," *Biology of Reproduction* 87(6):132, Oct. 2012. (10 pages).
Rane et al., "Characteristics of acute nongonococcal urethritis in men differ by sexual preference," *J. Clin. Microbiol.* 52(8): 2971-2976, Aug. 2014.
Rasmussen et al., "Antimicrobial resistance in *Bacteroides*," *Clin. Infect. Dis.* 16(Suppl 4):S390-400, 1993. (12 pages).
Rathod et al., "Bacterial vaginosis and risk for *Trichomonas vaginalis* infection: a longitudinal analysis," *Sex Transm Dis.* 38(9):882-886, Sep. 2011.
Rebbapragada et al., "Bacterial vaginosis in HIV-infected women induces reversible alterations in the cervical immune environment," *J Acquir Immune Defic Syndr* 49(5):520-522, Dec. 15, 2008.
Reid, "Therapeutic Opportunities in the Vaginal Microbiome," *Microbiol Spectr* 5(3):1-9, 2017.
Richardson et al., "Appropriateness of hydroxyethylcellulose gel as a placebo control in vaginal microbicide trials: a comparison of the two control arms of HPTN 035," *J Acquir Immune Defic Syndr* 63(1):120-125, May 1, 2013.
Richardson et al., "Comparison of human immunodeficiency virus type 1 viral loads in Kenyan women, men, and infants during primary and early infection," *J Virol.* 77(12):7120-7123, Jun. 2003.
Richardson et al., "Evaluation of a low-dose nonoxynol-9 gel for the prevention of sexually transmitted diseases: a randomized clinical trial," *Sex Transm Dis.* 28(7):394-400, Jul. 2001.
Richardson et al., "Hormonal contraception and HIV-1 disease progression among postpartum Kenyan women," *AIDS* 21(6):749-753, 2007.
Richardson et al., "Modeling breastmilk infectivity in HIV-1 infected mothers," *Biometrics* 59:179-185, Mar. 2003.
Richardson et al., "Product limit estimation for infectious disease data when the diagnostic test for the outcome is measured with uncertainty," *Biostatistics* 1(3):341-354, 2000.
Richardson et al., "Vertical cytomegalovirus transmission from HIV-infected women randomized to formula-feed or breastfeed their infants," *J Infect Dis.* 213:992-998, Mar. 15, 2016.
Richardson, "Nonoxynol-9 as a vaginal microbicide for prevention of sexually transmitted infections: it's time to move on," *JAMA* 287(9):1171-1172, Mar. 6, 2002.
Richert-Spuhler et al., "Pre-exposure prophylaxis differentially alters circulating and mucosal immune cell activation in herpes simplex virus type 2 seropositive women," *AIDS* 33(14):2125-2136, 2019.
Riedner et al., "Baseline survey of sexually transmitted infections in a cohort of female bar workers in Mbeya Region, Tanzania," *Sex Transm Infect* 79(5):382-387, Apr. 14, 2003.
Ronen et al., "HIV-1 superinfection is associated with an accelerated viral load increase but has a limited impact on disease progression," *AIDS* 28(15):2281-2286, 2014.
Roxby et al., "Changes in Vaginal Microbiota and Immune Mediators in HIV-1-Seronegative Kenyan Women Initiating Depot Medroxyprogesterone Acetate," *J Acquir Immune Defic Syndr* 71(4):359-366, Apr. 1, 2016. (17 pages).
Royce et al., "Bacterial vaginosis associated with HIV infection in pregnant women from North Carolina," *J Acquir Immune Defic Syndr Hum Retrovirol* 20(4):382-386, Apr. 1, 1999.
Rugpao et al., "Gynaecological conditions associated with HIV infection in women who are partners of HIV-positive Thai blood donors," *Int. J. STD AIDS* 9(11):677-682, Nov. 1998.
Sabo et al., "Associations between vaginal bacteria implicated in HIV acquisition risk and proinflammatory cytokines and chemokines," *Sex Transm Infect* 96:3-9, 2020.
Saeland et al., "MUC1 in human milk blocks transmission of human immunodeficiency virus from dendritic cells to T cells," *Mol. Immunol.* 46:2309-2316, 2009.
Safren et al., "Two strategies to increase adherence to HIV antiretroviral medication: life-steps and medication monitoring," *Behav. Res. Ther.* 39:1151-1162, 2001.

(56) References Cited

OTHER PUBLICATIONS

Sagay et al., "HIV infection among pregnant women in Nigeria," *Int. J. Gynaecol. Obstet.* 90:61-67, 2005.

Sallusto et al., "Heterogeneity of CD4+ memory T cells: functional modules for tailored immunity," *Eur. J. Immunol.* 39:2076-2082, 2009.

Schiffer et al., "A fixed spatial structure of CD8+ T cells in tissue during chronic HSV-2 infection," *J Immunol* 201: 1522-1535, Jul. 2018. (20 pages).

Schulz et al., "CONSORT 2010 statement: updated guidelines for reporting parallel group randomised trials," *BMC Medicine* 8:18, 2010. (9 pages).

Schwebke et al., "Re-evaluating the treatment of nongonococcal urethritis: emphasizing emerging pathogens-a randomized clinical trial," *Clin. Infect. Dis.* 52(2):163-170, 2011.

Schwebke, "Asymptomatic bacterial vaginosis: response to therapy," *Am. J. Obstet. Gynecol.* 183(6):1434-1439, 2000.

Scorgie et al., "Abstract No. TUPDC0101—Measuring perceptions of sexual risk among adolescent girls and young women taking PrEP: a new qualitative method using visual timelines in HPTN 082," Oral abstracts of the 10th IAS Conference on HIV Science, Mexico City, Mexico, Jul. 21-24, 2019. (3 pages).

Sewankambo et al., "HIV-1 infection associated with abnormal vaginal flora morphology and bacterial vaginosis," *The Lancet* 350:1780, Dec. 13, 1997.

Shukair et al., "Human cervicovaginal mucus contains an activity that hinders HIV-1 movement," *Mucosal Immunology* 6(2):427-434, Mar. 2013. (20 pages).

Sobel et al., "Suppressive antibacterial therapy with 0.75% metronidazole vaginal gel to prevent recurrent bacterial vaginosis," *Am. J. Obstet. Gynecol.* 194(5):1283-1289, 2006.

Soerens et al., "Regulatory T cells are essential to promote proper CD4 T-cell priming upon mucosal infection," *Mucosal Immunology* 9(6):1395-1406, Nov. 2016.

Songok et al., "Microarray analysis of HIV resistant female sex workers reveal a gene expression signature pattern reminiscent of a lowered immune activation state," *PloS One* 7(1):e30048, Jan. 2012. (10 pages).

Spandorfer et al., "Relationship of abnormal vaginal flora, proinflammatory cytokines and idiopathic infertility in women undergoing IVF," *J. Reprod. Med.* 46(9):806-810, Sep. 2001.

Srinivasan et al., "Abstract 404: Association Between Vaginal Bacteria and HIV Acquisition Risk Among African Women Participating in the VOICE Study," Abstract presented at the *STI & HIV 2019 World Congress conference*, Vancouver, Canada, Jul. 14-17, 2019. (1 page).

Srinivasan et al., "Abstract P523: Urethral microbiota in idiopathic Non-Gonococcal Urethritis (NGU) in men who have sex with men and men who have sex with women," *Sex Transm Infect* 95(Suppl 1):A238-A239, presented at the *STI & HIV 2019 World Congress conference*, Vancouver, Canada, Jul. 16, 2019. (2 pages).

Srinivasan et al., "Abstract P587: Association Between Vaginal Bacteria and HIV Acquisition Risk Among African Women Participating in the VOICE Study," *Sex Transm Infect* 95(Suppl 1):A262, Abstract presented at the *STI & HIV 2019 World Congress conference, Vancouver*, Canada, Jul. 16, 2019. (1 page).

Srinivasan et al., "Association Between Vaginal Bacteria and HIV Acquisition Risk Among African Women Participating in the VOICE Study," poster presented at the *STI & HIV 2019 World Congress conference*, Vancouver, Canada, Jul. 14-17, 2019. (1 page).

Srinivasan et al., "Bacterial communities in women with bacterial vaginosis: high resolution phylogenetic analyses reveal relationships of microbiota to clinical criteria," *PLoS One* 7(6):e37818, Jun. 2012. (15 pages).

Srinivasan et al., "Metabolic signatures of bacterial vaginosis," *mBio* 6(2):e00204-15, Mar./Apr. 2015. (16 pages).

Srinivasan et al., "More easily cultivated than identified: classical isolation with molecular identification of vaginal bacteria," *J Infect Dis.* 214(Suppl 1):S21-S28, 2016.

Srinivasan et al., "More Than Meets the Eye: Associations of Vaginal Bacteria with Gram Stain Morphotypes Using Molecular Phylogenetic Analysis," *PLoS One* 8(10): e78633, Oct. 2013.

Srinivasan et al., "Periodic Presumptive Treatment (PPT) with Metronidazole Reduces Abundance of Vaginal Bacteria Associated with HIV Risk" Abstract from *Keystone Symposia—Microbiome: Therapeutic Implications*, Killarney, Ireland, Oct. 6-10, 2019. (1 page).

Srinivasan et al., "Periodic Presumptive Treatment (PPT) with Metronidazole Reduces Abundance of Vaginal Bacteria Associated with HIV Risk" Post er from *Keystone Symposia—Microbiome: Therapeutic Implications*, Killarney, Ireland, Oct. 6-10, 2019. (1 page).

Srinivasan et al., "Temporal variability of human vaginal bacteria and relationship with bacterial vaginosis," *PLoS One* 5(4):e10197, Apr. 2010.

Srinivasan et al., "Urethral microbiota in idiopathic Non-Gonococcal Urethritis in men who have sex with men and men who have sex with women," poster presented at the *STI & HIV 2019 World Congress conference*, Vancouver, Canada, Jul. 16, 2019. (1 page).

Srinivasan et al., "Vaginal microbiota and HIV acquisition risk among African women," Poster #268, *25th Conference on Retroviruses and Opportunistic Infections*, Boston, Massachussetts, USA, Mar. 4-7, 2018. (1 page).

Stamey et al., "The role of vaginal colonization with enterobacteriaceae in recurrent urinary infections," *J. Urol.* 113:214-217, Feb. 1975.

Stapleton, "The Vaginal Microbiota and Urinary Tract Infection," *Microbiol Spectr* 4(6):UTI-0025-2016, 2016. (6 pages).

Sturm, "*Haemophilus influenzae and Haemophilus parainfluenzae* in nongonococcal urethritis," *J. Infect. Dis.* 153(1):165-167, Jan. 1986.

Sturm-Ramirez et al., "High levels of tumor necrosis factor-α and interleukin-1ß in bacterial vaginosis may increase susceptibility to human immunodeficiency virus," *J. Infect. Dis.* 182:467-473, Aug. 2000.

Swedberg et al., "Comparison of single-dose vs one-week course of metronidazole for symptomatic bacterial vaginosis," *JAMA* 254(8):1046-1049, Aug. 1985.

Taha et al., "Bacterial vaginosis and disturbances of vaginal flora: association with increased acquisition of HIV," *AIDS* 12(13):1699-1706, 1998.

Taha et al., "HIV infection and disturbances of vaginal flora during pregnancy," *J. Acquir. Immune Defic. Syndr. Hum. Retrovirol.* 20(1):52-59, Jan. 1, 1999.

Taylor-Robinson et al., "Detection of several *Mycoplasma* species at various anatomical sites of homosexual men," *Eur. J. Clin. Microbiol. Infect. Dis.* 22:291-293, May 7, 2003.

Taylor-Robinson et al., "Update on sexually transmitted mycoplasmas," *Lancet* 351(Suppl III):12-15, 1998.

Thurman et al., "Bacterial Vaginosis and Subclinical Markers of Genital Tract Inflammation and Mucosal Immunity," *AIDS Res. Hum. Retroviruses* 31(11):1139-1152, 2015.

UNAIDS, "UNAIDS Data 2019," Joint United Nations Programme on HIV/AIDS, Geneva, Switzerland, 2019. (476 pages).

Van de Wijgert et al., "Bacterial vaginosis and vaginal yeast, but not vaginal cleansing, increase HIV-1 acquisition in African women," *J Acquir Immune Defic Syndr* 48(2):203-210, Jun. 1, 2008.

Van de Wijgert et al., "Disentangling Contributions of Reproductive Tract Infections to HIV Acquisition in African Women," *Sex. Transm. Dis.* 36(6):357-364, Jun. 2009.

Vancutsem et al., "Modified real-time PCR for detecting, differentiating, and quantifying *Ureaplasma urealyticum and Ureaplasma parvum,*" *J. Mol. Diagn.* 13(2): 206-212, Mar. 2011.

Velloza et al., "A clinic-based tablet application to support safer conception among HIV serodiscordant couples in Kenya: feasibility and acceptability study," *mHealth* 5:4, 2019. (14 pages).

Velloza et al., "Alcohol use and antiretroviral therapy non-adherence among adults living with HIV/AIDS in sub-Saharan Africa: a systematic review and meta-analysis," *AIDS Behav.* 24:1727-1742, 2020.

(56) References Cited

OTHER PUBLICATIONS

Velloza et al., "Cognitive testing of the PHQ-9 for depression screening among pregnant and postpartum women in Kenya," *BMC Psychiatry* 20:31, 2020. (14 pages).

Velloza et al., "Comprehensive HIV risk reduction interventions for 2020 and beyond: Product choices and effective service-delivery platforms for individual needs and population-level impact," *Curr Opin HIV AIDS* 14(5):423-432, Sep. 2019.

Velloza et al., "Depression and ART initiation among HIV serodiscordant couples in Kenya and Uganda," *AIDS & Behavior* 21(8):2509-2518, Aug. 2017. (19 pages).

Velloza et al., "Effect of depression on adherence to oral PrEP among men and women in East Africa, " *J Acquir Immune Defic Syndr* 79(3):330-338, Nov. 1, 2018.

Velloza et al., "HIV-risk behaviors and social support among men and women attending alcohol-serving venues in South Africa: Implications for HIV prevention," *AIDS & Behavior* 21(Suppl 2):144-154, Nov. 2017. (17 pages).

Velloza et al., "Short—and long-term pharmacologic measures of HIV pre-exposure prophylaxis use among high-risk men who have sex with men in HPTN 067/ADAPT," *J Acquir Immune Defic Syndr* 82(2):149-158, Oct. 1, 2019.

Velloza et al., "Stages and processes of change utilized by female sex workers participating in an alcohol-reduction intervention in Mombasa, Kenya," *Substance Use & Misuse* 50:1728-1737, 2015.

Velloza et al., "The influence of HIV-related stigma on PrEP disclosure and adherence among adolescent girls and young women in HPTN 082: a qualitative study," *Journal Int AIDS Soc.* 23:e25463, 2020. (10 pages).

Velloza et al., "The vaginal microbiome and its potential to impact efficacy of HIV pre-exposure prophylaxis for women," *Current HIV/AIDS Reports* 14(5):153-160, Oct. 2017. (14 pages).

Velonjara et al., "Motherhood increases support for family planning among Kenyan adolescents," *Sex Reprod Healthc* 16:124-131, Jun. 2018. (18 pages).

Warren et al., "A multicenter study of bacterial vaginosis in women with or at risk for human immunodeficiency virus infection," *Infect Dis Obstet Gynecol* 9:133-141, May 28, 2001.

Watt et al., "'It's better for me to drink, at least the stress is going away': Perspectives on alcohol use during pregnancy among South African women attending drinking establishments, " *Social Science and Medicine* 116:119-125, Sep. 2014. (16 pages).

Watt et al., "Development of an intervention to improve mental health for obstetric fistula patients in Tanzania," *Evaluation and Program Planning* 50:1-9, Jun. 2015. (24 pages).

Watt et al., "Experiences of forced sex among female patrons of alcohol-serving venues in a South African township," *Journal of Interpersonal Violence* 30(9):1533-1552, May 2015. (18 pages).

Wen et al., "Selected vaginal bacteria and risk of preterm birth: an ecological perspective," *J. Infect. Dis.* 209:1087-1094, Apr. 2014.

Wessels et al., "Association of high-risk sexual behaviour with diversity of the vaginal microbiota and abundance of *Lactobacillus*," *PLoS One* 12(11):e0187612, Nov. 2, 2017. (23 pages).

Wessels et al., "Medroxyprogesterone acetate alters the vaginal microbiota and microenvironment in women and increases susceptibility to HIV-1 in humanized mice," *Dis. Model. Mech.* 12, Sep. 11, 2019. (13 pages).

Wessels et al., "The relationship between sex hormones, the vaginal microbiome and immunity in HIV-1 susceptibility in women," *Dis. Model. Mech.* 11, 2018. (15 pages).

Wetmore et al., "Demographic, behavioral, and clinical characteristics of men with nongonococcal urethritis differ by etiology: a case-comparison study," *Sex. Transm. Dis.* 38(3): 180-186, Mar. 2011. (13 pages).

Wetmore et al., "*Ureaplasma urealyticum* is associated with non-gonococcal urethritis among men with fewer lifetime sexual partners: a case-control study," *J. Infect. Dis.* 204:1274-1282, Oct. 2011.

White et al., "Alcohol Use and Associations With Biological Markers and Self-Reported Indicators of Unprotected Sex in HIV-Positive Female Sex Workers in Mombasa, Kenya," *Sex Transm Dis.* 43(10):642-647, Oct. 2016. (14 pages).

Wilson et al., "A Prospective Cohort Study of Fertility Desire, Unprotected Sex, and Detectable Viral Load in HIV-Positive Female Sex Workers in Mombasa, Kenya," *J Acquir Immune Defic Syndr* 78(3):276-282, Jul. 1, 2018. (18 pages).

Wilson et al., "A Prospective Cohort Study of Intimate Partner Violence and Unprotected Sex in HIV-Positive Female Sex Workers in Mombasa, Kenya," *AIDS Behav.* 20(9):2054-2064, Sep. 2016. (16 pages).

Wilson et al., "A Prospective Study of Intimate Partner Violence as a Risk Factor for Detectable Plasma Viral Load in HIV-Positive Women Engaged in Transactional Sex in Mombasa, Kenya," *AIDS Behav.* 20(9):2065-2077, Sep. 2016. (22 pages).

Witkin, "The vaginal microbiome, vaginal anti-microbial defence mechanisms and the clinical challenge of reducing infection-related preterm birth," *BJOG* 122:213-218, 2015.

Workowski et al., "Sexually transmitted diseases treatment guidelines, 2015," *MMWR Recomm Rep.* 64(RR-03):1-137, Jun. 5, 2015. (235 pages).

World Health Organization, "Guidelines for the Management of Sexually Transmitted Infections," WHO Library Cataloguing-in-Publication Data, Geneva, Switzerland, 2003. (98 pages).

Wykowski et al., "Associations Between Anxiety and Adherence to Antiretroviral Medications in Low—and Middle-Income Countries: A Systematic Review and Meta—analysis," *AIDS Behav.* 23(8):2059-2071, Aug. 2019. (17 pages).

Yamakami et al., "PCR Detection of DNA Specific for *Aspergillus* Species in Serum of Patients with Invasive Aspergillosis," *Journal of Clinical Microbiology* 34(10):2464-2468, Oct. 1996.

Yoshida et al., "Polymerase chain reaction-based subtyping of Ureaplasma parvum and Ureaplasma urealyticum in first-pass urine samples from men with or without urethritis," *Sex. Transm. Dis.* 32(7): 454-457, Jul. 2005.

Zevin et al., "Microbiome Composition and Function Drives Wound-Healing Impairment in the Female Genital Tract," *PLoS Pathog.* 12(9):e1005889, Sep. 22, 2016. (20 pages).

Zhu et al., "Persistence of HIV-1 receptor-positive cells after HSV-2 reactivation: a potential mechanism for increased HIV-1 acquisition," *Nature Medicine* 15(8):886-892, Aug. 2009. (18 pages).

\* cited by examiner

KITS AND METHODS FOR ASSESSING A CONDITION OR A RISK OF DEVELOPING A CONDITION, AND RELATED METHODS OF TREATMENT

STATEMENT OF GOVERNMENT INTEREST

This invention was made with government support under AI110666, AI113173, AI068633, AI027757 and HD064915 awarded by the National Institutes of Health. The government has certain rights in the invention.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is 374332_401_Sequence-Listing.TXT. The text file is 42.2 KB, was created on Jul. 12, 2020, and is being submitted electronically via EFS-Web.

BACKGROUND

Technical Field

The present disclosure is directed to kits and methods for diagnosing a condition, assessing a condition, monitoring effectiveness of treatment of a condition, or assessing a risk of developing a condition or acquiring a condition based on the genitourinary microbiome of a subject. Additional embodiments include related methods of treating a condition based on the diagnosis or assessment, including methods of administering a therapeutic agent in order to prevent the condition.

Description of the Related Art

A number of microbiomes are associated with mammals. The presence and/or relative concentrations of various bacterial species can have direct effects on the mammal's health and the mammal's susceptibility to acquiring infections. However, little is known regarding some of these relationships. In particular, the relationship between the genitourinary microbiome and the risk of developing nongonococcal urethritis and/or acquiring human immunodeficiency virus.

BRIEF SUMMARY

The present disclosure provides kits and methods to detect the risk, diagnosis, progression, or prognosis of a condition, monitoring disease progression, monitoring effectiveness of treatment of a condition, assessing a risk of developing a condition, or a risk of acquiring a condition based on the genitourinary microbiome of a subject.

In one aspect, the present disclosure provides a method, comprising detecting and classifying a nongonococcal urethritis (NGU) infection in a male subject comprising detecting a pathogen in a urethral sample from the male subject, the pathogen comprising *Haemophilus influenzae, Mycoplasma penetrans*, or both.

As used herein "Prognosis" is the likelihood of a clinical outcome for a subject affected with a specific condition, disease or disorder. With regard to NGU, the prognosis is the likelihood (probability) that the subject will respond to treatment with a therapeutic agent. With regards to HIV, the prognosis (probability) that the subject will acquire HIV infection.

In another aspect, the present disclosure provides a method for treating a nongonococcal urethritis (NGU) infection in a male subject in need thereof, the method comprising: administering an effective amount of a therapeutic agent to the male subject, the NGU infection having been classified by an in vitro method comprising: detecting a pathogen in a urethral sample from the male subject, the pathogen comprising *Haemophilus influenzae, Mycoplasma penetrans*, or both.

In a further aspect, the present disclosure provides a method for preventing a nongonococcal urethritis (NGU) infection in a male subject in need thereof, the method comprising: administering an effective amount of a therapeutic agent to the male subject, the NGU infection having been classified by an in vitro method comprising: detecting a pathogen in a urethral sample from the male subject, the pathogen comprising *Haemophilus influenzae, Mycoplasma penetrans*, or both.

In another aspect, the present disclosure provides a kit for detecting and classifying a nongonococcal urethritis (NGU) infection in a male subject, the kit comprising: a first primer set that hybridizes to first nucleotide sequences of *Haemophilus influenzae* or *Mycoplasma penetrans* to generate a *Haemophilus influenzae* or *Mycoplasma penetrans* specific amplicon; and a first probe capable of hybridizing to the *Haemophilus influenzae* or *Mycoplasma penetrans* specific amplicon.

In another aspect, the present disclosure provides a kit for detecting and classifying a nongonococcal urethritis (NGU) infection in a male subject, the kit comprising: a first primer set that hybridizes to first nucleotide sequences of *Haemophilus influenzae, Mycoplasma penetrans, Chlamydia trachomatis, Mycoplasma genitalium, Trichomonas vaginalis*, Adenovirus, Herpes simplex virus (HSV)-1, or HSV-2, to generate a *Haemophilus influenzae, Mycoplasma penetrans, Chlamydia trachomatis, Mycoplasma genitalium, Trichomonas vaginalis*, Adenovirus, Herpes simplex virus (HSV)-1, or HSV-2 specific amplicon; and a first probe capable of hybridizing to the *Haemophilus influenzae* or *Mycoplasma penetrans* specific amplicon.

In a further aspect, the present disclosure provides a method, comprising: classifying a risk of human immunodeficiency virus (HIV) infection in a subject comprising detecting a pathogen in a vaginal sample from the subject, the pathogen comprising Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof.

In a further aspect, the present disclosure provides a method, comprising: classifying a risk of human immunodeficiency virus (HIV) infection in a subject comprising detecting a pathogen in a vaginal sample from the subject, the pathogen comprising Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sangui-* negens, *Megasphaera* species type 2, *Mycoplasma hominis*, *Parvimonas* species type 2, or a combination thereof.

In still a further aspect, the present disclosure provides a method for preventing a human immunodeficiency virus (HIV) infection in a subject in need thereof, the method comprising: administering an effective amount of a therapeutic agent, the HIV infection having been classified by an in vitro method comprising: detecting a pathogen in a vaginal sample from the subject, the pathogen comprising Bacterial vaginosis-associated bacterium 2 (BVAB2), vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, or a combination thereof.

In still a further aspect, the present disclosure provides a method for preventing a human immunodeficiency virus (HIV) infection in a subject in need thereof, the method comprising: administering an effective amount of a therapeutic agent, the HIV infection having been classified by an in vitro method comprising: detecting a pathogen in a vaginal sample from the subject, the pathogen comprising Bacterial vaginosis-associated bacterium 2 (BVAB2), vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2, or a combination thereof.

BRIEF DESCRIPTION OF THE SEVERAL VIEWS OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1:
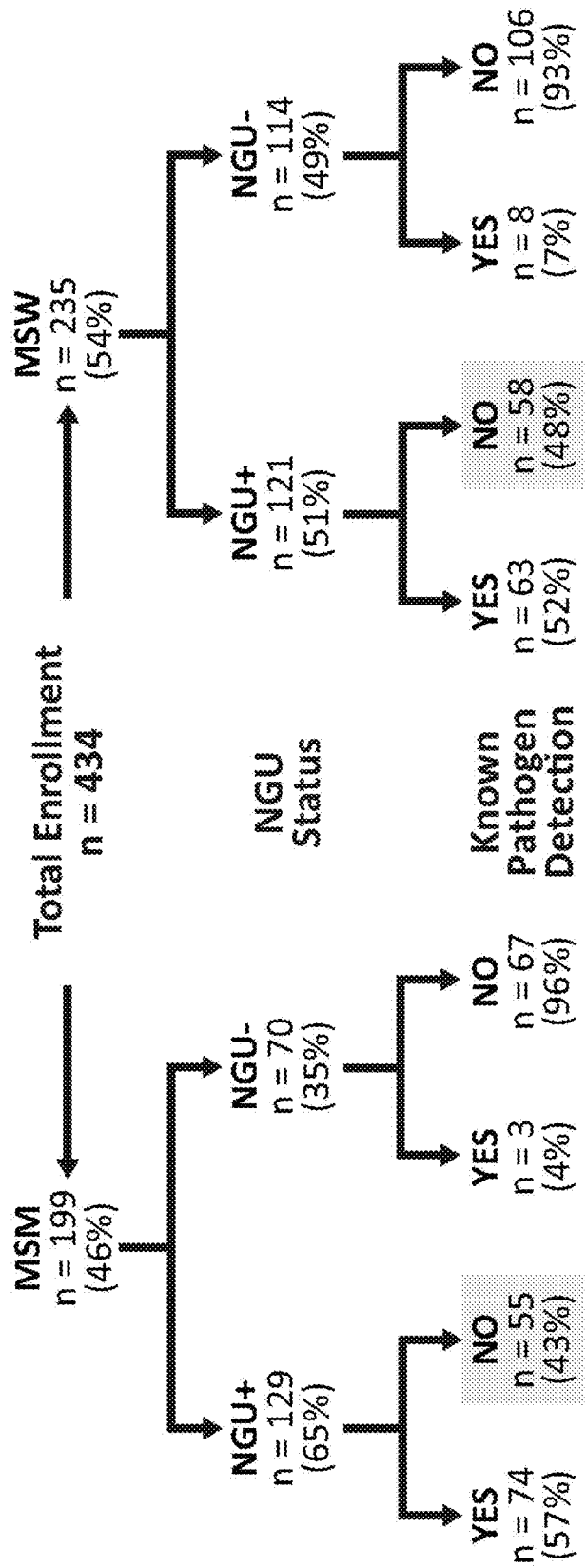
FIG. 1 provides a summary of the subjects enrolled in the study described in Example 1.

The present disclosure provides methods to detect the risk, diagnosis, progression, prognosis, or assessing a condition, monitoring disease progression, monitoring effectiveness of treatment of a condition, or assessing a risk of developing a condition, or a risk of acquiring a condition based on the genitourinary microbiome of a subject. Also provided are kits that can be used in such methods.

Prior to setting forth this disclosure in more detail, it may be helpful to an understanding thereof to provide definitions of certain terms to be used herein. Additional definitions are set forth throughout this disclosure.

As used herein, "nucleic acid" or "nucleic acid molecule" or "polynucleotide" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR.

The nucleic acid can represent a coding strand or its complement. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded. In certain embodiments of the present disclosure, nucleotides or gaps in a nucleic acid sequence are named according to standard IUPAC convention, Specifically, "A" is Adenine, "C" is Cytosine, "G" is Guanine, "T" is Thymine, "U" is Uracil, "R" is any Purine (A or G), "Y" is any Pyrimidine (C, T, or U), "M" is C or A, "K" is T' U' or G' "W" is T' U' or A' "S" is C or G' "B" is C T U' or G (not A)' "D" is A, T, U, or G (not C), "H" is A, T, U, or C (not G), "V" is A, C, or G (not T, not U), "N" is any base (A, C, G, T, or U), and—(gap).

The term "nucleotide sequence" refers to a heteropolymer of nucleotides or the sequence of these nucleotides.

The term "isolated" means that the material is removed from its original environment (e.g., the natural environment if it is naturally occurring). Thus, an isolated biological material can be free of some or all cellular components, i.e., components of the cells in which the native material occurs naturally (e.g., cytoplasmic or membrane component). For example, a naturally occurring nucleic acid present in a microorganism is not isolated, but the same nucleic acid, separated from some or all of the co-existing materials in the natural system, is isolated. A material shall be deemed isolated if it is present in a cell extract or supernatant. In the case of nucleic acid molecules, an isolated nucleic acid includes a PCR product, an isolated mRNA, a cDNA, or a restriction fragment.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids.

In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like.

The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The term "purified" as used herein refers to material that has been isolated under conditions that reduce or eliminate the presence of unrelated materials, i.e., contaminants, including native materials from which the material is obtained. For example, a purified DNA is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Techniques to isolate and purify specific nucleic acids and proteins are well known to those of skill in the art. In accordance with the present disclosure there may be employed conventional molecular biology, microbiology, and recombinant DNA techniques within the skill of the art. Such techniques are explained fully in the literature. See, e.g., Sambrook et al., Molecular Cloning: A Laboratory Manual, Second Edition (Cold Spring Harbor, NY: Cold Spring Harbor Laboratory Press, 1989).

The term "gene" means the segment of DNA involved in producing a polypeptide chain; it includes regions preceding and following the coding region "leader and trailer" as well as intervening sequences (introns) between individual coding segments (exons). A "locus" (plural: loci) is a specific location of a gene or DNA sequence in or on a chromosome. "Alleles" are variants of a DNA sequence located at a given locus.

As used herein, the term "conserved region" or "conserved sequence" refers to a nucleotide sequence in a region of a gene that is the same or highly similar across different species. For example, a sequence or region of a gene that is conserved may have the same nucleotide sequence in several types of species, or, in some cases, may have the same or highly similar sequence across different taxonomic phyla (e.g., a human DNA sequence and a DNA sequence in a highly conserved region of a gene may be the same or highly similar). Conversely, a "variable" region or sequence of a gene is not conserved across species or phyla, and will have many nucleotides differences in the hypervariable region in the gene from each species.

"Sequence identity," as used herein, refers to the percentage of nucleic acid residues in one sequence that are identical with the nucleic acid residues in another reference sequence after aligning the sequences and introducing gaps, if necessary, to achieve the maximum percent sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

Certain tools of statistical analysis (e.g., two-sided one-sample t-test, two-tailed Fisher's exact test) are referred to herein. In certain embodiments, modified statistical tools are referred to, which are described in detail herein.

As used herein, the term "subject" refers to an animal. Typically, the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. In embodiments, the subject is a male. As used herein, the term "male" refers to any animal that has male genitals (e.g., a penis), regardless of their genetic gender. In other embodiments, the subject is a female. As used herein, the term "female" refers to any animal that has female genitals (e.g., a vagina), regardless of their genetic gender.

As used herein, a subject is "in need of" a treatment if such subject would benefit biologically, medically or in quality of life from such treatment (preferably, a human).

A "reference" or "standard" may optionally be included in an assay, which provides a measure of a standard or known baseline level of a target molecule (e.g., "normal" level). In certain embodiments, a reference sample is a pool of samples (e.g., 2, 3, 4, 5, 6, 7, 8, 9, 10, or more samples combined) from healthy individuals (i.e., not having or suspected of having the disease of interest). In certain instances, a "test sample" and a "control sample" will be examined in an assay of the instant disclosure along with a reference sample. In these instances, the "test" and "control" samples may be collectively referred to as the "target samples" since they are being compared to a reference sample. When referring to the level of the one or more bacterial pathogen in a test sample, "elevated" compared to a control, as used herein, means a statistically significant increase in level. In certain embodiments, the level of bacterial pathogen(s) in a test sample is elevated compared to a control in a statistically significant manner. In further embodiments, the level of bacterial pathogen(s) in a test sample is increased in a statistically significant manner. For example, the difference between test and control levels may be about 2-fold, about 2.5-fold, about 3-fold, about 3.5-fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, about 10-fold, about 15-fold, about 20-fold, about 30-fold, or more. In certain instances, a statistically significant difference includes when a bacterial pathogen(s is present in a test sample but is absent or undetectable in the control.

As used herein, "statistically significant" refers to a p value of 0.050 or less when calculated using the Students t-test and indicates that it is unlikely that a particular event or result being measured has arisen by chance.

Unless the context requires otherwise, throughout the present specification and claims, the word "comprise" and variations thereof, such as, "comprises" and "comprising," "as well as synonymous terms like "include" and "have" and variants thereof, are to be construed in an open, inclusive sense; that is, as "including, but not limited to," such that recitation of items in a list is not to the exclusion of other like items that may also be useful in the materials, compositions, devices, and methods of this technology. Although the open-ended term "comprising," as a synonym of terms such as including, containing, or having, is used herein to describe and claim the invention, the present technology, or embodiments thereof, may alternatively be described using more limiting terms such as "consisting of" or "consisting essentially of" the recited ingredients. As used herein, the term "about" means±20%, ±10%, ±5% or ±1% of the indicated range, value, or structure, unless otherwise indicated. In embodiments, the terms "about" and "consisting essentially of" mean ±20% of the indicated range, value, or structure, unless otherwise indicated.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

Unless defined otherwise, all technical and scientific terms herein have the same meaning as commonly understood by one of ordinary skill in the art to which this invention belongs.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Similarly, the terms "can" and "may" and their variants are intended to be non-limiting, such that recitation that an embodiment can or may comprise certain elements or features does not exclude other embodiments of the present technology that do not contain those elements or features. Furthermore, the particular features, structures, or characteristics may be combined in any suitable manner in one or more embodiments.

The use of the words "optional" or "optionally" means that the subsequently described event or circumstances may or may not occur, and that the description includes instances where the event or circumstance occurs and instances in which it does not.

In the following description, certain specific details are set forth in order to provide a thorough understanding of various embodiments of this disclosure. However, one skilled in the art will understand that the disclosure may be practiced without these details.

Methods of Detecting and/or Classifying an Infection or a Risk of Infection

Described herein are methods of detecting and classifying an infection in a subject comprising detecting a pathogen in a genitourinary microbiome sample from the subject. Additionally, described herein are methods of classifying a risk of infection in a subject comprising detecting a pathogen in a genitourinary microbiome sample from the subject.

As is understood, any suitable method of detecting the pathogen may be used. A number of assays for detection and/or amplification of nucleotide sequences are well known in the art. Suitable methods include, for example, PCR, qPCR, southern blotting, in situ hybridization, whole genome sequencing, or next-generation sequencing. Additionally, a wide variety of labeling and conjugation techniques are known in the art that are used in various nucleic acid detection and amplification assays. Methods for producing labeled hybridization probes and/or PCR or other ligation primers for detecting and/or amplifying nucleotide sequences can include, for example, oligolabeling, nick translation and end-labeling, as well as other well known methods. Alternatively, nucleotide sequences of this invention can be cloned into a plasmid or vector for detection and amplification. Such plasmids and vectors are well known in the art and are commercially available. It is also contemplated that the methods of this invention can be conducted using a variety of commercially-available kits (e.g., Pharmacia & Upjohn; Promega; U.S. Biochemical Corp.). Suitable reporter molecules or labels, which can be used for ease of detection, include, for example, radionuclides, enzymes, fluorescence agents, chemiluminescence agents and chromogenic agents, as well as substrates, cofactors, inhibitors, magnetic particles and the like, as are well known in the art.

In embodiments, the pathogen may be detected using a suitable nucleic acid amplification process. The term "nucleic acid amplification process" or "nucleic acid amplification reaction" refers to any process or reaction for specifically amplifying (i.e., generating one or more copies of) a target nucleotide sequence, such as a DNA, a RNA, a or a cDNA, e.g., DNA from a pathogenic bacterium or a cell, such as a human cell. Numerous methods for amplifying nucleic acids are known, including various types of polymerase chain reaction (PCR; e.g., quantitative PCR such as QRT-PCR, ligation-mediated PCR, RT-PCR, amplified fragment length polymorphism, digital PCR, assembly PCR, touchdown PCR, nested PCR, multiplex PCR, and the like, which methods, related reagents, common reaction parameters, and common variations thereon, are known to those of ordinary skill in the art).

In some embodiments, the detecting the pathogen in the sample comprises PCR. PCR allows exponential amplification of short DNA sequences (usually 100 to 600 bases) within a longer double stranded DNA molecule. PCR entails the use of a pair of primers, each about 20 nucleotides in length, that are complementary to a defined sequence on each of the two complementary strands of the double stranded DNA. These primers are extended by a DNA polymerase so that a copy is made of the designated sequence, e.g., an amplicon. After making this copy, the same primers can be used again, not only to make another copy of the input DNA strand but also of the short copy made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 40) rounds of amplification, the PCR product is analyzed on an agarose gel and is abundant enough to be detected with an ethidium bromide stain.

In other embodiments, real-time PCR, also called quantitative real time PCR, quantitative PCR (Q-PCR/qPCR), or kinetic polymerase chain reaction, is a laboratory technique based on PCR, which is used to amplify and simultaneously quantify a targeted DNA molecule. qPCR enables both detection and quantification (as absolute number of copies or relative amount when normalized to DNA input or additional normalizing genes) of a specific sequence in a DNA sample. For example, in the embodiments disclosed herein, qPCR may be used to quantify the amount of DNA in a patient sample. The procedure follows the general principle of PCR; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce upon binding to complementary DNA (such as with molecular beacons) or with completion of each PCR cycle (such as with dual labeled probes rendered more fluorescent with the 5' exonuclease activity of polymerase enzymes).

In other embodiments, the detecting comprises southern blotting, in situ hybridization, whole genome sequencing, or next-generation sequencing.

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides.

The term "probe" or "primer" includes naturally occurring or recombinant or chemically synthesized single- and/or double-stranded nucleic acids. They can be labeled for detection by nick translation, Kienow fill-in reaction, PCR or other methods well known in the art. Probes and primers of the present invention, their preparation and/or labeling are described in Sambrook et al. 1989. Molecular Cloning: A Laboratory Manual, Cold Spring Harbor Laboratory, NY and Ausubel et al. 1989. Current Protocols in Molecular Biology, John Wiley & Sons, New York N.Y., both of which are incorporated herein by reference in their entirety for these teachings.

Primers, as used herein, are capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. Primers typically include at least one region of sequence that is complementary (i.e., partially or fully) to a region of a target sequence to be amplified, and in some cases are perfectly complementary to a region of a target sequence over their (primer's) full length.

A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleotide sequence at the 5' end which does not hybridize to the target nucleic acid, but which facilitates cloning of the amplified product. The region of the primer which is sufficiently complementary to the template to hybridize is referred to herein as the hybridizing region.

A "primer set" refers to a specific combination of a forward primer and a reverse primer. As used herein, a "forward primer" is understood to mean a primer that is capable of hybridizing to a region of DNA along the 5' (coding) strand of DNA. A "reverse" primer is understood to mean a primer that is capable of hybridizing to a region of DNA along the 3' (non-coding) strand of DNA. In various embodiments a primer set can be targeted to a nucleic acid sequence on a chromosome. In further embodiments a primer set can be targeted to a nucleic acid sequence that is extrachromosomal.

The "primer set" may be used in a PCR reaction to generate a specific PCR product or amplicon. The term "amplicon" as used herein, refers to the DNA sequence generated by a PCR or qPCR reaction.

The terms "target, "target sequence", "target region", and "target nucleic acid," as used herein, are synonymous and refer to a region or subsequence of a nucleic acid which is to be amplified or detected.

The term "hybridization" as used herein refers to any process by which a first strand of nucleic acid binds with a second strand of nucleic acid through base pairing. Hybridization can occur between fully complementary nucleic acid strands or between "substantially complementary" nucleic acid strands that contain minor regions of mismatch.

Nucleic acids can be detected by DNA-DNA or DNA-RNA hybridization or amplification using probes, primers and/or fragments of polynucleotides encoding the polypeptides and/or fragments of this invention and/or designed to detect and/or amplify the nucleic acids of this invention. For example, primers may be designed by performing a multiple sequence alignment of DNA from the organisms of interest and finding regions where sequences are shared by the group of organisms that are to be detected, but differ from organism outside the group. These primers are then specific for the taxon being detected.

As used herein, a primer is "specific," for a target sequence if, when used in an amplification reaction under sufficiently stringent conditions, the primer hybridizes primarily only to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in most cases. Hybridization conditions can be chosen under which the primer can form stable duplexes only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

Conditions under which only fully complementary nucleic acid strands will hybridize are referred to as "stringent hybridization conditions" or "sequence-specific hybridization conditions". The term "stringent" as used herein refers to hybridization conditions that are commonly understood in the art to define the conditions of the hybridization procedure. Stringency conditions can be low, high or medium, as those terms are commonly known in the art and well recognized by one of ordinary skill. In various embodiments, stringent conditions can include, for example, highly stringent (i.e., high stringency) conditions (e.g., hybridization to filter-bound DNA in 0.5 M NaHPO$_4$, 7% sodium dodecyl sulfate (SOS), 1 mM EDTA at 65° C., and washing in 0.1×SSC/0.1% SOS at 68° C.), and/or moderately stringent (i.e., medium stringency) conditions (e.g., washing in 0.2×SSC/0.1% SOS at 42° C.).

Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides.

It is understood in the art that a nucleic acid molecule need not be 100% complementary to a target nucleotide sequence to be specifically hybridizable. That is two or more nucleic acid molecules may be less than fully complementary and is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing 5 of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "hybridization complex" as used herein refers to a complex formed between two nucleotide sequences by virtue of the formation of hydrogen bonds between complementary G and C bases and between complementary A and T bases; these hydrogen bonds may be further stabilized by base stacking interactions. The two complementary nucleotide sequences hydrogen bond in an antiparallel configuration. A hybridization complex may be formed in solution (e.g., Cot or Rot analysis) or between one nucleotide sequence present in solution and another nucleotide sequence immobilized on a solid support (e.g., paper, membranes, filters, chips, pins or glass slides, or any other appropriate substrate to which cells and/or nucleic acids have been fixed).

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTPs, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the disclosure.

Nongonococcal Urethritis

Embodiments of the present disclosure include methods of detecting and classifying a nongonococcal urethritis (NGU) infection comprising detecting a pathogen in a urethral sample from the subject. In embodiments, the subject is a male.

Urethritis is an infection of the urethra. Infectious urethritis is usually classified into two categories: gonococcal urethritis (GU), caused by gonorrhea, and NGU, which is not caused by gonorrheal infection. Previously characterized causes of NGU include *Chlamydia trachomatis; Mycoplasma genitalium; Trichomonas vaginalis*; Adenovirus; Herpes simplex virus (HSV)-1; and HSV-2.

Any suitable urethral sample may be used. In embodiments, the urethral sample is a urine sample. In other embodiments, the urethral sample is from a penile or urethral swab. In other embodiments the urethral sample is penile discharge.

In embodiments, the pathogen comprises *Haemophilus influenzae, Mycoplasma penetrans*, or both. Accordingly, methods of the present disclosure include methods of detecting and classifying a nongonococcal urethritis (NGU) infection in a male subject comprising detecting a pathogen in a urethral sample from the male subject, the pathogen comprising *Haemophilus influenzae, Mycoplasma penetrans*, or both. In particular embodiments, the pathogen comprises *Haemophilus influenzae*. In particular embodiments, the pathogen comprises *Mycoplasma penetrans*. In specific embodiments, the pathogen comprises *Haemophilus influ-* enzae and *Mycoplasma penetrans*. In various embodiments, detecting the pathogen in the sample comprises determining a concentration of the pathogen in the sample.

In various embodiments, detecting the pathogen in the sample comprises carrying out a PCR on the sample. In some embodiments, detecting the pathogen in the sample comprises carrying out a polymerase chain reaction (PCR) on the sample with a primer set that hybridizes to nucleotide sequences of *Haemophilus influenzae* or *Mycoplasma penetrans* to generate a *Haemophilus influenzae* or *Mycoplasma penetrans* specific amplicon. In particular embodiments, methods of the disclosure further comprise contacting the *Haemophilus influenzae* or *Mycoplasma penetrans* specific amplicon with a first probe capable of hybridizing to the *Haemophilus influenzae* or *Mycoplasma penetrans* specific amplicon.

In some embodiments, the detecting comprises southern blotting, in situ hybridization, whole genome sequencing, or next-generation sequencing.

In various embodiments, detecting the pathogen in the sample comprises determining a concentration of the pathogen in the sample. In some embodiments, determining the concentration of the pathogen in the sample comprises carrying out a quantitative PCR on the sample with a primer set that hybridizes to nucleotide sequences of *Haemophilus influenzae* or *Mycoplasma penetrans* to generate a *Haemophilus influenzae* or *Mycoplasma penetrans* specific amplicon. In further embodiments, methods of the present disclosure further comprise contacting the *Haemophilus influenzae* or *Mycoplasma penetrans* specific amplicon with a second probe capable of hybridizing to the *Haemophilus influenzae* or *Mycoplasma penetrans* specific amplicon. In other embodiments, determining a concentration of the pathogen in the sample comprises next-generation sequencing.

In embodiments, the nucleic acid sequences are in a genome. In embodiments, the nucleotide sequences are in a ribosomal RNA (rRNA) gene. In some embodiments, the nucleotide sequences are in the chaperonin-60 gene (cpn60), or RNA polymerase b gene (rpoB). In some embodiments, the nucleotide sequences are in a small subunit 16S rRNA gene. In some embodiments, the nucleotide sequences are in a large subunit 23S rRNA gene. In particular embodiments, the nucleotide sequences are in a variable region of the 16S rRNA gene. In certain embodiments, the nucleotide sequences are in a variable region of the 23S rRNA gene. In other embodiments, the nucleic acid sequences are in an RNA. In specific embodiments, the RNA corresponds to a 16S rRNA gene. In particular embodiments, the RNA corresponds to a 23S rRNA gene. In various embodiments, the RNA corresponds to a variable region of the 16S rRNA gene. In various embodiments, the RNA corresponds to a variable region of the 23S rRNA gene.

In embodiments, the nucleotide sequences of the primer set are in a 16S rRNA gene of *Haemophilus influenzae* or *Mycoplasma penetrans*. In some embodiments, the nucleotide sequences of the primer set are in an 23S rRNA gene of *Haemophilus influenzae* or *Mycoplasma penetrans*. In some embodiments, the nucleotide sequences are in a variable region of a 16S rRNA gene of *Haemophilus influenzae* or *Mycoplasma penetrans*. In particular embodiments, the nucleotide sequences are in a variable region of an 23S rRNA gene of *Haemophilus influenzae* or *Mycoplasma penetrans*. In further embodiments, the variable region is a V3 region, a V4 region, or both, of the 16S rRNA. In certain embodiments, the variable region is a variable region of the 23S rRNA.

In particular embodiments, the pathogen is *Mycoplasma penetrans*, and the primer set includes primers with the following sequences:

```
                                         (SEQ ID NO: 1)
    Forward: 5'-CGGACGAAGCACTTGTGCTT-3'

(SEQ ID NO: 2)
    Reverse: 5'-TTTTCTCATGCGATAGTAATGTCC-3'
```

In embodiments, methods of the present disclosure further comprise contacting the *Mycoplasma penetrans* specific amplicon with a second probe capable of hybridizing to the *Mycoplasma penetrans* specific amplicon. In specific embodiments, the probe has the following sequence:

```
                                         (SEQ ID NO: 3)
    5'-TAACATACCTTTTAGTGGGGGATAACTGGTTG-3'
```

In particular embodiments, the pathogen is *Haemophilus influenzae*, and the primer set includes primers with the following sequences:

```
                                         (SEQ ID NO: 4)
    Forward: 5'-GCCCGTAGCTAACGTGATAAATCG-3'

(SEQ ID NO: 5)
    Reverse: 5'-AAGCTCATCTCTGAGCTCTTCTTAGG-3'
```

In embodiments, methods of the present disclosure further comprise contacting the *Haemophilus influenzae* ns specific amplicon with a second probe capable of hybridizing to the *Haemophilus influenzae* specific amplicon. In specific embodiments, the probe has the following sequence:

```
                                         (SEQ ID NO: 6)
    5'-CAAGCGGTGGAGCATGTGGTTTAATT-3'
```

In embodiments, methods of the present disclosure further comprise detecting and classifying the NGU infection in the male subject further comprises detecting and determining a concentration of *Lactobacillus iners, Atopobium vaginae, Veillonella atypica*, or a combination thereof, in the sample. In some embodiments, methods of the present disclosure further comprise detecting and determining the concentration of *Lactobacillus iners, Atopobium vaginae, Veillonella atypica*, or a combination thereof, in the sample comprises carrying out a quantitative PCR on the sample with a primer set that hybridizes to nucleotide sequences of *Lactobacillus iners, Atopobium vaginae, Veillonella atypica*, or a combination thereof, to generate a *Lactobacillus iners, Atopobium vaginae*, or *Veillonella atypica* specific amplicon. In various embodiments, methods of the present disclosure further comprise contacting the *Lactobacillus iners, Atopobium vaginae*, or *Veillonella atypica* specific amplicon with a third probe capable of hybridizing to the *Lactobacillus iners, Atopobium vaginae*, or *Veillonella atypica* specific amplicon. In some embodiments, detecting and determining a concentration of the pathogen in the sample comprises next-generation sequencing.

In some embodiments, classifying the NGU infection is based at least in part on a concentration of *Lactobacillus iners, Atopobium vaginae*, or *Veillonella atypica* being at least a threshold level. In other embodiments, classifying the NGU infection is based at least in part on a concentration of *Lactobacillus iners, Atopobium vaginae*, or *Veillonella atypica* being below a threshold level.

In some embodiments, classifying the NGU infection is based at least in part on a ratiometric comparison of the concentration of any of the following: *Lactobacillus iners, Atopobium vaginae, Veillonella atypica, Haemophilus influenzae, Mycoplasma penetrans, Chlamydia trachomatis, Mycoplasma genitalium, Trichomonas vaginalis*, Adenovirus, Herpes simplex virus (HSV)-1, or HSV-2.

In some embodiments, wherein the ratiometric comparison shows that bacterial positively associated with NGU or GU are higher in concentration than those negatively associated or non-associated with NGU or GU.

In various embodiments, detecting and classifying the NGU infection in the male subject further comprises detecting a known pathogen in the sample, the known pathogen comprising *Chlamydia trachomatis; Mycoplasma genitalium; Trichomonas vaginalis*; Adenovirus; Herpes simplex virus (HSV)-1; HSV-2; or a combination thereof. In some such embodiments, detecting the known pathogen in the sample comprises carrying out a PCR on the sample with a primer set that hybridizes to nucleotide sequences in the known pathogen to generate a known pathogen specific amplicon. In some embodiments, methods of the present disclosure further comprise contacting the known pathogen specific amplicon with a third probe capable of hybridizing to the known pathogen specific amplicon. In some embodiments, the detecting comprises southern blotting, in situ hybridization, whole genome sequencing, or next-generation sequencing.

In further embodiments, classifying the NGU infection in the male subject further comprises determining a concentration of the known pathogen. In some embodiments, determining the concentration of the known pathogen in the sample comprises carrying out a quantitative PCR on the sample with a primer set that hybridizes to nucleotide sequences in the known pathogen to generate a known pathogen specific amplicon. In some embodiments, methods of the disclosure further comprise contacting the known pathogen specific amplicon with a third probe capable of hybridizing to the known pathogen specific amplicon. In some embodiments, classifying the NGU infection is based at least in part on a concentration of the known pathogen being at least a threshold level. In some embodiments, determining a concentration of the pathogen in the sample comprises next-generation sequencing.

In certain embodiments, provided herein are methods of monitoring progression or recurrence of a NGU infection in a male subject, comprising detecting the level of the known pathogen in a sample from a human subject that has received at least one treatment for NGU and comparing the expression of the pathogen to a control or baseline sample, wherein the level of the pathogen in the sample is measured by detecting the amount of pathogen in the sample by detecting or hybridizing to the known pathogen specific amplicon. In some embodiments, the detecting comprises southern blotting, in situ hybridization, whole genome sequencing, or next-generation sequencing.

In another aspect, the present invention provides kits comprising materials useful for carrying out diagnostic methods according to the present invention. The diagnosis procedures described herein may be performed by diagnostic laboratories, experimental laboratories, or practitioners. The invention provides kits, which can be used in these different settings. Materials and reagents for characterizing biological samples and diagnosing a NGU in a subject according to the methods herein may be assembled together in a kit. In certain aspects, a kit comprises at least one reagent that specifically detects levels of one or more pathogen disclosed herein, and instructions for using the kit according to a method of this disclosure.

Each kit may preferably include the reagent (e.g., specific primers and/or probes) that renders the procedure specific. Thus, for detecting/quantifying a pathogen, the reagent that specifically detects levels of the pathogen may be a set of primers and/or probe that specifically binds to the pathogen of interest. A kit of the present disclosure may further comprise one or more reagents, plastic tubes, and control samples.

Protocols for using these buffers and reagents for performing different steps of the procedure may be included in the kit. The reagents may be supplied in a solid (e.g., lyophilized) or liquid form. The kits of the present disclosure may optionally comprise different containers (e.g., slide, vial, ampoule, test tube, flask or bottle) for each individual buffer or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, kits of the present disclosure further include control samples. Instructions for using the kit, according to one or more methods of this disclosure, may comprise instructions for processing the biological sample obtained from a subject, or for performing the test, instructions for interpreting the results. As well as a notice in the form prescribed by a governmental agency (e.g., FDA) regulating the manufacture, use or sale of pharmaceuticals or biological products.

Human Immunodeficiency Virus

Embodiments of the present disclosure include methods of classifying a risk of human immunodeficiency virus (HIV) infection in a subject comprising detecting a pathogen in a vaginal sample from the subject. In embodiments, the HIV is HIV-1, HIV-2, or both. In some embodiments, the HIV is HIV-1. In other embodiments, the HIV is HIV-2.

Any suitable vaginal sample may be used. In embodiments, the vaginal sample is a vaginal irrigation. In other embodiments, the vaginal sample is from a vaginal swab.

In embodiments, the pathogen comprises Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof. Accordingly, methods of the present disclosure comprise classifying a risk of human immunodeficiency virus (HIV) infection in a subject comprising detecting a pathogen in a vaginal sample from the subject, the pathogen comprising BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof.

In embodiments, the pathogen comprises BVAB2, vaginal TM7 species type 1, *Peptoniphilus lacrimalis, Porphyromo-* nas species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, or a combination thereof. Accordingly, methods of the present disclosure comprise classifying a risk of human immunodeficiency virus (HIV) infection in a subject comprising detecting a pathogen in a vaginal sample from the subject, the pathogen comprising BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, or a combination thereof. In some embodiments, the pathogen comprises BVAB2, vaginal TM7 species type 1, *Peptoniphilus lacrimalis*, *Porphyromonas* species type 1, or a combination thereof.

In further embodiments, detecting the pathogen (e.g., BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2, or a combination thereof) in the vaginal sample comprises carrying out PCR on the vaginal sample with a primer set that hybridizes to nucleotide sequences of the pathogen to generate a pathogen specific amplicon. In some embodiments, a method of the disclosure further comprises contacting the pathogen specific amplicon with a first probe capable of hybridizing to the pathogen species specific amplicon. In some embodiments, the detecting comprises southern blotting, in situ hybridization, whole genome sequencing, or next-generation sequencing.

In further embodiments, detecting the pathogen in the vaginal sample comprises carrying out PCR on the vaginal sample with a primer set that hybridizes to nucleotide sequences of BVA32, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2, or a combination thereof to generate a BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon. In some embodiments, a method of the disclosure further comprises contacting the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon with a first probe capable of hybridizing to the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon. In some embodiments, the detecting comprises southern blotting, in situ hybridization, whole genome sequencing, or next-generation sequencing.

In further embodiments, detecting the pathogen in the vaginal sample comprises carrying out PCR on the vaginal sample with a primer set that hybridizes to nucleotide sequences of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, or a combination thereof to generate a BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon. In some embodiments, a method of the disclosure further comprises contacting the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon with a first probe capable of hybridizing to the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon. In some embodiments, the detecting comprises southern blotting, in situ hybridization, whole genome sequencing, or next-generation sequencing.

In embodiments, detecting the pathogen in the vaginal sample comprises determining a concentration of the pathogen in the sample. In some embodiments, determining the concentration of the pathogen in the vaginal sample comprises carrying out a quantitative PCR on the sample with a primer set that hybridizes to nucleotide sequences of the pathogen (e.g., BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2, or a combination thereof), or a combination thereof, to generate a pathogen specific amplicon. In some embodiments, a method of the disclosure further comprises contacting the pathogen specific amplicon with a third probe capable of hybridizing to the pathogen specific amplicon. In some embodiments, classifying the risk of HIV infection is based at least in part on a concentration of the pathogen being at least a threshold level. In some embodiments, determining a concentration of the pathogen in the sample comprises next-generation sequencing.

In embodiments, detecting the pathogen in the vaginal sample comprises determining a concentration of the pathogen in the sample. In some embodiments, determining the concentration of the pathogen in the vaginal sample comprises carrying out a quantitative PCR on the sample with a primer set that hybridizes to nucleotide sequences of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof, to generate a BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1 specific amplicon. In some embodiments, a method of the disclosure further comprises contacting the BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1 specific amplicon with a third probe capable of hybridizing to the BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1 specific amplicon. In some embodiments, classifying the risk of HIV infection is based at least in part on a concentration of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof being at least a threshold level. In some embodiments, determining a concentration of the pathogen in the sample comprises next-generation sequencing.

In embodiments, the nucleic acid sequences are in a genome. In embodiments, the nucleotide sequences are in a ribosomal RNA (rRNA) gene. In some embodiments, the nucleotide sequences are in the chaperonin-60 gene (cpn60 gene), or RNA polymerase b gene (rpoB). In some embodiments, the nucleotide sequences are in a 16S rRNA gene. In some embodiments, the nucleotide sequences are in an 23S rRNA gene. In particular embodiments, the nucleotide sequences are in a variable region of the 16S rRNA gene. In certain embodiments, the nucleotide sequences are in a variable region of the 23S rRNA gene. In other embodiments, the nucleic acid sequences are in an RNA. In specific embodiments, the RNA corresponds to a 16S rRNA gene. In particular embodiments, the RNA corresponds to an 23S rRNA gene. In various embodiments, the RNA corresponds to a variable region of the 16S rRNA gene. In various embodiments, the RNA corresponds to a variable region of the 23S rRNA gene.

In embodiments, the nucleotide sequences are in a 16S rRNA gene of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof. In embodiments, the nucleotide sequences are in a 16S rRNA gene of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof. In further embodiments, the nucleotide sequences are in a variable region of a 16S rRNA gene of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof. In further embodiments, the nucleotide sequences are in a variable region of a 16S rRNA gene of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof. In still further embodiments, the variable region is a V3 region, a V4 region, or both, of the 16S rRNA.

In some embodiments, the nucleotide sequences are in a 23S rRNA gene of BVAB2, vaginal TM7 species type 1, *Peptoniphilus lacrimalis, Porphyromonas* species type 1, *Bulleidia* species type 1, *Fusobacterium equinum, Fusobacterium* gonidiaformans, *Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof. In some embodiments, the nucleotide sequences are in a 23S rRNA gene of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof. In some further embodiments, the nucleotide sequences are in a variable region of a 23S rRNA gene of BVA32, vaginal TM7 species type 1, *Peptoniphilus lacrimalis, Porphyromonas* species type 1, *Bulleidia* species, *Fusobacterium equinum, Fusobacterium gonidiaformans, Porphyromonas asaccharolytica, Porphyromonas uenonis*, uncultivated Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof. In some further embodiments, the nucleotide sequences are in a variable region of a 23S rRNA gene of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, uncultivated Bacteroidales species type 1, or a combination thereof. In still some further embodiments, the variable region is a region of the 23S rRNA.

In particular embodiments, suitable primers sets, probes, conditions, cycling/Taq concentrations, and 16S rRNA sequences (as well as related accession numbers) are shown in Table 1.

In various embodiments, the nucleotide sequences are of BVAB2, vaginal TM7 species type 1, *Peptoniphilus lacrimalis, Porphyromonas* species type 1, or a combination thereof. In some embodiments, classifying the HIV infection in the subject further comprises detecting and determining a concentration of *Lactobacillus crispatus* in the sample.

In some embodiments, classifying the risk of HIV infection is based at least in part on a concentration of *Lactobacillus crispatus* being at least a threshold level. In other embodiments, classifying the risk of HIV infection is based at least in part on a concentration of *Lactobacillus crispatus* being below a threshold level.

In some embodiments, classifying the HIV infection in the subject further comprises detecting a further pathogen in the sample, the pathogen further comprising *Eggerthella*-like species type 1; *Gemella asaccharolytica; Sneathia sanguinegens; Mycoplasma hominis; Prevotella bivia; Megasphaera* species type 2; *Parvimonas* species type 2; or a combination thereof. In particular embodiments, the further pathogen comprises *Gemella asaccharolytica; Sneathia sanguinegens; Mycoplasma hominis; Prevotella bivia; Eggerthella*-like species type 1; *Megasphaera* species type 2; *Parvimonas* species type 2; or a combination thereof. In further embodiments, classifying the HIV infection in the subject further comprises determining a concentration of the further pathogen. In some embodiments, classifying the risk of HIV infection is based at least in part on a concentration of the further pathogen being at least a threshold level.

Methods of Treating an Infection

Described herein are methods of treating (e.g., preventing) an infection in a subject. As used herein, the term "treat", "treating" or "treatment" of any disease or disorder refers the treatment of the disease or disorder in a subject (e.g., a mammal), particularly in a human, and include: (a) ameliorating the disease or disorder, (i.e., slowing or arresting or reducing the development of the disease or disorder, or at least one of the clinical symptoms thereof); (b) relieving or modulating the disease or disorder, (i.e., causing regression of the disease/disorder), either physically, (e.g., stabilization of a discernible symptom), physiologically, (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a subject (e.g., a mammal), in particular, when such a subject (e.g., a mammal) is exposed to the disease but has not yet been diagnosed as having it. As used herein, the term "treatment" refers to both therapeutic treatment and prophylactic or preventative measures. Those in need of treatment include those already with the disease or disorder as well as those in which the disease or disorder is to be prevented. In embodiments, preventing a disease or disorder comprises reducing the risk of acquiring a disease or disorder. In embodiments, the risk of acquiring a disease or disorder in a treated subject is reduced by 5%, 10%, 15%, 20%, 25%, 30%, 35%, 40%, 45%, 50%, 55%, 60%, 65%, 70%, 75%, 80%, 85%, 90%, 95% or more as compared to an untreated subject.

The term "an effective amount" of a composition of the present disclosure refers to an amount of the composition of the present disclosure that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "an effective amount" refers to the amount of the composition of the present disclosure that, when administered to a subject, is effective to (1) at least partially alleviate, inhibit, prevent and/or ameliorate a condition, or a disorder or a disease (e.g., NGU, HIV, etc.); or (2) reducing or inhibiting an associated pathogen.

In another embodiment, the term "effective amount" refers to the amount of the composition of the present disclosure that, when administered to a cell, or a tissue, or a non-cellular biological material, or a medium, is effective to at least partially reduce or inhibit an associated pathogen, or reduce symptoms of the disease or condition.

The effective amount can vary depending on such factors as the size and weight of the subject, the type of illness, or the particular composition of the present disclosure. One of ordinary skill in the art would be able to study the factors contained herein and make the determination regarding the effective amount of the compositions of the present disclosure without undue experimentation.

The regimen of administration can affect what constitutes an effective amount. The composition of the present disclosure can be administered to the subject either prior to or after the onset of a disease, disorder or condition. Further, several divided dosages, as well as staggered dosages, can be administered daily or sequentially, or the dose can be continuously infused, or can be a bolus injection. Further, the dosages of the composition(s) of the present disclosure can be proportionally increased or decreased as indicated by the exigencies of the therapeutic or prophylactic situation.

Nongonococcal Urethritis

In embodiments, methods of detecting and classifying a nongonococcal urethritis (NGU) infection further comprise selecting a therapeutic agent to administer to the male subject based at least on the detecting and classifying. In yet further embodiments, the methods of detecting and classifying the NGU infection further comprise administering an effective amount of the therapeutic agent to the subject.

Accordingly, embodiments of methods of the present disclosure comprise a method for treating a NGU infection in a male subject in need thereof, the method comprising: administering an effective amount of a therapeutic agent to the male subject, the NGU infection having been classified by an in vitro method comprising: detecting a pathogen in a urethral sample from the male subject, the pathogen comprising *Haemophilus influenzae, Mycoplasma penetrans*, or both.

In embodiments, the pathogen detected is *Haemophilus influenzae*. In some such embodiments the therapeutic agent is an antibacterial agent with activity against *Haemophilus influenzae*.

In other embodiments, the pathogen detected is *Mycoplasma penetrans*. In some such embodiments, the male subject is a man who has sex with men. In a further embodiment, the therapeutic agent is an antibacterial agent with activity against *Mycoplasma penetrans*.

In embodiments, the pathogen detected is *Haemophilus influenzae* and *Mycoplasma penetrans*. In some embodiments, the therapeutic agent is an antibacterial agent with activity against *Haemophilus influenzae* and *Mycoplasma penetrans*.

In particular embodiments, methods of the present disclosure include methods for preventing a disease or disorder. Accordingly, embodiments of methods of the present disclosure include a method for preventing a NGU infection in a male subject in need thereof, the method comprising: administering an effective amount of a therapeutic agent to the male subject, the NGU infection having been classified by an in vitro method comprising: detecting a pathogen in a urethral sample from the male subject, the pathogen comprising *Haemophilus influenzae, Mycoplasma penetrans*, or both.

As is understood by one of skill in the art, any suitable therapeutic agent can be administered to the subject. For example, in various embodiments, the therapeutic agent has activity against a pathogen comprising *Haemophilus influenzae, Mycoplasma penetrans*, or both. In some embodiments, a therapeutic agent does not have activity against helpful bacteria (e.g., bacteriostatic or bacteriocidal activity). In particular embodiments, the therapeutic agent does not have activity against *Lactobacillus iners, Atopobium vaginae, Veillonella atypica*, or a combination thereof. In some embodiments, the therapeutic agent can consist of, ceftriaxone, doxycycline, ciprofloxacin, or levofloxacin, azithromycin, or other antibiotics that target either *H. influenzae* or *M. penetrans*.

Human Immunodeficiency Virus

In embodiments, methods of classifying a risk of HIV infection in a subject further comprise selecting a therapeutic agent to administer to the subject based at least on the classifying. In yet further embodiments, the methods of classifying the risk of HIV infection further comprise administering an effective amount of the therapeutic agent to the subject.

In embodiments, methods of the present disclosure comprise a method for preventing an HIV infection in a subject in need thereof, the method comprising: administering an effective amount of a therapeutic agent, the HIV infection having been classified by an in vitro method comprising: detecting a pathogen in a vaginal sample from the subject, the pathogen comprising Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof.

In particular embodiments, methods of the present disclosure include methods for preventing a disease or disorder. Accordingly, embodiments of methods of the present disclosure include a method for preventing a human immunodeficiency virus (HIV) infection in a subject in need thereof, the method comprising: administering an effective amount of a therapeutic agent, the HIV infection having been classified by an in vitro method comprising: detecting a pathogen in a vaginal sample from the subject. In embodiments, the pathogen comprises BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof. In further embodiments, the pathogen comprises Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof.

In embodiments, the therapeutic agent has activity against the pathogen. In further embodiments, the therapeutic agent has activity against the further pathogen. In some embodiments, the therapeutic agent does not have activity against *Lactobacillus crispatus*.

In embodiments, the therapeutic agent comprises a nitroimidazole antibiotic. In some embodiments, the therapeutic agent comprises metronidazole, metrogel, or a combination thereof.

In some embodiments, treatment (e.g., prevention) of the HIV infection comprise vaginal bacteriotherapy. In such embodiments, the subject's natural microbiome may be reduced and a vaginal microbiome preparation may be introduced on or in the vagina of the subject. Thus, in some embodiments, methods of treatment comprise introducing a vaginal microbiome preparation on or in the vagina of the subject. A vaginal microbiome preparation would contain bacteria from a healthy vaginal microbiome for transplantation. In various embodiments, a urethral microbiome preparation comprises at least one of species of healthy bacteria (e.g., *Lactobacillus crispatus*).

Kits

The present disclosure further provides for kits for use in detecting and classifying an infection or a risk of infection in a subject as described herein. Kits of the present disclosure comprise a primer set and a probe. The primer set and/or probe may be provided in a composition. Such compositions comprise a primer set and/or probe as described above and a carrier. Suitable carriers include those that maintain the stability and integrity of the primer set and/or probe. Carriers may be a diluent, excipient, preservative, or solvent.

The kits can further comprise written instructions for using the kit in the methods disclosed herein. In various embodiments, the written instructions may include instructions regarding preparation of the reagents; appropriate reference levels to interpret results associated with using the kit; proper disposal of the related waste; and the like. The written instructions can be in the form of printed instructions provided within the kit, or the written instructions can be printed on a portion of the container housing the kit. Written instructions may be in the form of a sheet, pamphlet, brochure, CD-ROM, or computer-readable device, or can provide directions to locate instructions at a remote location, such as a website. The written instructions may be in English and/or in a national or regional language.

Such kits can further comprise one or more additional reagents, assay controls, or other supplies necessary for evaluation of a sample, such as welled plates, syringes, ampules, vials, tubes, tubing, facemask, a needleless fluid transfer device, an injection cap, sponges, sterile adhesive strips, Chloraprep, gloves, and the like. In certain embodiments, the kits described herein do not include a cell permeabilization agent, such as digitonin. Variations in contents of any of the kits described herein can be made. In various embodiments, the profiling peptide and detecting agent, optionally with one or more reagents or supplies, are combined into a compact container, optionally with written instructions for use.

Nongonococcal Urethritis

In embodiments, a kit for detecting and classifying a NGU infection in a male subject, the kit comprising: a first primer set that hybridizes to first nucleotide sequences of *Haemophilus influenzae* or *Mycoplasma penetrans* to generate a *Haemophilus influenzae* or *Mycoplasma penetrans* specific amplicon; and a first probe capable of hybridizing to the *Haemophilus influenzae* or *Mycoplasma penetrans* specific amplicon.

In embodiments, the first nucleotide sequences are of *Haemophilus influenzae*, and first probe is capable of hybridizing to the *Haemophilus influenzae* specific amplicon. In some embodiments, a kit further comprises a second primer set that hybridizes to second nucleotide sequences of *Mycoplasma penetrans* to generate a *Mycoplasma penetrans* specific amplicon; and a second probe capable of hybridizing to the *Mycoplasma penetrans* specific amplicon.

In further embodiments, the first nucleotide sequences are of *Mycoplasma penetrans*, and first probe is capable of hybridizing to the *Mycoplasma penetrans* specific amplicon. In particular embodiments, a kit comprises a second primer set that hybridizes to second nucleotide sequences of *Haemophilus influenzae* to generate a *Haemophilus influenzae* specific amplicon; and a second probe capable of hybridizing to the *Haemophilus influenzae* specific amplicon.

In embodiments, the nucleic acid sequences are in a genome. In some embodiments, the nucleotide sequences are in a 16S rRNA gene. In some embodiments, the nucleotide sequences are in an 23S rRNA gene. In particular embodiments, the nucleotide sequences are in a variable region of the 16S rRNA gene. In certain embodiments, the nucleotide sequences are in a variable region of the 23S rRNA gene. In other embodiments, the nucleic acid sequences are in an RNA. In specific embodiments, the RNA corresponds to a 16S rRNA gene. In particular embodiments, the RNA corresponds to a 23S rRNA gene. In various embodiments, the RNA corresponds to a variable region of the 16S rRNA gene. In various embodiments, the RNA corresponds to a variable region of the 23S rRNA gene.

In various embodiments, the first nucleotide sequences are in a 16S ribosomal RNA (rRNA) gene of *Haemophilus influenzae* or *Mycoplasma penetrans*. In various other embodiments, the first nucleotide sequences are in a 23S ribosomal RNA (rRNA) gene of *Haemophilus influenzae* or *Mycoplasma penetrans*. In some embodiments, the first nucleotide sequences are in a variable region of a 16S rRNA gene of *Haemophilus influenzae* or *Mycoplasma penetrans*. In some other embodiments, the first nucleotide sequences are in a variable region of a 23S rRNA gene of *Haemophilus influenzae* or *Mycoplasma penetrans*. In some embodiments, the second nucleotide sequences are in a 16S ribosomal RNA (rRNA) gene of *Haemophilus influenzae* or *Mycoplasma penetrans*. In some other embodiments, the second nucleotide sequences are in a 16S ribosomal RNA (rRNA) gene of *Haemophilus influenzae* or *Mycoplasma penetrans*. In specific embodiments, the second nucleotide sequences are in a variable region of a 16S rRNA gene of *Haemophilus influenzae* or *Mycoplasma penetrans*. In certain embodiments, the second nucleotide sequences are in a variable region of a 23S rRNA gene of *Haemophilus influenzae* or *Mycoplasma penetrans*. In various embodiments, the variable region is a V3 region, a V4 region, or both, of the 16S rRNA. In various embodiments, the variable region is within the 23S rRNA gene.

In particular embodiments, the pathogen is *Mycoplasma penetrans*, and the primer set includes primers with the following sequences:

```
                                       (SEQ ID NO: 1)
     Forward: 5'-CGGACGAAGCACTTGTGCTT-3'

(SEQ ID NO: 2)
     Reverse: 5'-TTTTCTCATGCGATAGTAATGTCC-3'
```

In embodiments, methods of the present disclosure further comprise contacting the *Mycoplasma penetrans* specific amplicon with a second probe capable of hybridizing to the *Mycoplasma penetrans* specific amplicon. In specific embodiments, the probe has the following sequence:

```
                                       (SEQ ID NO: 3)
     5'-TAACATACCTTTTAGTGGGGGATAACTGGTTG-3'
```

In particular embodiments, the pathogen is *Haemophilus influenzae*, and the primer set includes primers with the following sequences:

```
                                       (SEQ ID NO: 4)
     Forward: 5'-GCCCGTAGCTAACGTGATAAATCG-3'

(SEQ ID NO: 5)
     Reverse: 5'-AAGCTCATCTCTGAGCTCTTCTTAGG-3'
```

In embodiments, methods of the present disclosure further comprise contacting the *Haemophilus influenzae* ns specific amplicon with a second probe capable of hybridizing to the *Haemophilus influenzae* specific amplicon. In specific embodiments, the probe has the following sequence:

```
                                       (SEQ ID NO: 6)
     5'-CAAGCGGTGGAGCATGTGGTTTAATT-3'
```

In embodiments, a kit further comprises a third primer set that hybridizes to third nucleotide sequences of *Lactobacillus iners, Atopobium vaginae, Veillonella atypica*, or a combination thereof to generate a *Lactobacillus iners, Atopobium vaginae*, or *Veillonella atypica* specific amplicon. In particular embodiments, a kit further comprises a third probe capable of hybridizing to the third amplicon.

In still embodiments, a kit further comprises a fourth primer set that hybridizes to nucleotide sequences of *Chlamydia trachomatis; Mycoplasma genitalium; Trichomonas vaginalis*; Adenovirus; Herpes simplex virus (HSV)-1; or HSV-2, to generate a *Chlamydia trachomatis; Mycoplasma genitalium; Trichomonas vaginalis*; Adenovirus; Herpes simplex virus (HSV)-1; or HSV-2 specific amplicon. In some embodiments, the kit comprises a fourth probe capable of hybridizing to the *Chlamydia trachomatis; Mycoplasma genitalium; Trichomonas vaginalis*; Adenovirus; HSV-1; or HSV-2 specific amplicon.

Human Immunodeficiency Virus

In embodiments, a kit for classifying a HIV infection in a subject, the kit comprising: a first primer set that hybridizes to first nucleotide sequences of a pathogen to generate a pathogen specific amplicon; and a first probe capable of hybridizing to the pathogen specific amplicon.

In some embodiments, a kit for classifying a HIV infection in a subject, the kit comprising: a first primer set that hybridizes to first nucleotide sequences of a pathogen comprising BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis*,

*Parvimonas* species type 2, or a combination thereof to generate a B3VAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 specific amplicon; and a first probe capable of hybridizing to the BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 specific amplicon.

In embodiments, a kit for classifying a HIV infection in a subject, the kit comprising: a first primer set that hybridizes to first nucleotide sequences of a pathogen comprising BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof, to generate a BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1 specific amplicon; and a first probe capable of hybridizing to the BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1 specific amplicon.

In embodiments, the nucleic acid sequences are in a genome. In some embodiments, the nucleotide sequences are in a 16S rRNA gene. In some embodiments, the nucleotide sequences are in a 23S rRNA gene. In particular embodiments, the nucleotide sequences are in a variable region of the 16S rRNA gene. In certain embodiments, the nucleotide sequences are in a variable region of the 23S rRNA gene. In other embodiments, the nucleic acid sequences are in an RNA. In specific embodiments, the RNA corresponds to a 16S rRNA gene. In particular embodiments, the RNA corresponds to a 23S rRNA gene. In various embodiments, the RNA corresponds to a variable region of the 16S rRNA gene. In various embodiments, the RNA corresponds to a variable region of the 23S rRNA gene.

In particular embodiments, suitable primers sets, probes, conditions, cycling/Taq concentrations, and 16S rRNA sequences (as well as related accession numbers) are shown in Table 1.

In embodiments, the first nucleotide sequences are in a 16S rRNA gene of the pathogen. In some embodiments, the first nucleotide sequences are in an 23S rRNA gene of the pathogen. In still further embodiments, the first nucleotide sequences are in a variable region of a 16S rRNA gene of the pathogen. In some further embodiments, the first nucleotide sequences are in a variable region of an 23S rRNA gene of the pathogen.

In some embodiments, a kit of the disclosure further comprises a plurality of primer sets, individual primer sets of the plurality of primer sets hybridize to respective nucleotide sequences of a pathogen comprising BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof, to generate a BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 specific amplicon, the plurality of primer sets comprising the first primer set; and a plurality of probes, individual probes of the plurality of probes being capable of hybridizing to the BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 specific amplicon.

In some embodiments, a kit of the disclosure further comprises a plurality of primer sets, individual primer sets of the plurality of primer sets hybridize to respective nucleotide sequences of a pathogen comprising BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof, to generate a BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1 specific amplicon, the plurality of primer sets comprising the first primer set; and a plurality of probes, individual probes of the plurality of probes being capable of hybridizing to the BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1 specific amplicon.

In various embodiments, the respective nucleotide sequences that hybridize to the individual primer sets of the plurality of primer sets are independently in a 16S rRNA gene or an 23S rRNA gene of the pathogen. In various embodiments, the respective nucleotide sequences that hybridize to the individual primer sets of the plurality of primer sets are independently in a 16S rRNA gene of the pathogen. In various embodiments, the respective nucleotide sequences that hybridize to the individual primer sets of the plurality of primer sets are independently in an 23S rRNA gene of the pathogen.

In embodiments, the respective nucleotide sequences that hybridize to the individual primer sets of the plurality of primer sets are independently in a variable region of a 16S rRNA gene of the pathogen. In some embodiments, the respective nucleotide sequences that hybridize to the individual primer sets of the plurality of primer sets are independently in a variable region of a 23S rRNA gene of the pathogen. In some embodiments, the variable region is a V3 region, a V4 region, or both, of the 16S rRNA. In some embodiments, the variable region is within the 23S rRNA gene.

In additional embodiments, a kit of the disclosure further comprises a second primer set that hybridizes to second nucleotide sequences of *Lactobacillus crispatus* to generate a *Lactobacillus crispatus* specific amplicon. In embodiments, a kit of the disclosure further comprises a second probe capable of hybridizing to the *Lactobacillus crispatus* specific amplicon.

In additional embodiments, a kit of the disclosure further comprises a third primer set that hybridizes to nucleotide sequences of *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon. In some embodiments, a kit of the disclosure further comprises a third probe capable of hybridizing to the *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon.

Various embodiments of the disclosure are described herein. It will be recognized that features specified in each embodiment may be combined with other specified features to provide further embodiments of the present disclosure. The following embodiments are included within the scope of the disclosure:

Embodiment 1. A method, comprising:
detecting and classifying a nongonococcal urethritis (NGU) infection in a male subject comprising detecting a pathogen in a urethral sample from the male subject, the pathogen comprising *Haemophilus influenzae*, *Mycoplasma penetrans*, or both.

Embodiment 2. The method of embodiment 1, further comprising selecting a therapeutic agent to administer to the male subject based on detecting the pathogen.

Embodiment 3. The method of embodiment 1 or 2, further comprising administering an effective amount of the therapeutic agent to the subject.

Embodiment 4. A method for treating or preventing a nongonococcal urethritis (NGU) infection in a male subject in need thereof, the method comprising:
administering an effective amount of a therapeutic agent to the male subject, the NGU infection having been classified by an in vitro method comprising:
detecting a pathogen in a urethral sample from the male subject, the pathogen comprising *Haemophilus influenzae*, *Mycoplasma penetrans*, or both.

Embodiment 5. A method for preventing a nongonococcal urethritis (NGU) infection in a male subject in need thereof, the method comprising:
administering an effective amount of a therapeutic agent to the male subject, the NGU infection having been classified by an in vitro method comprising:
detecting a pathogen in a urethral sample from the male subject, the pathogen comprising *Haemophilus influenzae*, *Mycoplasma penetrans*, or both.

Embodiment 6. The method of any one of embodiments 1-5, wherein the urethral sample is a urine sample.

Embodiment 7. The method of any one of embodiments 1-5, wherein the urethral sample is from a penile or urethral swab.

Embodiment 8. The method of any one of embodiments 1-7, wherein detecting the pathogen in the sample comprises carrying out a polymerase chain reaction (PCR) on the sample with a primer set that hybridizes to nucleotide sequences of *Haemophilus influenzae* or *Mycoplasma penetrans* to generate a *Haemophilus influenzae* or *Mycoplasma penetrans* specific amplicon.

Embodiment 9. The method of embodiment 8, further comprising contacting the *Haemophilus influenzae* or *Mycoplasma penetrans* specific amplicon with a first probe capable of hybridizing to the *Haemophilus influenzae* or *Mycoplasma penetrans* specific amplicon.

Embodiment 10 The method of any one of embodiments 1-9, wherein detecting the pathogen in the sample comprises determining a concentration of the pathogen in the sample.

Embodiment 11. The method of embodiment 10, wherein determining the concentration of the pathogen in the sample comprises carrying out a quantitative PCR on the sample with a primer set that hybridizes to nucleotide sequences of *Haemophilus influenzae* or *Mycoplasma penetrans* to generate a *Haemophilus influenzae* or *Mycoplasma penetrans* specific amplicon.

Embodiment 12. The method of embodiment 11, further comprising contacting the *Haemophilus influenzae* or *Mycoplasma penetrans* specific amplicon with a second probe capable of hybridizing to the *Haemophilus influenzae* or *Mycoplasma penetrans* specific amplicon.

Embodiment 13. The method of any one embodiments 8-12, wherein the nucleotide sequences are in a genome of *Haemophilus influenzae* or *Mycoplasma penetrans*.

Embodiment 14. The method of embodiment 13, wherein the nucleotide sequences are in a 16S ribosomal RNA (rRNA) gene of *Haemophilus influenzae* or *Mycoplasma penetrans*.

Embodiment 15. The method of embodiment 14, wherein the nucleotide sequences are in a variable region of the 16S rRNA gene of *Haemophilus influenzae* or *Mycoplasma penetrans*.

Embodiment 16. The method of any one embodiments 8-12, wherein the nucleotide sequences are in an RNA of *Haemophilus influenzae* or *Mycoplasma penetrans*.

Embodiment 17. The method of embodiment 16, wherein the RNA corresponds to a 16S rRNA gene of *Haemophilus influenzae* or *Mycoplasma penetrans*.

Embodiment 18. The method of embodiment 17, wherein the RNA corresponds to a variable region of the 16S rRNA gene of *Haemophilus influenzae* or *Mycoplasma penetrans*.

Embodiment 19. The method of embodiment 15 or 18, wherein the variable region is a V3 region, a V4 region, or both, of the 16S rRNA gene.

Embodiment 20. The method of any one of embodiments 1-7, wherein detecting the pathogen comprises southern blotting, in situ hybridization, whole genome sequencing, or next-generation sequencing.

Embodiment 21. The method of any one of embodiments 1-20, wherein detecting and classifying the NGU infection in the male subject further comprises detecting and determining a concentration of *Lactobacillus iners*, *Atopobium vaginae*, *Veillonella atypica*, or a combination thereof, in the sample.

Embodiment 22. The method of embodiment 21, wherein detecting and determining the concentration of *Lactobacil-*

*lus iners, Atopobium vaginae, Veillonella atypica*, or a combination thereof, in the sample comprises carrying out a quantitative PCR on the sample with a primer set that hybridizes to nucleotide sequences of *Lactobacillus iners, Atopobium vaginae*, or *Veillonella atypica*, to generate a *Lactobacillus iners, Atopobium vaginae*, or *Veillonella atypica* specific amplicon.

Embodiment 23. The method of embodiment 22, wherein the nucleotide sequences are in a genome of *Lactobacillus iners, Atopobium vaginae*, or *Veillonella atypica*.

Embodiment 24. The method of embodiment 22, wherein the nucleotide sequences are in an RNA of *Lactobacillus iners, Atopobium vaginae*, or *Veillonella atypica*.

Embodiment 25. The method of any one of embodiments 22-24, further comprising contacting the *Lactobacillus iners, Atopobium vaginae*, or *Veillonella atypica* specific amplicon with a third probe capable of hybridizing to the *Lactobacillus iners, Atopobium vaginae*, or *Veillonella atypica* specific amplicon.

Embodiment 26. The method of any one of embodiments 1-25, wherein detecting and classifying the NGU infection in the male subject further comprises detecting a known pathogen in the sample, the known pathogen comprising *Chlamydia trachomatis; Mycoplasma genitalium; Trichomonas vaginalis*; Adenovirus; Herpes simplex virus (HSV)-1; HSV-2; or a combination thereof.

Embodiment 27. The method of embodiment 26, wherein detecting the known pathogen in the sample comprises carrying out a PCR on the sample with a primer set that hybridizes to nucleotide sequences in the known pathogen to generate a known pathogen specific amplicon.

Embodiment 28. The method of claim 26, wherein classifying the NGU infection in the male subject further comprises determining a concentration of the known pathogen.

Embodiment 29. The method of embodiment 28, wherein determining the concentration of the known pathogen in the sample comprises carrying out a quantitative PCR on the sample with a primer set that hybridizes to nucleotide sequences in the known pathogen to generate a known pathogen specific amplicon.

Embodiment 30. The method of any one of embodiments 27-29, wherein the nucleotide sequences are in a genome of the known pathogen.

Embodiment 31. The method of any one of embodiments 27-29, wherein the nucleotide sequences are in an RNA of the known pathogen.

Embodiment 32. The method of any one of embodiments 27-31, further comprising contacting the known pathogen specific amplicon with a third probe capable of hybridizing to the known pathogen specific amplicon.

Embodiment 33. The method of any one of embodiments 2-32, wherein the therapeutic agent has activity against a pathogen comprising *Haemophilus influenzae, Mycoplasma penetrans*, or both.

Embodiment 34. The method of any one of embodiments 2-33, wherein the therapeutic agent does not have activity against *Lactobacillus iners, Atopobium vaginae, Veillonella atypica*, or a combination thereof.

Embodiment 35. The method of any one of embodiments 2-33, wherein therapeutic agent comprises metronidazole, ceftriaxone, doxycycline, azithromycin ciprofloxacin, or levofloxacin.

Embodiment 36. The method of any one of embodiments 2-33, further comprising introducing a urethral microbiome preparation on the penis or into the urethra of the male subject.

Embodiment 37. The method of any one of embodiments 1-36, wherein the pathogen comprises *Haemophilus influenzae*.

Embodiment 38. The method of embodiment 37, wherein the therapeutic agent is an antibacterial agent with activity against *Haemophilus influenzae*.

Embodiment 39. The method of any one of embodiments 1-38, wherein the pathogen comprises *Mycoplasma penetrans*.

Embodiment 40. The method of any one of embodiments 1-39, wherein the male subject is a man who has sex with men.

Embodiment 41. The method of embodiment 32 or embodiment 40, wherein the therapeutic agent is an antibacterial agent with activity against *Mycoplasma penetrans*.

Embodiment 42. The method of any one of embodiments 1-41, wherein the pathogen comprises *Haemophilus influenzae* and *Mycoplasma penetrans*.

Embodiment 43. The method of embodiment 42, wherein the therapeutic agent is an antibacterial agent with activity against *Haemophilus influenzae* and *Mycoplasma penetrans*.

Embodiment 44. A method of monitoring progression or recurrence of NGU infection in a male subject, comprising detecting the level of expression of *Haemophilus influenzae* and *Mycoplasma penetrans* in a sample from a male subject that has received at least one therapeutic agent for a NGU infection and comparing the level of *Haemophilus influenzae* and *Mycoplasma penetrans* to a control or baseline sample, wherein the level of *Haemophilus influenzae* and *Mycoplasma penetrans* in the sample is measured by detecting the amount of *Haemophilus influenzae* and *Mycoplasma penetrans* in the sample.

Embodiment 45. A kit comprising:
- a first primer set that hybridizes to first nucleotide sequences of *Haemophilus influenzae* or *Mycoplasma penetrans* to generate a first *Haemophilus influenzae* or a first *Mycoplasma penetrans* specific amplicon; and
- a first probe capable of hybridizing to the first *Haemophilus influenzae* or a first *Mycoplasma penetrans* specific amplicon.

Embodiment 46. The kit of embodiment 45, further comprising:
- a second primer set that hybridizes to second nucleotide sequences of *Haemophilus influenzae* or *Mycoplasma penetrans* to generate a second *Haemophilus influenzae* or a second *Mycoplasma penetrans* specific amplicon; and
- a second probe capable of hybridizing to the second *Haemophilus influenzae* or *Mycoplasma penetrans* specific amplicon.

Embodiment 47. The kit of embodiment 46, wherein the first nucleotide sequences, the second nucleotide sequences, or both are in a genome of *Haemophilus influenzae* or *Mycoplasma penetrans*.

Embodiment 48. The kit of embodiment 46 or 47, wherein the first nucleotide sequences, the second nucleotide sequences, or both are in a 16S ribosomal RNA (rRNA) gene of *Haemophilus influenzae* or *Mycoplasma penetrans*.

Embodiment 49. The kit of embodiment 48, wherein the first nucleotide sequences, the second nucleotide sequences, or both are in a variable region of a 16S rRNA gene of *Haemophilus influenzae* or *Mycoplasma penetrans*.

Embodiment 50. The kit of embodiment 46, wherein the first nucleotide sequences, the second nucleotide sequences, or both are in an RNA of *Haemophilus influenzae* or *Mycoplasma penetrans*.

Embodiment 51. The kit of embodiment 50, wherein the RNA corresponds to a 16S rRNA gene of *Haemophilus influenzae* or *Mycoplasma penetrans*.

Embodiment 52. The kit of embodiment 51, wherein the RNA corresponds to a variable region of the 16S rRNA gene of *Haemophilus influenzae* or *Mycoplasma penetrans*.

Embodiment 53. The kit of embodiment 49 or 52, wherein the variable region is a V3 region, a V4 region, or both, of the 16S rRNA.

Embodiment 54. The kit of any one of embodiments 45-53, wherein the first nucleotide sequences are of *Haemophilus influenzae*, and first probe is capable of hybridizing to the first *Haemophilus influenzae* specific amplicon.

Embodiment 55. The kit of embodiment 54, wherein the second nucleotide sequences are of *Mycoplasma penetrans*; and
the second probe is capable of hybridizing to the second *Mycoplasma penetrans* specific amplicon.

Embodiment 56. The kit of any one of embodiments 45-53, wherein the first nucleotide sequences are in a genome of *Mycoplasma penetrans*, and the first probe is capable of hybridizing to the first *Mycoplasma penetrans* specific amplicon.

Embodiment 57. The kit of embodiment 56, wherein:
the second nucleotide sequences are of *Haemophilus influenza*; and
the second probe is capable of hybridizing to the second *Haemophilus influenzae* specific amplicon.

Embodiment 58. The kit of any one of embodiments 46-57, further comprising a third primer set that hybridizes to third nucleotide sequences of *Lactobacillus iners, Atopobium vaginae*, or *Veillonella atypica*, to generate a third *Lactobacillus iners, Atopobium vaginae*, or *Veillonella atypica* specific amplicon.

Embodiment 59. The kit of embodiment 58, further comprising a third probe capable of hybridizing to the third *Lactobacillus iners, Atopobium vaginae*, or *Veillonella atypica* specific amplicon.

Embodiment 60. The kit of embodiment 58 or 59, wherein the third nucleotide sequences are in a genome of *Lactobacillus iners, Atopobium vaginae*, or *Veillonella atypica*.

Embodiment 61. The kit of embodiment 58 or 59, wherein the third nucleotide sequences are in an RNA of *Lactobacillus iners, Atopobium vaginae*, or *Veillonella atypica*.

Embodiment 62. The kit of any one of embodiments 46-61, further comprising a fourth primer set that hybridizes to nucleotide sequences of *Chlamydia trachomatis; Mycoplasma genitalium; Trichomonas vaginalis*; Adenovirus; Herpes simplex virus (HSV)-1; or HSV-2, to generate a *Chlamydia trachomatis; Mycoplasma genitalium; Trichomonas vaginalis*; Adenovirus; Herpes simplex virus (HSV)-1; or HSV-2 specific amplicon.

Embodiment 63. The kit of embodiment 62, wherein the third nucleotide sequences are in a genome of *Lactobacillus iners, Atopobium vaginae*, or *Veillonella atypica*.

Embodiment 64. The kit of embodiment 62, wherein the third nucleotide sequences are in an RNA of *Lactobacillus iners, Atopobium vaginae*, or *Veillonella atypica*.

Embodiment 65. The kit of any one of embodiments 62-64, further comprising a fourth probe capable of hybridizing to the *Chlamydia trachomatis; Mycoplasma genitalium; Trichomonas vaginalis*; Adenovirus; HSV-1; or HSV-2 specific amplicon.

Embodiment 66. A method, comprising:
classifying a risk of human immunodeficiency virus (HIV) infection in a subject comprising detecting a pathogen in a vaginal sample from the subject, the pathogen comprising Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof.

Embodiment 67. The method of embodiment 66, wherein the pathogen comprises Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof.

Embodiment 68. The method of embodiment 66 or 67, further comprising selecting a therapeutic agent to administer to the subject based at least on the detecting and classifying.

Embodiment 69. The method of any one of embodiments 66-68, further comprising administering an effective amount of a therapeutic agent to the subject.

Embodiment 70. A method for preventing acquisition of human immunodeficiency virus (HIV) infection in a subject in need thereof, the method comprising:
administering an effective amount of a therapeutic agent, the subject having a risk of acquiring a HIV determined by an in vitro method comprising:
detecting a pathogen in a vaginal sample from the subject, the pathogen comprising Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, or a combination thereof.

Embodiment 71. The method of embodiment 70, wherein the pathogen comprises Bacterial vaginosis-associated bacterium 2 (BVAB2), vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, or a combination thereof.

Embodiment 72. The method of any one of embodiments 66-71, wherein the vaginal sample is a vaginal irrigation.

Embodiment 73. The method of any one of embodiments 66-71, wherein the vaginal sample is from a vaginal swab.

Embodiment 74. The method of any one of embodiments 66-73, wherein detecting the pathogen in the vaginal sample comprises carrying out a polymerase chain reaction (PCR) on the vaginal sample with a primer set that hybridizes to nucleotide sequences of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia*

*sanguinegens*, *Megasphaera* species type 2, *Mycoplasma hominis*, *Parvimonas* species type 2, or a combination thereof to generate a BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon.

Embodiment 75. The method of embodiment 74, wherein detecting the pathogen in the vaginal sample comprises carrying out a polymerase chain reaction (PCR) on the vaginal sample with a primer set that hybridizes to nucleotide sequences of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, or a combination thereof to generate a BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon.

Embodiment 76. The method of embodiment 74, further comprising contacting the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon with a first probe capable of hybridizing to the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon.

Embodiment 77. The method of any one of embodiments 66-73, wherein detecting the pathogen comprises southern blotting, in situ hybridization, whole genome sequencing, or next-generation sequencing.

Embodiment 78. The method of any one of embodiments 66-76, wherein detecting the pathogen in the vaginal sample comprises determining a concentration of the pathogen in the sample.

Embodiment 79. The method of embodiment 78, wherein determining the concentration of the pathogen in the vaginal sample comprises carrying out a quantitative PCR on the sample with a primer set that hybridizes to nucleotide sequences of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, or a combination thereof, to generate a BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon.

Embodiment 80. The method of embodiment 79, further comprising contacting the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon with a third probe capable of hybridizing to the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 specific amplicon.

Embodiment 81. The method of any one of embodiments 74-80, wherein nucleotide sequences are in a genome of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1 species.

Embodiment 82. The method of embodiment 81, wherein nucleotide sequences are in a 16S ribosomal RNA (rRNA) gene of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1.

Embodiment 83. The method of embodiment 82, wherein nucleotide sequences are in a variable region of a 16S rRNA gene of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1.

Embodiment 84. The method of any one embodiments 74-80, wherein nucleotide sequences are in an RNA of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1.

Embodiment 85. The method of embodiment 82, wherein the RNA corresponds to a 16S rRNA gene of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1.

Embodiment 86. The method of embodiment 85, wherein the RNA corresponds to a variable region of the 16S rRNA gene of BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1.

Embodiment 87. The method of embodiment 83 or 86, wherein the variable region is a V3 region, a V4 region, or both, of the 16S rRNA.

Embodiment 88. The method of any one of embodiments 66-87, wherein classifying the risk of HIV infection in the subject further comprises detecting and determining a concentration of *Lactobacillus crispatus* in the sample.

Embodiment 89. The method of any one of embodiments 66-88, wherein classifying the risk of HIV infection in the subject further comprises detecting a further pathogen in the sample, the further pathogen comprising *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2; or a combination thereof.

Embodiment 90. The method of embodiment 89, wherein the further pathogen comprises *Gemella asaccharolytica*;

*Sneathia amnii; Sneathia sanguinegens; Mycoplasma hominis; Prevotella bivia; Eggerthella*-like species type 1; *Megasphaera* species type 2; *Parvimonas* species type 2; or a combination thereof.

Embodiment 91. The method of any one of embodiments 66-90, wherein classifying the risk of HIV infection in the subject further comprises determining a concentration of the further pathogen.

Embodiment 92. The method of any one of embodiments 68-91, wherein the therapeutic agent has activity against the pathogen.

Embodiment 93. The method of any one of embodiments 89-92, wherein the therapeutic agent has activity against the further pathogen.

Embodiment 94. The method of any one of embodiments 68-93, wherein the therapeutic agent comprises metronidazole, miconazole, clindamycin, or a combination thereof.

Embodiment 95. The method of any one of embodiments 66-94, further comprising introducing a vaginal microbiome preparation to the vagina of the subject.

Embodiment 96. The method of any one of embodiments 68-95, wherein the therapeutic agent is administered intravaginally.

Embodiment 97. The method of any one of embodiments 68-96, wherein the therapeutic agent is administered orally.

Embodiment 98. The method of any one of embodiments 66-97, further comprising administering an effective amount of an anti-retroviral agent.

Embodiment 99. A method of monitoring progression or recurrence of HIV infection in a subject, comprising:
  detecting the level of expression of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 in a sample from a subject that has received at least one treatment for HIV infection and comparing the expression of the BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 to a control, wherein the level of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 in a sample is measured by detecting the amount of BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 in the sample.

Embodiment 100. A kit comprising:
  a first primer set that hybridizes to first nucleotide sequences of a pathogen comprising BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2, to generate a BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 specific amplicon; and
  a first probe capable of hybridizing to the BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1, *Eggerthella*-like species type 1, *Gemella asaccharolytica, Lactobacillus crispatus, Sneathia amnii, Sneathia sanguinegens, Megasphaera* species type 2, *Mycoplasma hominis, Parvimonas* species type 2 specific amplicon.

Embodiment 101. The kit of embodiment 100, wherein the pathogen comprises BVAB2, vaginal TM7 species type 1, *Peptoniphilus lacrimalis, Porphyromonas* species type 1, *Bulleidia* species type 1, *Fusobacterium equinum, Fusobacterium gonidiaformans, Porphyromonas asaccharolytica, Porphyromonas uenonis*, unclassified Bacteroidales species type 1.

Embodiment 102. The kit of embodiment 100 or 101, wherein the first nucleic acid sequences are in a genome of the pathogen.

Embodiment 103. The kit of any one of embodiments 100-102, wherein the first nucleic acid sequences are in a 16S ribosomal RNA (rRNA) gene of the pathogen.

Embodiment 104. The kit of embodiment 103, wherein the first nucleic acid sequences are in a variable region of a 16S rRNA gene of the pathogen.

Embodiment 105. The kit of embodiment 100 or 101, wherein the first nucleic acid sequences are in an RNA of the pathogen.

Embodiment 106. The kit of embodiment 105, wherein the RNA corresponds to a 16S rRNA gene of the pathogen.

Embodiment 107. The kit of embodiment 106, wherein the RNA corresponds to a variable region of the pathogen.

Embodiment 108. The kit of embodiment 104 or 107, wherein the variable region is a V3 region, a V4 region, or both, of the 16S rRNA.

Embodiment 109. The kit of any one of embodiments 100-108, further comprising:
- a plurality of primer sets, individual primer sets of the plurality of primer sets hybridize to respective nucleotide sequences of a respective pathogen comprising BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2, or a combination thereof, to generate a BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon, the plurality of primer sets comprising the first primer set; and
- a plurality of probes, individual probes of the plurality of probes being capable of hybridizing to the BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon.

Embodiment 110. The kit of embodiment 109, wherein the respective pathogen comprising BVAB2, vaginal TM7 species type 1, *Peptoniphilus lacrimalis*, *Porphyromonas* species type 1, *Bulleidia* species type 1, *Fusobacterium equinum*, *Fusobacterium gonidiaformans*, *Porphyromonas asaccharolytica*, *Porphyromonas uenonis*, unclassified Bacteroidales species type 1, or a combination thereof.

Embodiment 111. The kit of embodiment 109 or 110, wherein the respective nucleic acid sequences are in a genome of the respective pathogen.

Embodiment 112. The kit of any one of embodiments 109-111, wherein the respective nucleic acid sequences are in a 16S ribosomal RNA (rRNA) gene of the respective pathogen.

Embodiment 113. The kit of embodiment 112, wherein the respective nucleic acid sequences are in a variable region of the 16S rRNA gene of the respective pathogen.

Embodiment 114. The kit of embodiment 109 or 110, wherein the respective nucleic acid sequences are in an RNA of the respective pathogen.

Embodiment 115. The kit of embodiment 114, wherein the RNA corresponds to a 16S rRNA gene of the respective pathogen.

Embodiment 116. The kit of embodiment 115, wherein the RNA corresponds to a variable region of the respective pathogen.

Embodiment 117. The kit of embodiment 113 or 116, wherein the variable region is a V3 region, a V4 region, or both, of the 16S rRNA.

Embodiment 118. The kit of any one of embodiments 109-117, further comprising a second primer set that hybridizes to second nucleotide sequences of *Lactobacillus crispatus* to generate a *Lactobacillus crispatus* specific amplicon.

Embodiment 119. The kit of embodiment 118, further comprising a second probe capable of hybridizing to the *Lactobacillus crispatus* specific amplicon.

Embodiment 120. The kit of embodiment 118 or 119, wherein the second nucleic acid sequences are in a genome of *Lactobacillus crispatus*.

Embodiment 121. The kit of any one of embodiments 118-120, wherein the second nucleic acid sequences are in a 16S ribosomal RNA (rRNA) gene of *Lactobacillus crispatus*.

Embodiment 122. The kit of embodiment 121, wherein the second nucleic acid sequences are in a variable region of a 16S rRNA gene of *Lactobacillus crispatus*.

Embodiment 123. The kit of embodiment 118 or 119, wherein the second nucleic acid sequences are in an RNA of *Lactobacillus crispatus*.

Embodiment 124. The kit of embodiment 123, wherein the RNA corresponds to a 16S rRNA gene of *Lactobacillus crispatus*.

Embodiment 125. The kit of embodiment 124, wherein the RNA corresponds to a variable region of *Lactobacillus crispatus*.

Embodiment 126. The kit of embodiment 122 or 125, wherein the variable region is a V3 region, a V4 region, or both, of the 16S rRNA.

Embodiment 127. The kit of any one of embodiments 100-126, further comprising a third primer set that hybridizes to nucleotide sequences of *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2, or a combination thereof, to generate a *Eggerthella*-like species type 1, *Gemella asaccharolytica*, *Lactobacillus crispatus*, *Sneathia amnii*, *Sneathia sanguinegens*, *Megasphaera* species type 2, *Mycoplasma hominis*, *Parvimonas* species type 2 specific amplicon.

Embodiment 128. The kit of embodiment 127, further comprising a third probe capable of hybridizing to the *Gemella asaccharolytica*, *Sneathia* amnii, *Sneathia sanguinegens*, *Mycoplasma hominis*, *Prevotella bivia*, *Eggerthella*-like species type 1, *Megasphaera* species type 2, or *Parvimonas* species type 2 specific amplicon.

Embodiment 129. The kit of embodiment 127 or 128, wherein the third nucleic acid sequences are in a genome of *Lactobacillus crispatus*.

Embodiment 130. The kit of any one of embodiments 127-129, wherein the second nucleic acid sequences are in a 16S ribosomal RNA (rRNA) gene of *Lactobacillus crispatus*.

Embodiment 131. The kit of embodiment 130, wherein the second nucleic acid sequences are in a variable region of a 16S rRNA gene of *Lactobacillus crispatus*.

Embodiment 132. The kit of embodiment 127 or 128, wherein the second nucleic acid sequences are in an RNA of *Lactobacillus crispatus*.

Embodiment 133. The kit of embodiment 132, wherein the RNA corresponds to a 16S rRNA gene of *Lactobacillus crispatus*.

Embodiment 134. The kit of embodiment 133, wherein the RNA corresponds to a variable region of *Lactobacillus crispatus*.

Embodiment 135. The kit of embodiment 131 or 134, wherein the variable region is a V3 region, a V4 region, or both, of the 16S rRNA.

Embodiments of this invention are further illustrated by the following non-limiting examples.

EXAMPLES

Example 1

Urethral Microbiota in Idiopathic NGU

Figure 2:
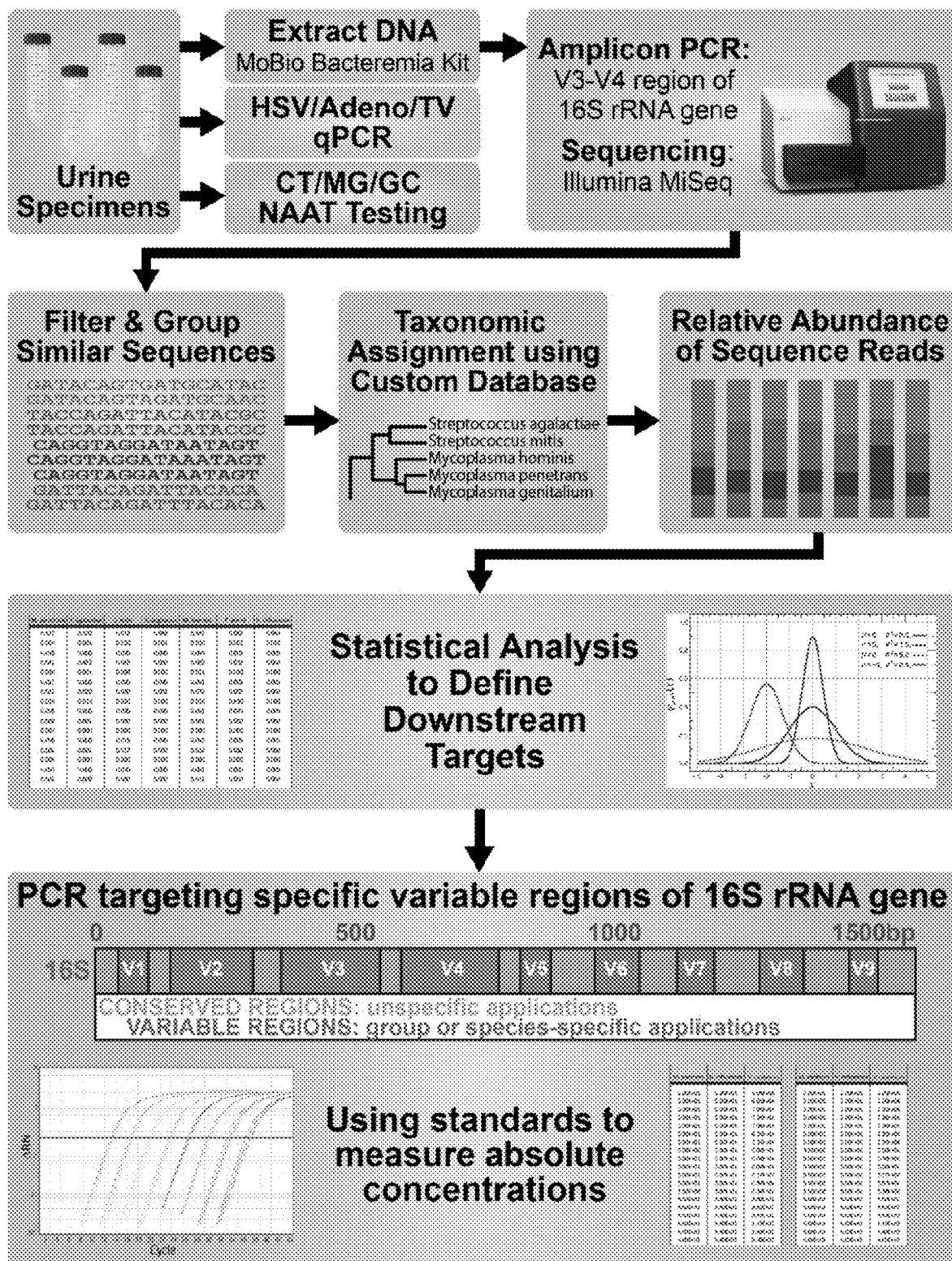
FIG. 2 provides a flowchart of the sequential molecular workflow for identifying bacteria associated with NGU, as described in Example 1.

The association of urethral bacteria with NGU among subjects including men who have sex with men (MSM) and men who have sex with women (MSW). Urine samples were collected from 434 male subjects attending a sexually transmitted disease (STD) clinic. Of the 434 men, 199 were MSM (46%) and 235 were MSW (54%). The NGU status of each man was determined. NGU was defined as having urethral symptoms or visible discharge and >5 PMNs/high powered field (HPF). Men without NGU had no urethral symptoms, no discharge, and <5 PMNs/HPF. A summary of the subjects enrolled in the study is shown in FIG. 1. Samples comprised 250 cases of NGU and 184 controls (FIG. 1, Table 2, and Table 3). NGU positive subjects were screened for *Neisseria gonorrhoeae* (GC), *Chlamydia trachomatis* (CT), *Mycoplasma genitalium* (MG), *Trichomonas vaginalis* (TV), adenovirus, Herpes simplex virus (HSV)-1, and HSV-2. *Neisseria gonorrhoeae* (GC), CT, and MG were detected using NAAT testing (Aptima). TV, adenovirus, and HSV were measured using qPCR. The absence of CT, MG, TV, adenovirus, and HSV was considered idiopathic NGU. A flowchart of the sequential molecular workflow for identifying bacteria associated with NGU is shown in FIG. 2.

Study Design and Study Population

Participants who were ≥16 years, assigned male sex at birth, attending the Public Health—Seattle & King County (PHSKC) STD Clinic, and previously recruited into a cross-sectional study between August 2014 and April 2018 formed the case-control study population. The Institutional Review Boards at the University of Washington and Fred Hutchinson Cancer Research Center approved the study. All men provided written informed consent. Men had exclusively male or exclusively female sex partners in the past year. Two transgender women who had sex only with men also enrolled. Men reporting both male and female partners in the past year, known contact to a partner with urogenital NG, no sex in the past 60 days, antibiotic use in the past 30 days, or with *Neisseria gonorrhoeae* (NG) by Gram stain or nucleic acid amplification testing were excluded. Men with severe symptoms characteristic of adenovirus and HSV were not explicitly excluded, but rarely enrolled. All participants completed a computer-assisted self-interview, underwent a standard genital examination and provided 30-50 mL of first-void urine and urethral swab specimens. Urethral exudates were Gram-stained to quantitate PMNs and examined for the presence of Gram-negative intracellular diplococci indicative of NG. Cases of NGU had urethral symptoms or visible discharge and >5 PMNs per high-power field (HPF). Controls had no urethral symptoms, no discharge and <5 PMNs/HPF. Urine specimens were tested for NG, CT, and MG using Aptima assays with analyte-specific reagents that are for research use only (Hologic, San Diego, California), while TV, adenovirus and HSV were measured using quantitative PCR (qPCR). NGU in the absence of CT, MG, TV, adenovirus and HSV was considered idiopathic.

DNA Extraction and Quantification

DNA was extracted from urine samples stored at 4° C. for 1-3 days prior to processing in the laboratory using the QIAamp BiOstic Bacteremia Kit (Qiagen, Hilden, Germany). The Tris-EDTA buffer for DNA elution was filtered twice to minimize contamination. Sham extraction negative controls were included to monitor for potential contamination during processing of urine pellets. DNA from mock communities (positive controls) with known bacterial composition was extracted. PCR inhibition was monitored using an internal amplification control assay and samples were considered inhibited if delayed by ≥2.0 cycles. Bacterial DNA concentrations were measured using a TaqMan-based qPCR assay targeting the V3-V4 region of the 16S rRNA gene.

Broad-Range PCR and Sequencing

Broad-range PCR amplification of the V3-V4 region of the 16S rRNA gene was performed on samples, positive and negative controls. Amplicons were sequenced on the Illumina MiSeq instrument (San Diego, CA). Sequence reads were demultiplexed and the DADA2 package was used for processing reads resulting in a list of unique sequence variants (SVs). Taxonomy was assigned to unique SVs based on location on a phylogenetic tree.

Quantitative PCR

Species-specific qPCR assays were developed to measure DNA concentrations of *Mycoplasma penetrans* (MP), *Haemophilus influenzae* (HI), TV and UU as described in Examples 2 and 3. Assays targeted the 16S rRNA genes of MP and HI, the urease accessory protein G gene of UU, and the 23S rRNA gene of TV.

Statistical Analyses

Patient characteristics were compared using Fisher's exact tests for categorical variables and Wilcoxon rank-sum test for continuous variables. Samples yielding >1,000 sequence reads were included in all subsequent analyses. Alpha diversity was calculated using the Shannon Diversity Index and compared between cases and controls using Wilcoxon rank-sum tests. A sequential PCR approach (Broad-range PCR-4qPCR) was used to identify associations between bacterial taxa and NGU. First, compositional lasso analysis of bacterial taxa was conducted to identify associations between bacteria and NGU, among MSW and MSM separately. Zeros were replaced in the sequence count data with 0.5 and re-calculated relative abundances. Beta coefficients (3) estimating change in probability of NGU per log 2 change in relative abundance were calculated using the CVS R package (http://www.math.pku.edu.cn/teachers/linw/software.html). Bacterial taxa with non-zero beta-coefficients were considered to be associated with NGU; compositional lasso does not yield p-values. Additional analyses to examine associations between bacterial taxa and NGU were conducted to confirm taxa identified in the compositional lasso approach (Table 18). Odds ratios from exact logistic regression analyses and Wilcoxon rank-sum tests were used to compare relative abundances. Multiple comparisons were accounted for using the Benjamini-Hochberg False Discovery Rate. Taxa positively associated with NGU were selected for measurement of concentrations using targeted qPCR to validate the associations noted. The Fisher's exact test was used for binary variables (detected, not detected). Concentrations of potential pathogens were evaluated for their associations with NGU, and idiopathic NGU among participants in whom the bacterium was detected using Wilcoxon rank-sum tests. All analyses used Rv3.5.1 and Stata v15.

Preparation of Mock Communities as Positive Controls

Two mock communities were prepared to evaluate if bacterial taxa present in the mock communities were detected with the below described laboratory processes and bioinformatics pipeline. The first mock community was created using plasmids containing the 16S rRNA gene of genital tract bacteria, such that bacterial taxa that are yet to be cultivated such as Bacterial Vaginosis-Associated Bacterium-1 (BVAB1) and vaginal TM7 can be detected using the study pipeline (Table 19). The second mock community was prepared using bacterial isolates typically present in the human genital tract. All taxa that were included in both mock communities were detected with the study pipeline. An additional taxon was detected with each mock community at low relative abundance; *Shigella/Escherichia* in mock community 1 (0.08%) and *Streptococcus mitis* group in mock community 2 (0.42%) (Table 20). As both taxa were dominant members of the bacterial community in the dataset, this likely represents cross-contamination between wells.

Broad-Range PCR, Sequencing and Processing of Sequence Reads

Broad-range PCR amplification of the V3-V4 hypervariable region of the 16S rRNA gene was performed on samples and negative controls using the primers below. Forward primers were used in a 3-1-1 ratio.

```
338Fa-nextera
                                         (SEQ ID NO: 7)
TCGTCGGCAGCGTCAGATGTGTATAAGAGACAGAYTCCTRCGGGARGCA

GCAG

338Fb-nextera
                                         (SEQ ID NO: 8)
TCGTCGGCAGCGTCAGATGTGTATAAGAGACAGACTCCTACGGGAGGCT

GC

338Fc-nextera
                                         (SEQ ID NO: 9)
TCGTCGGCAGCGTCAGATGTGTATAAGAGACAGACACCTACGGGTGGCA

GC

The reverse primer was 806R-nextera
                                        (SEQ ID NO: 10)
GTCTCGTGGGCTCGGAGATGTGTATAAGAGACAGGGACTACHVGGGTAT

CTAAT
```

The italic sequences are the overhang sequences for compatibility with the Nextera®XT Index kit v2 (Illumina San Diego, CA), and the primer sequences targeting the 16S rRNA gene are denoted in bold letters.

Each 50 µL amplicon PCR master mix contained 1× Accuprime Buffer II, additional 2 mM magnesium chloride, 0.4 µM of forward primer formulation, 0.4 µM of reverse primer, and 0.03 U/µL Accuprime™ High Fidelity Taq polymerase (Thermo Fisher Scientific, Waltham, MA). DNA quantities ranging from $2.2 \times 10^3$-$2.4 \times 10^6$ bacterial 16S rRNA gene copies from each urine sample were added to the PCR reaction. All buffers and water used for the clean-up and dilution steps were filtered using a 100,000 MW cut-off filter. Cycling conditions included a denaturation step at 94° C. for 15 s, followed by 28 cycles of 94° C. for 30 s, 55° C. for 30 s, and 68° C. for 1 min. Final extension was at 68° C. for 7 min. Band size (604 bp) was confirmed with gel electrophoresis, but all control samples were processed through the pipeline regardless of band (blind). Amplicons were purified using the Agencourt AMPure XP beads (Beckman Coulter, Indianapolis, IN) per the 16S Metagenomic Sequencing Library Preparation protocol. Purified amplicons were subjected to Index PCR using NexteraXT index kits v2 set A, set B, set C, and set D to multiplex up to 384 samples per sequencing run. After Index PCR, the amplicons were purified using Agencourt AMPure XP beads, air dried and eluted in 40 µL 1×TE buffer. DNA concentrations in each sample was measured using the Quant-iT dsDNA assay kit-high sensitivity (Thermo Fisher Scientific, Waltham, MA) and equimolar quantities of samples were pooled. For samples with low DNA quantities, up to 30 µL of DNA were added to sub-pools when equimolar quantities could not be achieved. The amplicons were subjected to sequencing on the Illumina MiSeq instrument (Illumina, San Diego, CA) with the MiSeq® Reagent Kit v3-600 cycle to capture paired-end reads (2×300). PhiX Control Library v3 (Illumina) was combined with the amplicon library at 15% to compensate for low base diversity.

Raw sequence reads were demultiplexed using Illumina MiSeq's onboard software. Demultiplexed reads were processed using barcodecop v0.4.1 to enforce barcode quality using default settings as well as ensuring exact barcode matches to forward and reverse reads. The DADA2 package was used for error correction, dereplication, paired-end assembly, and chimera removal and a list of unique sequence variants (SVs) were generated. Sequence reads are available from the NCBI Short Read Archive (Bioproject Accession: PRJNA637612).

Reference Set Creation and Taxonomic Assignment

The SVs were used to recruit full-length 16S rRNA gene sequences from records downloaded from NCBI Apr. 5, 2018 using the ya16sdb pipeline based on similarity to experimentally generated reads (code available by request). A phylogenetic tree was constructed using RAxML with the niche-specific full length sequences recruited from NCBI and locally generated 16S rRNA gene sequences from bacterial isolates and clones from the genital tract. Additional species were added to broaden the taxonomy when leaves contained only 1 representative sequence. The list of bacterial taxa used for the creation of the urethral reference set used for the analyses is provided as Table 21. A multiple sequence alignment of both query and reference sequences was created using cmalign and query sequences were placed on the phylogenetic tree using pplacer. Taxonomy was assigned to each unique SV based on location on the tree. Taxonomic assignments were validated by inspection of multiple sequence alignments, phylogenetic trees and BLAST searches. Bacterial taxa represented by fewer than 25 reads in a given sample were excluded from that sample to minimize environmental contaminant sequences from being included in the final dataset; bacterial taxa judged to be contaminants based on prevalence among negative controls were also removed from the final data set (Table 22).

Quantitative PCR

Species-specific qPCR assays were developed to measure DNA concentrations of *Mycoplasma penetrans*, *Ureaplasma urealyticum*, *Haemophilus influenzae*, and *Trichomonas vaginalis*. Assays targeted the 16S rRNA genes of *M. penetrans* and *H. influenzae*, the urease accessory protein G gene of *U. urealyticum*, and the 23S rRNA gene of *T. vaginalis*. All assays underwent 45 cycles of amplification on the QuantStudio™ 6 Flex Real-Time PCR System (Applied Biosystems, Waltham, MA) in 15 µL reactions. Core reagents were supplied by Applied Biosystems (Waltham, CA). *U. urealyticum* and *H. influenzae* were run with TaqMan™ Fast Advanced Master Mix (1×) with primers at 0.8 µM per reaction and probe at 150 nM per reaction. *T. vaginalis* was run with TaqMan™ Fast Advanced Master Mix (1×) with primers at 0.9 µM per reaction and probe at 180 nM. *M. penetrans* was run with master mix containing buffer A (1×), deoxynucleotide triphosphates (1 mM), magnesium (4 mM), primers (1.2 µM), probe (200 nM), AmpErase uracil-N-glycosylase (0.015 U) and TaqGold polymerase (0.45 U) per reaction. Plasmid standards were run in duplicate with a lower limit of detection of 1.25 gene copies/µL DNA. Primer and probe sequences, as well as PCR conditions are listed in Table 23. Specificity and sensitivity testing were conducted as previously described and the bacteria tested for specificity assay are listed in Tables 24-27.

Real-time PCR assays for adenovirus and HSV have been previously published. Briefly, the extracted DNA was diluted 2× and 10 µL of the diluted DNA was used for the assays. Each 30 µL adenovirus PCR reaction contained 15 µL of 2× QuantiTect multiplex PCR master mix (Qiagen, Hilden, Germany), 66 nM of B/E/C primers, 415 nM of A/F primers, 67 nM B/E/C probes, 100 nM A/F probes, and 0.03 unites of uracil-N-glycosylase (UNG). Each 30 µl HSV typing quantification real-time PCR reaction contained 15 µl of 2× QuantiTect multiplex PCR master mix, 830 nM primers, 150 nM HSV-1 probe (VIC/QSY), 100 nM HSV-2 probe (FAM/QSY) and 0.03 units of UNG. An internal amplification control (EXO) was spiked in to all PCR reactions to monitor PCR inhibition and a negative result was accepted only if EXO was amplified and detected. Cycling conditions for both adenovirus and HSV assays included the following: 50° C. for 2 minutes, 95° C. for 15 minutes, followed by 45 cycles of 94° C. for 1 minute and 60° C. for 1 minute.

Discussion and Results

Figure 3:
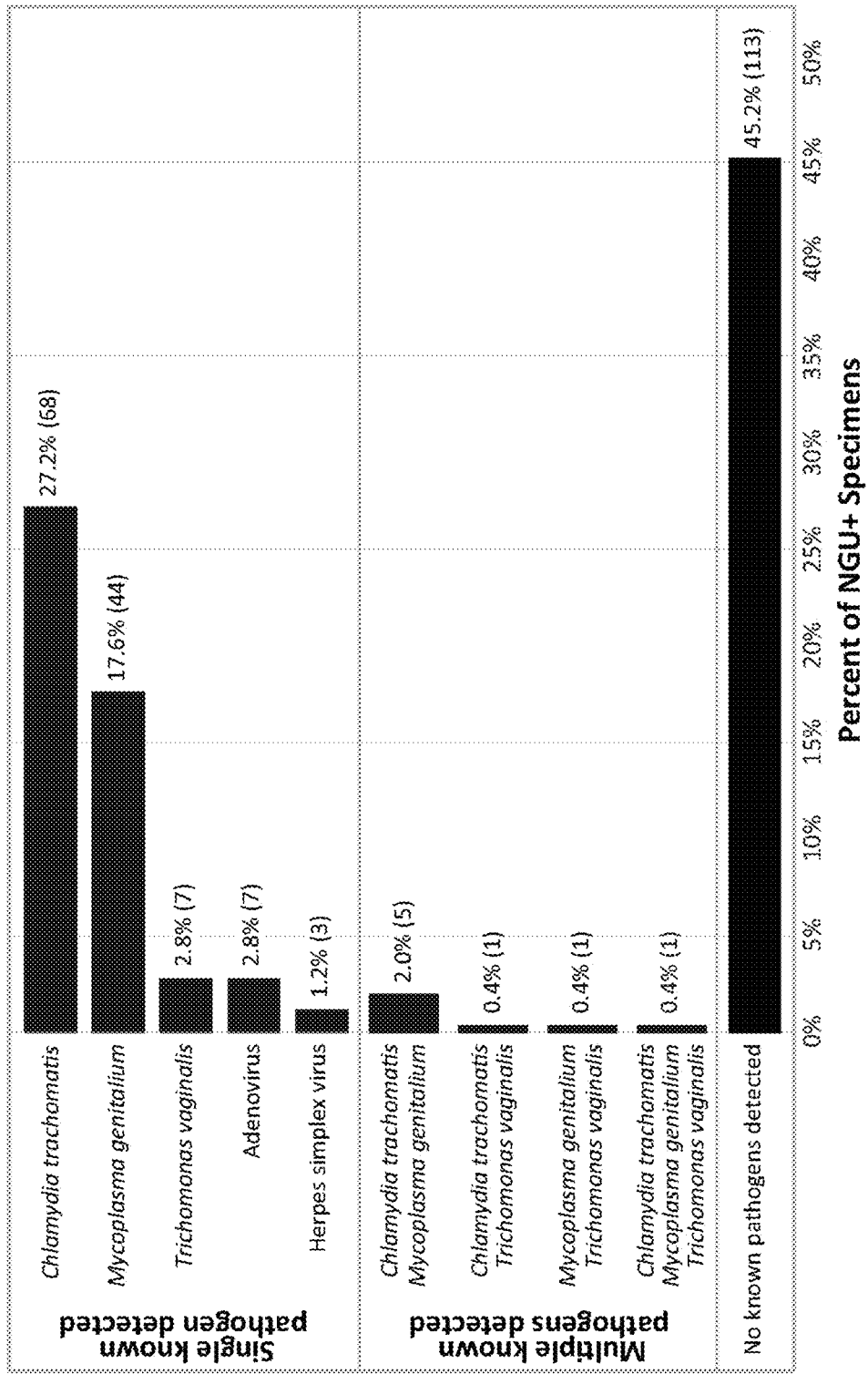
FIG. 3 shows the percentage of NGU+ subjects with various known pathogens detected.

Among cases of NGU, 129 (52%) were infected with a single known pathogen, 3% had two pathogens detected and <1% had three pathogens detected using NAAT or qPCR (FIG. 3). Of NGU cases that were colonized with a single pathogen, the majority were infected with either CT (52.7%) or MG (34.1%) while prevalence of HSV, adenovirus or TV was low. 95 MSM subjects (44 NGU+) and 143 MSW subjects (46 NGU+) were negative for CT, MG, adenovirus, and HSV. Of 250 subjects with NGU, 45.2% (113 subjects) had no known pathogen detected, hence classified as having idiopathic NGU. The results are shown in FIG. 3. The numbers in parentheses in the bar chart indicate the number of subjects in each group.

Figure 4A:
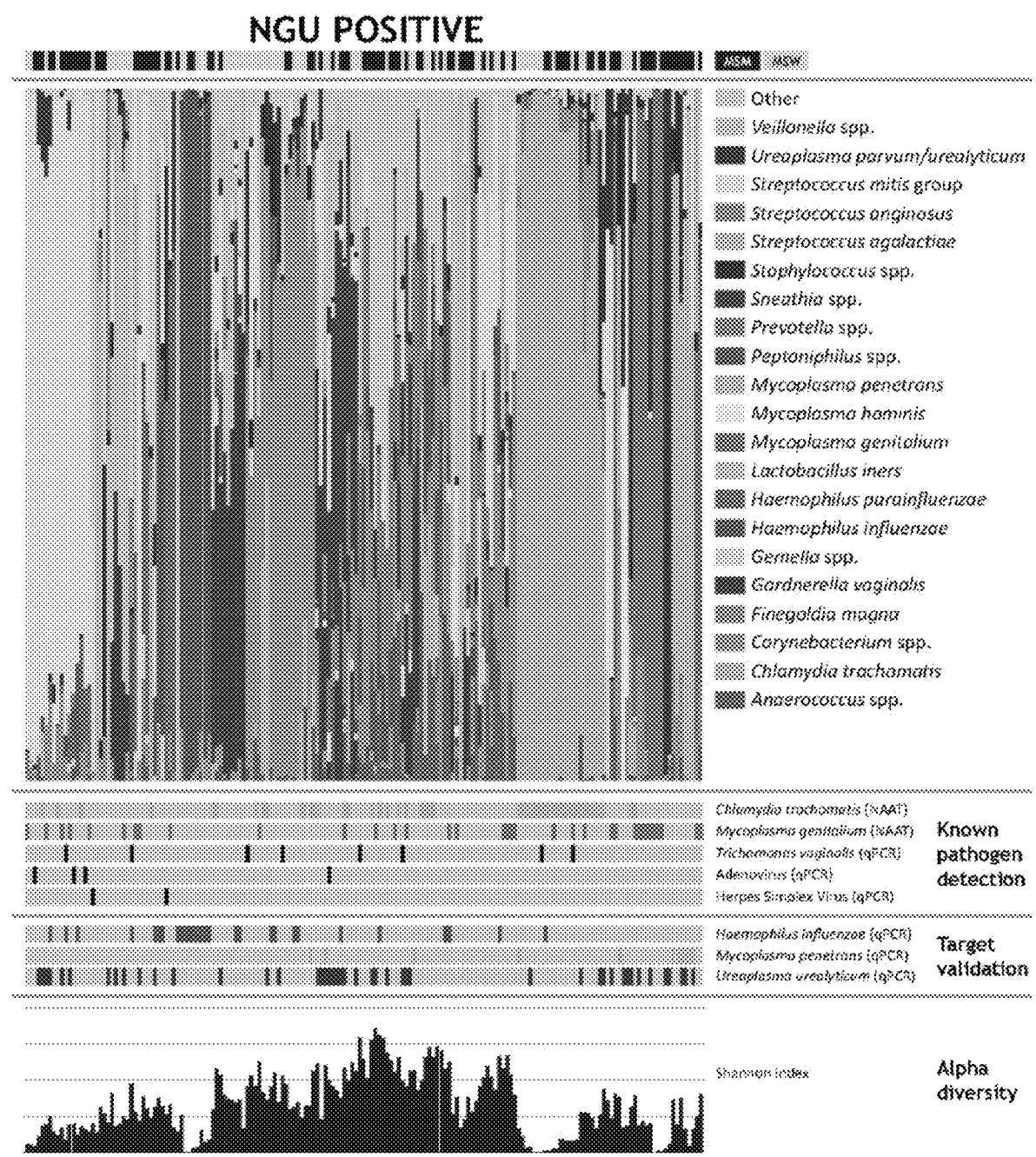
FIG. 4A and FIG. 4B illustrate bacterial communities in MSM and MSW with NGU (FIG. 4A) and without NGU (FIG. 4B).
Figure 4B:
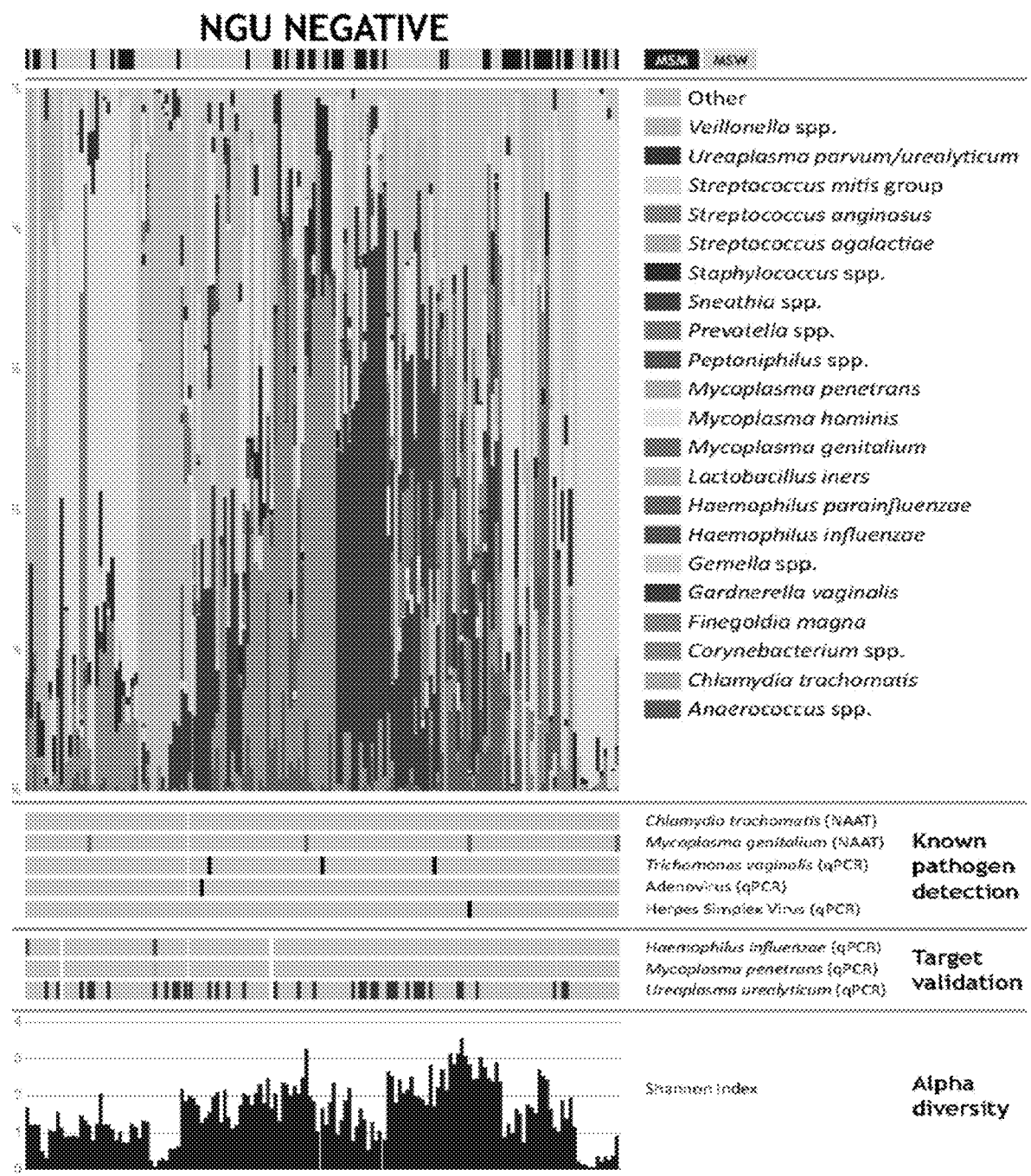

Urethral microbiota was then characterized using broad-range 16S rRNA gene PCR with sequencing. Compositional lasso analysis of bacterial taxa was conducted to identify associations between bacteria and NGU. Further, statistical analyses were used to select qPCR targets. *H. influenzae* and *M. penetrans* were positively associated with non-CT/MG NGU, and were thus selected for qPCR. *U. urealyticum* was also selected for qPCR as it has been associated with NGU in some studies. *A. vaginae* (in MSW) and *L. iners* (in MSW), and *V. atypica* (in MSM), among others, were associated with the absence of NGU. Wilcoxon rank-sum tests were used to compare quantities of bacteria. Bacterial communities in MSM and MSW with NGU and without NGU are illustrated in FIG. 4A and FIG. 4B, respectively.

Of 434 subjects, urine samples from 330 subjects (76%) contained sufficient bacterial DNA for 16S rRNA gene sequencing; and 328 subjects produced >1000 sequence reads/sample, sufficient reads to evaluate association with NGU, NGU positive subjects were less likely to yield sequence data (70% vs. 84%, Fisher's p=0.001). Overall, 13.35 million sequence reads were generated with a mean of 29,423 reads and a median of 40,711 reads per sample. Most (96.2%) reads were classified to the species level. Alpha diversity among men with NGU was lower compared to men without NGU (1.21 vs. 1.53, p=0.005). When stratified by sex of sex partner, diversity was lower among both MSM and MSW with NGU than without NGU, but the latter was not statistically significant (1.09 vs. 1.31, p=0.050 and 1.39 vs. 1.66, p=0.085, respectively).

Relative abundance data obtained from 328 men were evaluated to determine associations of bacteria with NGU. A dominant taxon was defined as >50% relative abundance within a sample. Hierarchical clustering highlighted *H. influenzae*—and *M. penetrans*-dominant bacterial communities in men with NGU, in addition to previously known pathogens including CT- and MG-dominant communities.

Figure 5:
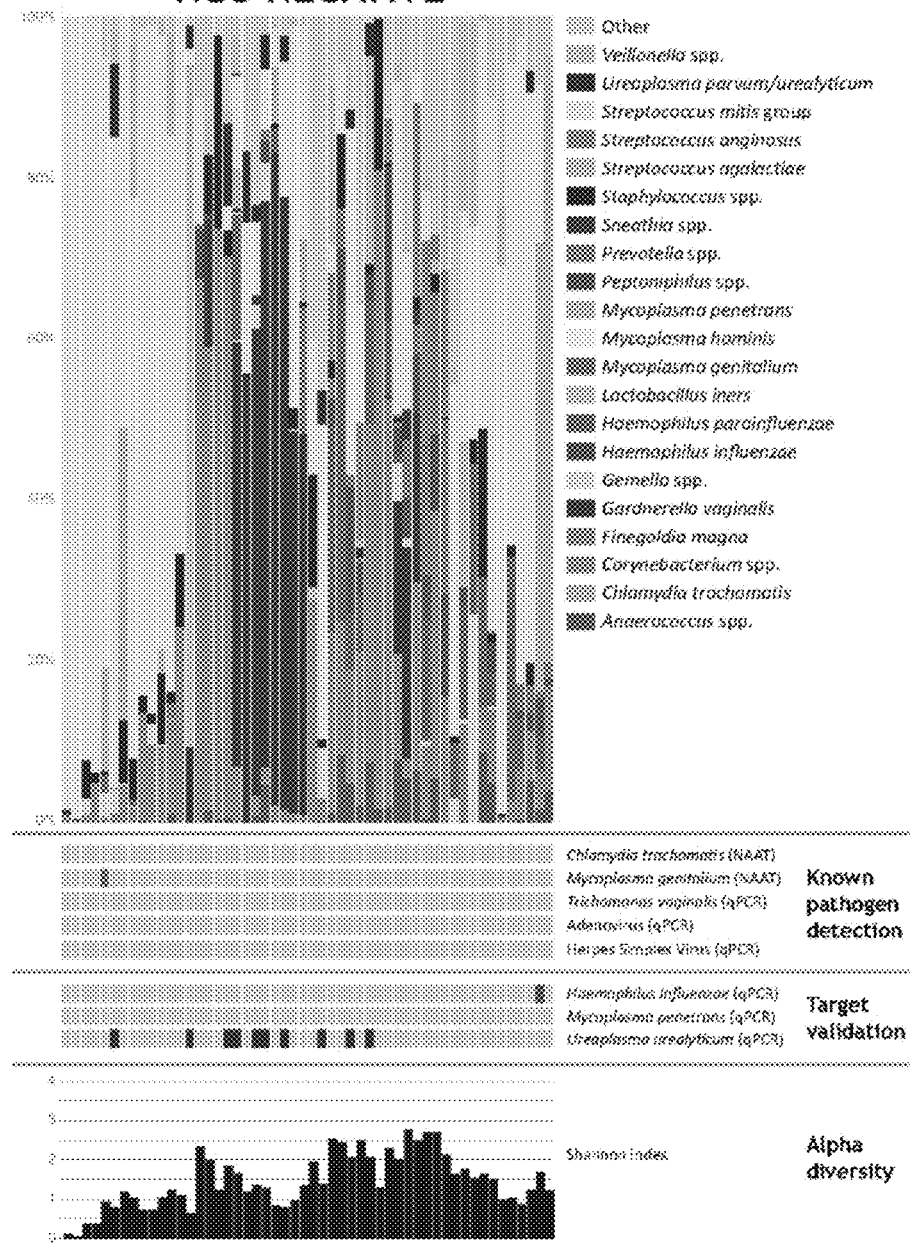
FIG. 5 illustrates urethral bacterial communities in MSM with NGU and without NGU.
Figure 5:
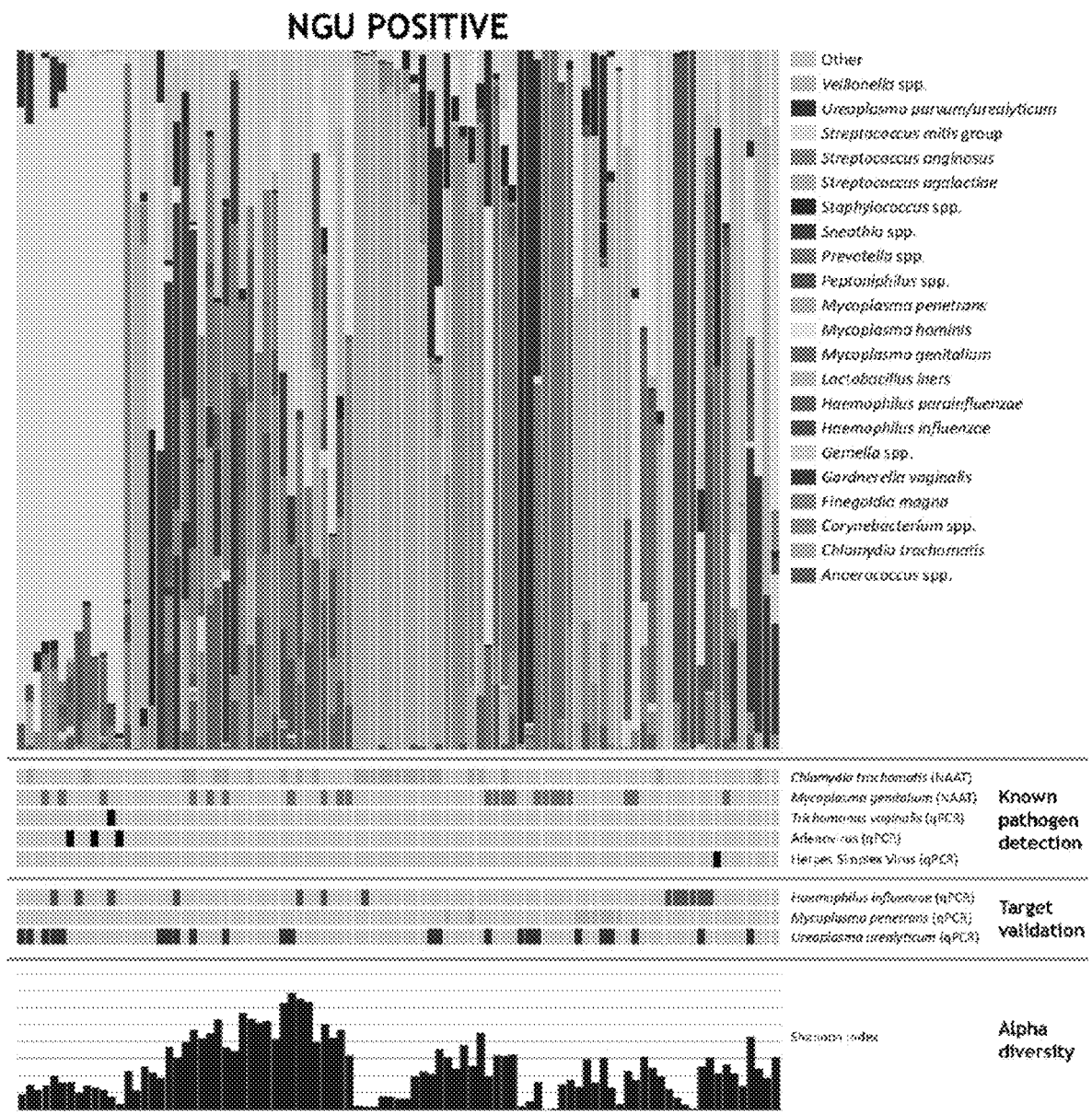
Figure 6:
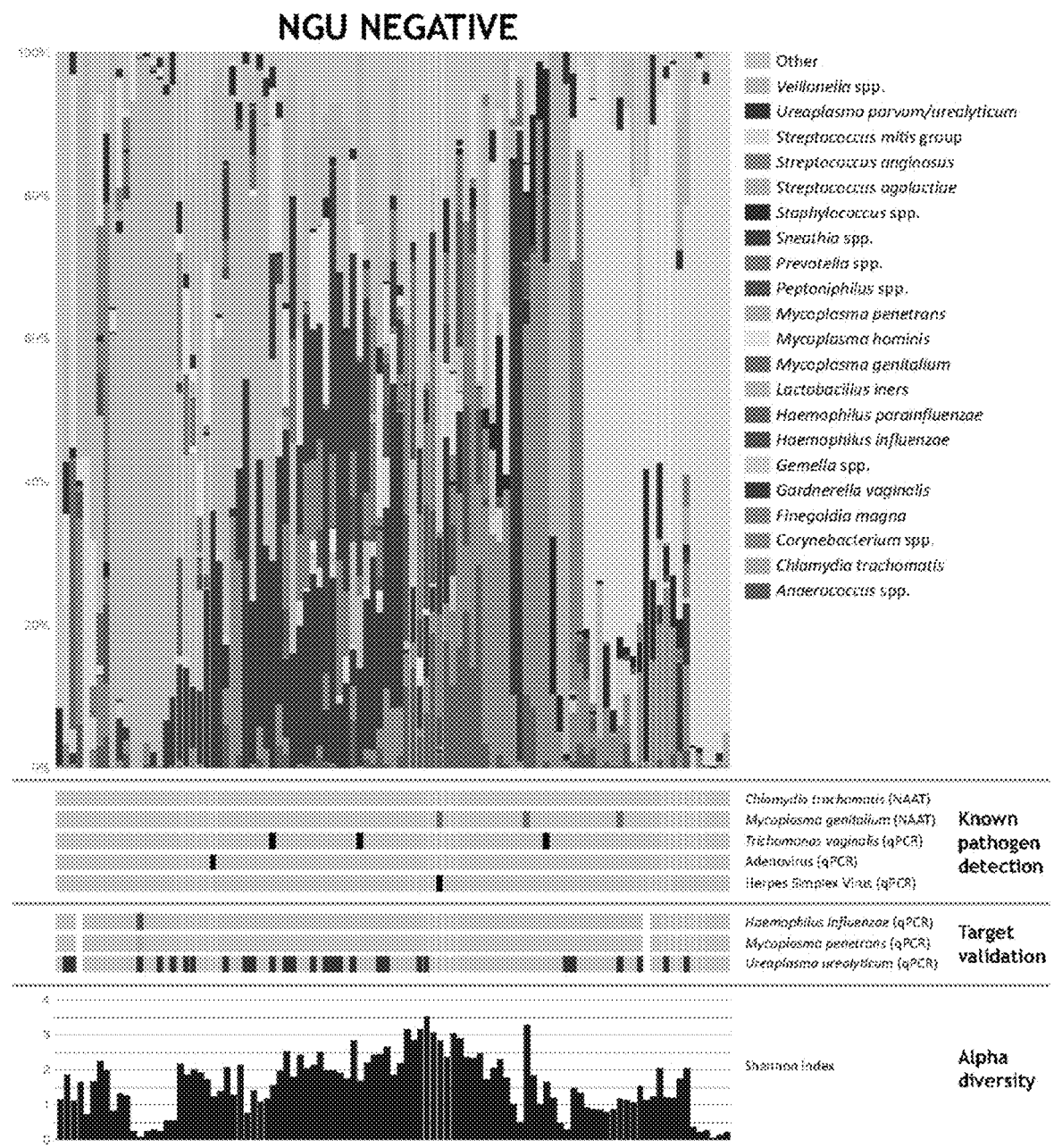
FIG. 6 illustrates urethral bacterial communities in MSW with NGU and without NGU.
Figure 6:
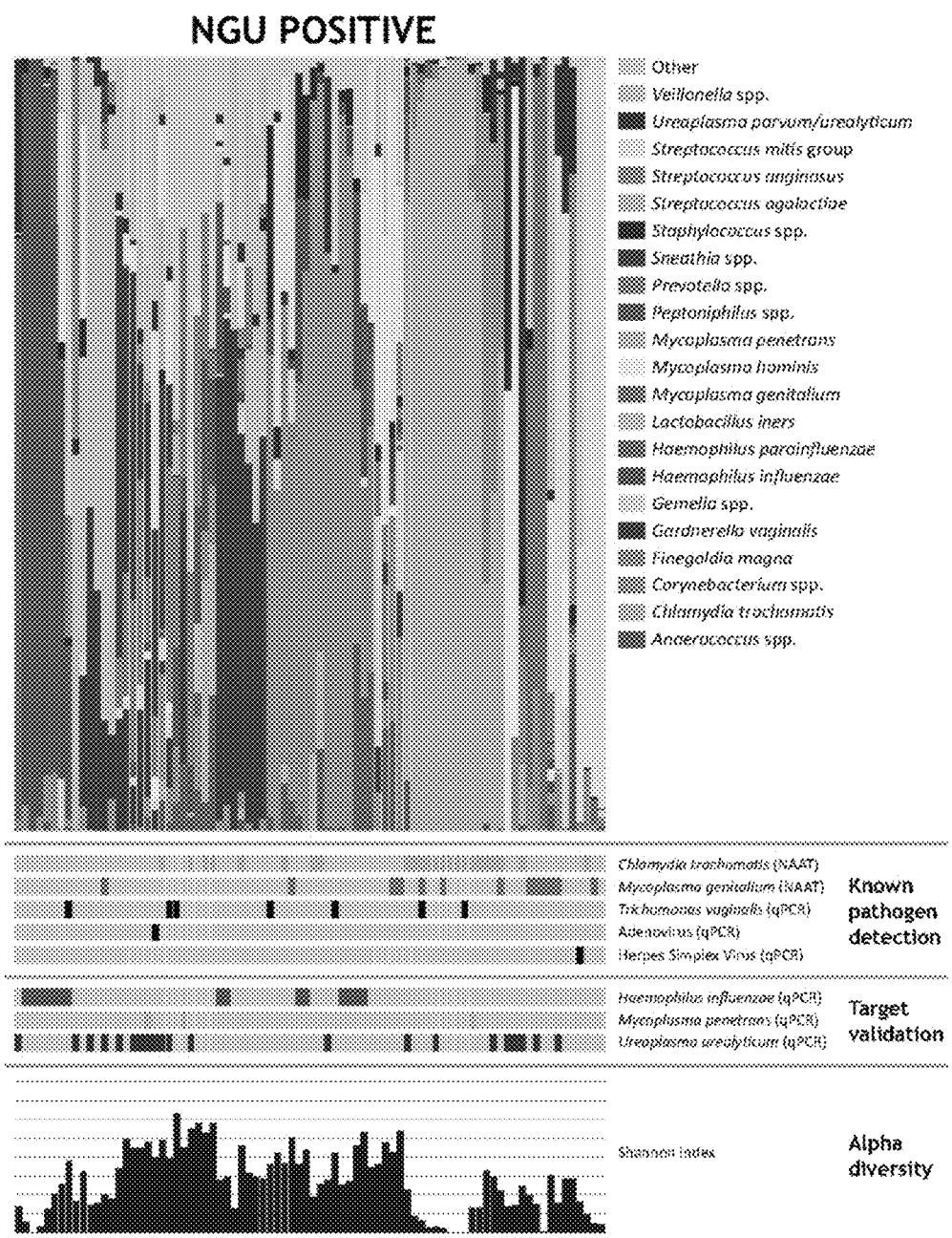

Two men with NGU had *Ureaplasma* dominant communities. Among men with NGU in whom CT sequence reads were detected, 40% were dominated by this bacterium and 35% of men with MG reads were dominated by this bacterium. While other taxa were dominant (e.g., *Corynebacterium* spp., and *Streptococcus mitis* group), no other bacterial communities were consistently different between cases and controls. On stratifying by sex of sex partner, both MSM and MSW had HI-dominant communities, while only MSM had MP-dominant communities in men with NGU (FIG. 5 and FIG. 6). *Lactobacillus iners*-dominant communities were noted mostly among MSW, with only one in MSM.

The association between specific bacterial taxa and NGU in men with no detection of CT and MG (non-CT/MG NGU) is shown in Table 4. Compositional lasso analysis showed that higher relative abundances of HI (ß=0.00844) and MP B=0.00112) were positively associated with NGU in MSM, while HI was positively associated with NGU in MSW (ß=0.00949) (Table 5). As expected, higher relative abundances of CT and MG model also identified bacterial species that were inversely associated with NGU in MSM and MSW although the taxa were different among MSM and MSW (Table 5). Notably, *L. iners* was inversely associated with NGU among MSW (ß=−0.00690) but not MSM. *Atopobium vaginae* (MSW), *Streptococcus mitis* (MSW) and *Veillonella atypica* (MSM) were also associated with the absence of NGU, among other bacteria (Table 5). The beta coefficient (ß) is an estimate of the change in probability of NGU per log 2 change in relative abundance. Only taxa that are determined to be associated with NGU receive a non-zero beta coefficient. Compositional lasso does not yield p-values Presence and concentrations of MP, HI and UU were measured using targeted qPCR in 431 of 434 men with sufficient remaining DNA. Presence of MP (OR=8.3; 1.98-73.60) and HI (OR=9.8; 2.99-50.22) were significantly associated with NGU, including idiopathic NGU (OR=14.9; 3.41-135.15 and OR=20.24; 5.97-105.57, respectively), as were higher concentrations (p<0.03 for both). Neither presence nor concentrations of UU were associated 135 with NGU (Table 6). Target validation by qPCR of *H. influenzae* and *M. penetrans* showed separation between NGU- and NGU+, while this was not observed for *U. urealyticum*. Higher relative abundances of *Haemophilus influenzae* (P=0.0139) and *Mycoplasma penetrans* (P=0.0095) were positively associated with idiopathic NGU in MSM, while *H. influenzae* was positively associated with idiopathic NGU in MSW (0=0.0184). In analyses stratified by sex of sex partner, presence of HI was significantly associated with NGU in MSM (p=0.036) and in MSW (p<0.001), but higher concentrations of HI were only associated with NGU (p=0.025) including idiopathic NGU (p=0.03) among MSM (Table 7). Presence, but not concentrations, of MP was associated with NGU and idiopathic NGU among MSM (p<0.01 for both), but this was not observed among MSW. Most cases with HI or MP had mono-infections (12% and 6.8% respectively); HI was detected in two cases with CT and two cases with TV, while MP was detected in four cases with CT. The model also identified bacterial species that were negatively associated with NGU in MSM and MSW. Notably, *Lactobacillus iners* was negatively associated with idiopathic NGU in MSW (p=−0.000690) but not MSM (Table 5).

Characteristics associated with MP (Table 8), HI (Table 9), and UU (Table 10) were evaluated separately by sex of sex partners. No sociodemographic (age, race, ethnicity, education), sexual behavior (number sex partners, sexual exposures, condom use), or STD history (NGU, GC, CT) characteristics were associated with either HI or MP. With two exceptions, none of these characteristics were associated with UU. Among MSM, UU was significantly associated with insertive anal sex (77% vs. 54%, p=0.001) and inversely associated with consistent condom use (8% vs. 25%, p=0.026). Among MSW, UU was significantly less common in those with HI (p=0.031).

Given the absence of associations with other pathogens and potential risk factors, no multivariable models were developed.

The association between potential pathogens and NGU among 431 subjects enrolled in the study are shown in Table 11.

The association between potential pathogens and NGU among MSW and MSM with idiopathic NGU is shown in Table 12.

Example 2

*Mycoplasma penetrans* QPCR Assay

This assay was designed for use in detecting and diagnosing *Mycoplasma penetrans* in men with urethritis. Primers targeting *Mycoplasma penetrans* 16S rRNA gene were designed.

```
Primers:
                                        (SEQ ID NO: 1)
Forward: 5'-CGGACGAAGCACTTGTGCTT-3'

(SEQ ID NO: 2)
Reverse: 5'-TTTTCTCATGCGATAGTAATGTCC-3'

Probe:
                                        (SEQ ID NO: 3)
5'-TAACATACCTTTTAGTGGGGATAACTGGTTG-3'
```

Reaction Conditions:
Run on Step One

| 50° C., 2:00 min | |
|---|---|
| 95° C., 10 min | |
| 95° C., 15 sec | x45 cycles |
| 55° C. Anneal. 39 sec | x45 cycles |
| 72° C. Extend. 30 sec | x45 cycles |

The PCR mastermix (20 uL reaction) for detecting and diagnosing *Mycoplasma penetrans* in men with urethritis is shown in Table 13. Increased primer, probe, Taq, and Mg concentrations were used, as FAST mix did not produce efficient amplification.
Standards were diluted in 0.1% TX. *Mycoplasma penetrans* plasmid of target DNA was used for standards. Three 2.5 copy standards were run to ensure detection at lower limit.
Specificity:
1E4 pg gDNA was loaded per reaction for the bacteria listed in Table 14.
1E6 copies/rxn of the plasmids listed in Table 15 were added.

*Mycoplasma penetrans* DNA concentrations were measured with a TaqMan based qPCR assay targeting the *Mycoplasma penetrans* 16S rRNA gene with primers (56F 5'-CGGACGAAGCACTTGTGCTT-3' (SEQ ID NO:1) and 184R 5'-TTTTCTCATGCGATAGTAATGTCC-3') (SEQ ID NO:2) and hydrolysis probe (5'-FAM-[TAACATACCTTT-TAGTGGGGGATAACTGGTTG (SEQ ID NO:3)]-TAMRA-3'). Reactions underwent 45 cycles of amplification on the QuantStudio™ 6 Flex Real-Time PCR System with a 95° C. melt for 15 seconds, a 55° C. anneal for 39 seconds, and a 72° C. extension for 30 seconds. Core reagents were supplied by Applied Biosystems (Carlsbad, CA) and master mixes contained buffer A (1×), deoxynucleotide triphosphates (1 mM), magnesium (4 mM), AmpErase uracil-N-glycosylase (0.05 U) and AmpliTaq Gold polymerase (0.9 U) per reaction. Primers were added at 1.2 µM per reaction and probe at 200 nM per reaction. *Mycoplasma penetrans* 16S rRNA gene plasmid standards were run for each reaction with a lower limit of detection of 2.5 gene copies/µL DNA.

Example 3

*Haemophilus influenzae* QPCR Assay

This assay was designed for use in detecting and diagnosing *Haemophilus influenzae* in men with urethritis. Primers targeting *Haemophilus influenzae* 16S rRNA gene were designed.

```
Primers:
                                        (SEQ ID NO: 4)
Forward: 5'-GCCCGTAGCTAACGTGATAAATCG-3'

(SEQ ID NO: 5)
Reverse: 5'-AAGCTCATCTCTGAGCTCTTCTTAGG-3'

Probe:
                                        (SEQ ID NO: 6)
5'-CAAGCGGTGGAGCATGTGGTTTAATT-3'
```

Reaction Conditions:
This assay is FAST compatible, but could also be run at ramping speed
Run on StepOne and QuantStudio6

| 50° C., 2:00 min | |
|---|---|
| 95° C., 20 sec | |
| 95° C., 2 sec | x45 cycles |
| 55° C., 20 sec | x45 cycles |
| 72° C., 20 sec | x45 cycles |

The PCR mastermix (15 uL reaction) for detecting and diagnosing *Haemophilus influenzae* in men with urethritis is shown in Table 16. Standards were diluted in 0.1% TX. *Haemophilus influenzae* plasmid was used for standards. Plasmid was generated from *Haemophilus* isolate using 957F-1127R and the Zero Blunt TOPO PCR Cloning Kit from Invitrogen.
Sensitivity:
The following isolates were detected with this assay:
*Haemophilus influenzae*
Specificity:
The isolates listed in Table 17 were loaded at 1E4 pg genomic DNA per qPCR reaction. All were (undetected).

Additionally, the following plasmids were loaded at 1E6 copies per reaction:
1. vaginae
2. BVAB1
3. BVAB2
4. BVAB3
5. *Eggerthella* sp.
6. *G. vaginalis*
7. *L. crispatus*
8. *L. iners*
9. *L. jensenii*
10. *L. gasseri*
11. *Leptotrichia*
12. Mega 1,2
13. *Mobiluncus curtisii*
14. *Mobiluncus mulieris*
15. *P. amnii* (new one created)
16. *P. buccalis* (new one created)
17. *P. timonensis* (new one created)
18. TM7
19. *Mycoplasma hominis*
20. *Gemella assacharolytica*
21. *Dialister micraerophilus*
22. *Dialister* sp Type 2
23. *Aerococcus christensenii*
24. *E. coli* 16S
25. Mega els
26. *Sneathia* sanguinegens
27. *U. parvum*
28. *U. urealytica*
29. *H. aegyptius*
30. Porphoromonas type I
31. *H. parainfluenzae*

*Haemophilus aegyptius* was amplified at CT 16.64.
In total 82 isolates and plasmids have been tested.

Example 4

Therapeutic Interventions for NGU Guided by *H. influenzae* and *M. penetrans*

The studies outlined in Examples 1-3 have linked both *Haemophilus influenzae* and *Mycoplasma penetrans* to idiopathic NGU in men. Identification of these bacterial pathogens in urethral samples from men would allow appropriate antibiotic treatment for these infections. For instance, the most appropriate treatment for urethritis caused by *Trichomonas vaginalis* would be metronidazole if detected in the NGU panel, whereas the most appropriate treatment for *H. influenzae* would be ceftriaxone, doxycycline or ciprofloxacin (see, Deguchi et al. (2017), J Infect Chemother. 23(11):804-807 and Ito et al. (2017), Sex Transm Dis. 44(4):205-210, both of which are incorporated herein by reference in their entirety for their teachings regarding the same) and the most appropriate treatment for *M. penetrans* would be azithromycin, doxycycline, ciprofloxacin or levofloxacin (see, Hayes et al. (1995), Antimicrob Agents Chemother. 39(6):1386-7 and Poulin et al. (1994), J Clin Microbiol. 32(4):1101-3, both of which are incorporated herein by reference in their entirety for their teachings regarding the same). Knowing the etiological agent of NGU facilitates the selection of the most appropriate antibiotic. Furthermore, the PCR assays described herein can be used to monitor the eradication of pathogens and establish test of cure. A table of drugs indicated for use with NGU and that would be selected based on whether or not *H. influenzae* or *M. penetrans* is present in the sample are outlined in Table 32 Emerging longitudinal data on how antibiotic therapy affects concentrations of *H. influenzae* and *M. penetrans* in the male urethra and how these kinetics are linked to clinical cure is being collected.

Example 5

Association Between Vaginal Bacteria and HIV Acquisition Risk Among African Women Participating in the Voice Study The VOICE (MTN-003) study was a randomized, placebo-controlled, Phase IIB trial of daily oral versus vaginal tenofovir-based pre-exposure prophylaxis for HIV. Vaginal swabs were collected routinely at 6 month intervals or when pelvic examination was indicated. Cases and controls were matched by study arm and site.

Vaginal bacteria associated with HIV acquisition risk among South African women participating in the VOICE study were screened using a sequential PCR approach. Vaginal swabs from 150 female subjects (177 visits) ≤6 months prior to HIV seroconversion (cases) were analyzed. Swabs from 436 female subjects who remained HIV uninfected (530 visits) were used as controls.

Figure 7:
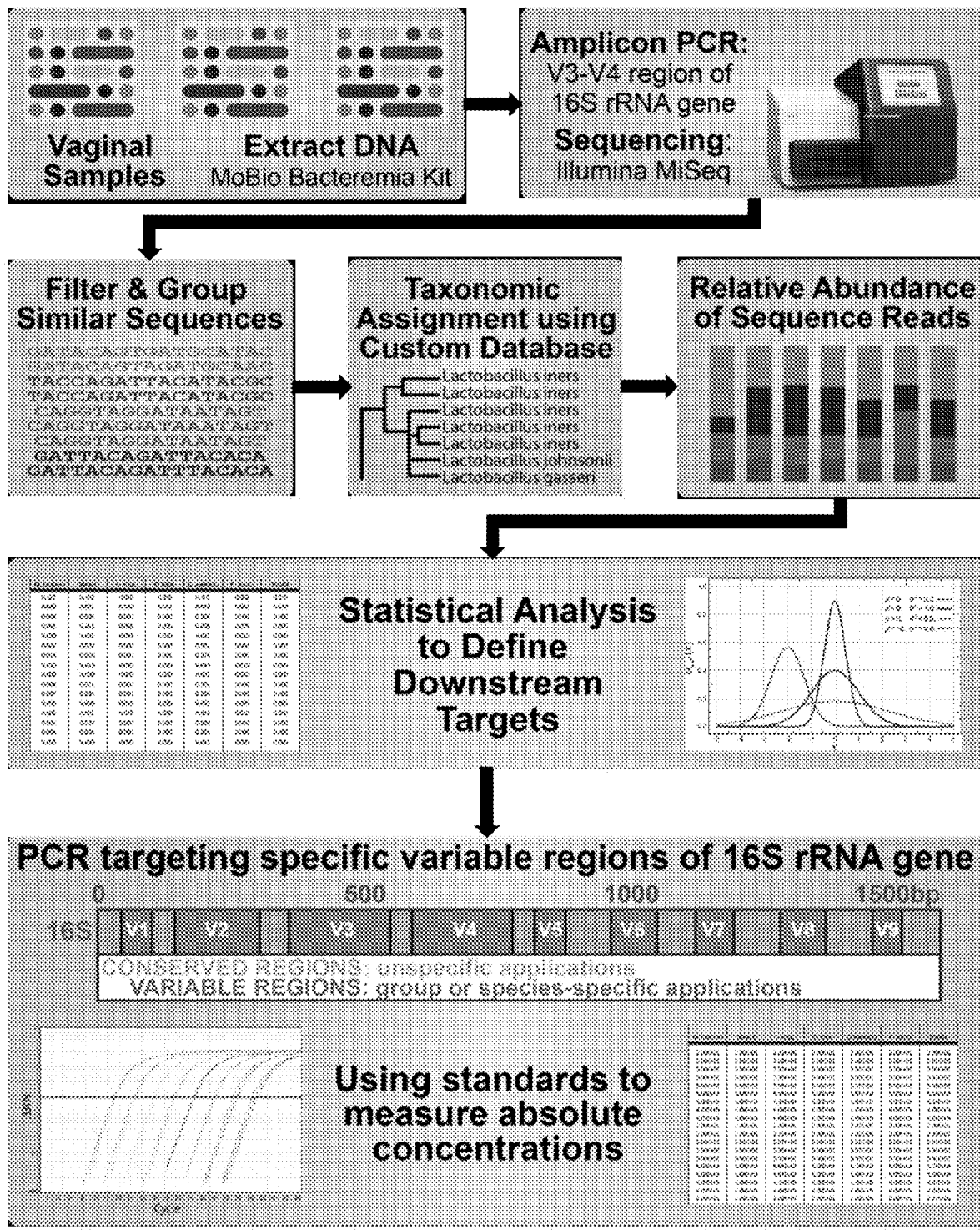
FIG. 7 shows a molecular workflow to identify bacteria associated with HIV acquisition risk.

Vaginal microbiota were characterized using 16S rRNA gene PCR and sequencing for each subject. DNA was subjected to broad-range PCR and sequencing. Logistic regression with case-control status as the outcome and relative abundance of bacterial taxon as exposure was performed to select bacterial taxa for qPCR. Taxa with a score statistics p-value ≤0.1 and an overall prevalence of >5% were selected and Generalized Estimating Equation (GEE) models were run on these taxa to obtain Odds Ratios of the association between their relative abundance and case-control status. Concentrations of selected bacterial taxa were measured using targeted qPCR assays. The relationship between bacterial concentrations and HIV risk was analyzed using GEE models adjusted for potential confounders. A Benjamini-Hochberg False Discovery Rate (FDR) of 0.1 was applied. A molecular workflow to identify bacteria associated with HIV acquisition risk is shown in FIG. 7.

Figure 8:
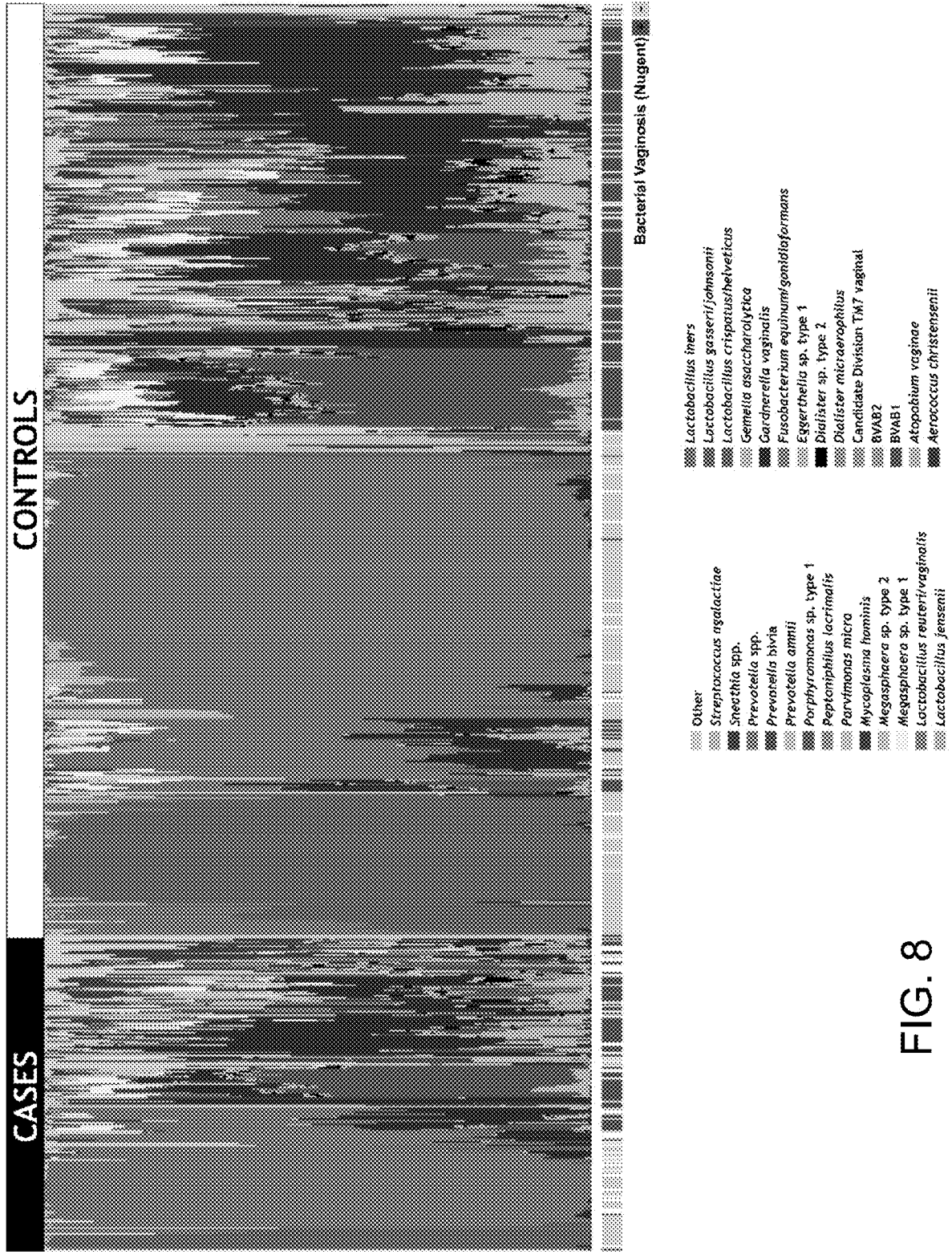
FIG. 8 illustrates bacterial communities in 177 subjects who acquired HIV (cases) and 530 subjects who remained HIV negative (controls), as described in Example 5.

Bacterial communities in 177 subjects who acquired HIV (cases) and 530 subjects who remained HIV negative (controls) are illustrated in FIG. 8. Each stacked bar represents the vaginal bacterial community in a single participant. Taxa less than 1% abundance shown in the other category. BV was diagnosed using Nugent criteria. Gray indicates BV negative (Nugent Scores 0-6) and red indicates BV positive (Nugent Scores 7-10).

Hierarchical clustering of vaginal bacterial communities showed that women who acquired HIV (cases) had similar bacterial communities to women who did not acquire HIV (controls). Analyses of individual taxa may help identify individual bacteria associated with increased risk. Some women with *Lactobacillus crispatus*-dominant communities also acquired HIV.

Figure 9:
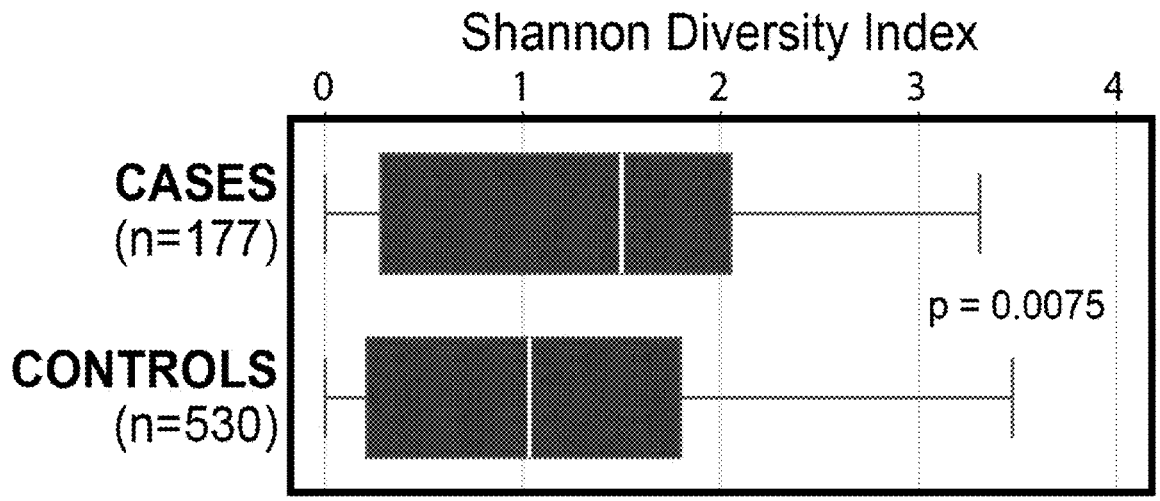
FIG. 9 provides the alpha diversity of vaginal bacterial as described in Example 5.

Vaginal bacterial diversity among cases was higher than controls (p=0.0044). Alpha diversity is illustrated in FIG. 9. Vaginal bacterial diversity as measured by Shannon Diversity Index was higher among cases compared to controls.

Prevalence of bacteria selected for qPCR is shown in Table 28. Analyses of relative abundance data of individual bacterial taxa identified 12 bacterial taxa that have not been previously described. Concentrations of six of 12 taxa were measured using taxon-specific qPCR. Five of six bacterial taxa were significantly associated with increased risk for HIV acquisition. These include bacterial vaginosis-associated bacterium 2 (BVAB2; adjusted odds ratio (aOR)=1.57;

95% CI 0.97, 2.56), Candidate Division vaginal TM7 (aOR=2.04; 95% CI 1.14, 3.65), *Prevotella amnii* (aOR=1.53, 95% CI 0.95, 2.46), *Porphyromonas* Type 1 (aOR=2.04, 95% CI 1.27, 3.28), and *Peptoniphilus lacrimalis* (aOR=1.55, 95% CI 0.98, 2.44). *Dialister micraerophilus* was not associated with HIV risk.

Figure 10:
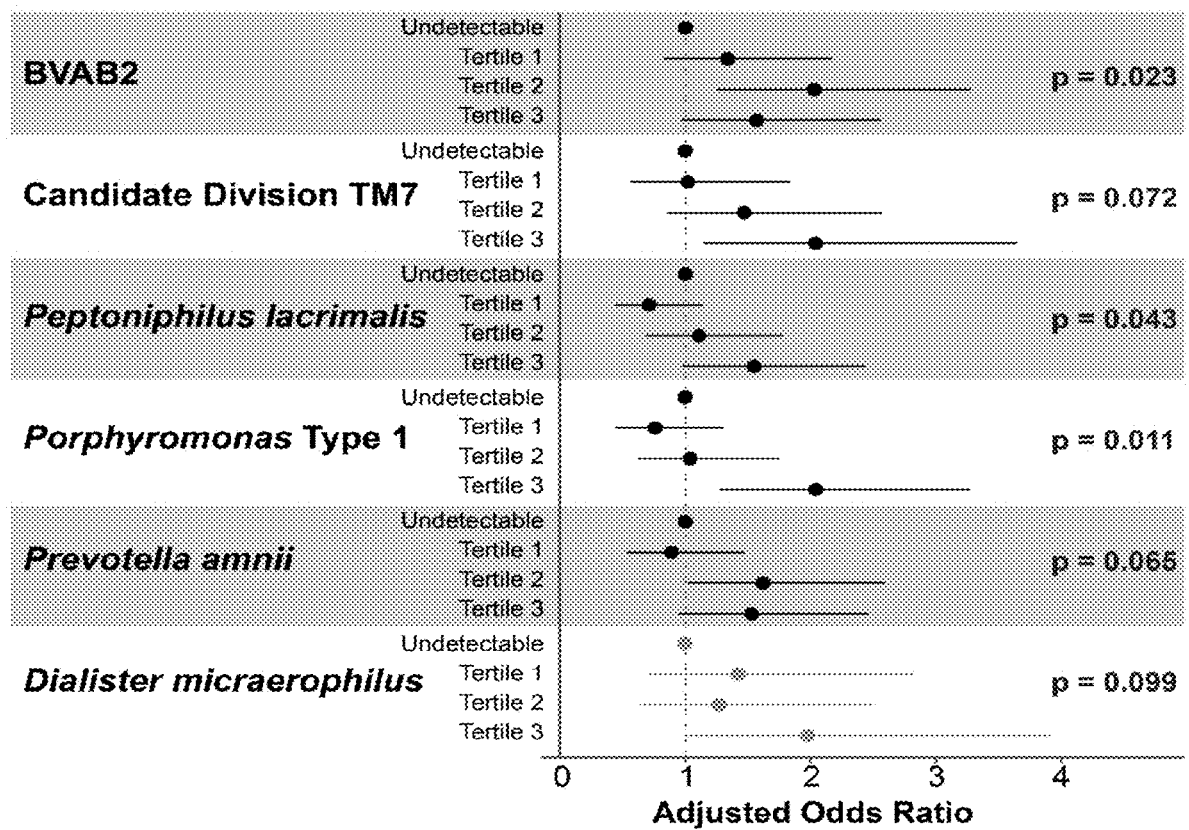
FIG. 10 provides adjusted odds ratios displaying the association between bacterial concentrations and HIV acquisition.

Adjusted odds ratios displaying the association between bacterial concentrations and HIV acquisition are illustrated in FIG. 10. Median values with 95% confidence intervals are shown. Each bacterial taxon was analyzed as a four category exposure: undetectable (referent, first, second and third tertiles). A single joint p-value was used to test significance. Models were adjusted for multiple confounders including age, contraception method, number of sex partners, frequency of sex, and report of condom use.

Example 6

Updated Analysis of Quantitative PCR Data (Concentrations of Bacteria of Interest)—Bacteria Associated with HIV Acquisition Risk Association Between Vaginal Bacteria and HIV Acquisition Risk Table 29 describes demographic and sexual behavior variables for 150 cases and 436 controls.

Table 30 shows unadjusted and adjusted odds ratios showing the association between vaginal bacterial quantity by qPCR and HIV acquisition in 177 pre-seroconversion visits (at most 6 months prior) from 150 women who became HIV infected versus 531 visits from 436 women who remained HIV uninfected.

Example 7

Primers and Probes for Vaginal Microbiome Assay

Table 1 provides primers sets, probes, conditions, cycling/Taq concentrations for an exemplary vaginal microbiome assay.

Example 8

Periodic Presumptive Treatment (PPT) with Metronidazole to Reduce Abundance of Vaginal Bacteria Associated with HIV Risk Bacterial vaginosis is highly prevalent among women of reproductive age. In parts of sub-Saharan Africa, prevalence rates can exceed 50%. Epidemiological studies demonstrate that BV is associated with increased HIV risk. Further, studies using molecular methods have associated specific vaginal bacteria with HIV risk. Seven vaginal bacteria were identified in Example 5 that showed concentration-dependent associations with HIV acquisition risk in East African women. These findings were validated in a nested case control study of 586 mostly South African women participating the VOICE trial of daily oral versus vaginal tenofovir-based pre-exposure prophylaxis for HIV.

Treatment strategies to reduce BV among women who frequently experience BV have been investigated. The Preventing Vaginal Infections (PVI) Trial was a randomized trial of monthly periodic presumptive treatment (PPT) of high dose intravaginal metronidazole 750 mg plus miconazole 200 mg versus placebo for preventing vaginal infections. The PVI trial noted a reduction in BV by 35% compared to placebo and a reduction in the concentrations of bacteria specifically associated with BV including BV associated bacterium 1 (BVAB1), BVAB2, *Megasphaera* spp., *Atopobium vaginae* and *Sneathia* spp. However, the targeted approach to measure concentrations of specific bacteria did not assess the impact of PPT on the vaginal microbiota and specific bacteria associated with HIV acquisition. This study describes the impact of PPT on vaginal bacterial communities and specific bacteria that were previously associated with HIV acquisition risk.

Study Population

Figure 11A:
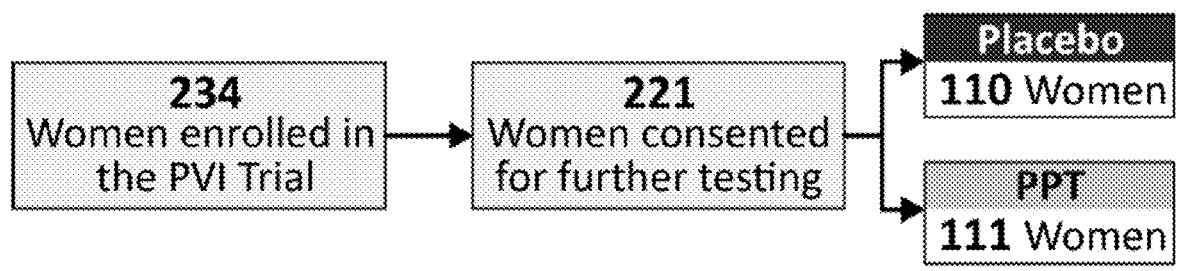
FIG. 11A and FIG. 11B show PVI Trial enrollment as described in Example 8, in which subjects received PPT (n=111) or Placebo (n=110) (FIG. 11A), and specimen collection (FIG. 11B).

The study population consisted of HIV-negative, non-pregnant women enrolled at 4 sites between 2011 and 2012. Two sites were located in Nairobi, Kenya and other sites included Mombasa, Kenya and Birmingham, Alabama, USA. Of the 234 women enrolled in the PVI Trial, 221 consented for further testing (FIG. 11A, 110 women received the Placebo and 111 received PPT). At the time of screening, eligible participants were positive for a vaginal infection, including one or more of Bacterial vaginosis, *Trichomonas vaginalis* or Vulvovaginal candidiasis. Participants were randomized to PPT or placebo 5 consecutive nights each month for 12 months.

Microbiota Analyses

Figure 11B:
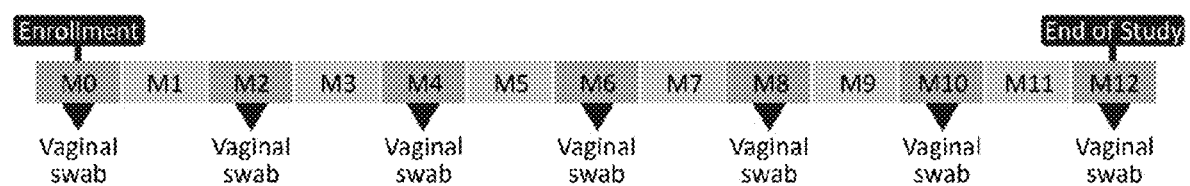

Vaginal fluid specimens were collected at enrollment and every other month DNA was subjected to broad range PCR and sequencing (FIG. 11B). Using all follow up visits, correlation coefficients were calculated between treatment groups and individual bacterial taxa to generate measures of strength of association. Generalized Estimating Equation (GEE) models were used to compare relative abundances of bacterial taxa between the PPT and placebo groups. These models were applied to taxa that had an absolute value of correlation with treatment group of ≥0.8. A targeted analysis was also conducted using GEE models to examine the effect of PPT on bacteria previously associated with HIV risk.

Figure 12:
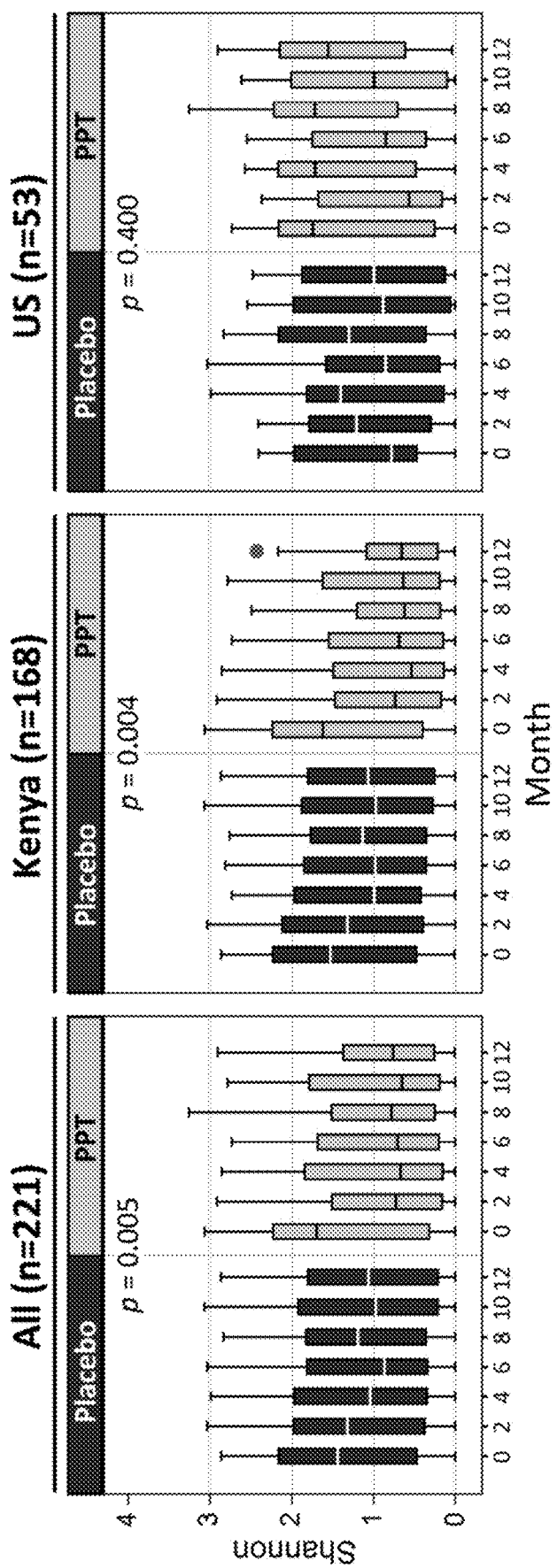
FIG. 12 illustrates alpha diversity between PPT and placebo arms, stratified by country.

Alpha diversity was calculated using the Shannon Diversity Index (SDI), as shown in FIG. 12. There was no difference in SDI at baseline between PPT and placebo arms (p=0.4). Vaginal bacterial diversity (SDI) was lower among women in the PPT arm (p=0.005) when compared to the placebo. In analyses stratified by country, significant decreases in SDI were noted among Kenyan women (p=0.004) but these differences were not seen in US women (p=0.4) when compared to the placebo.

Figure 13:
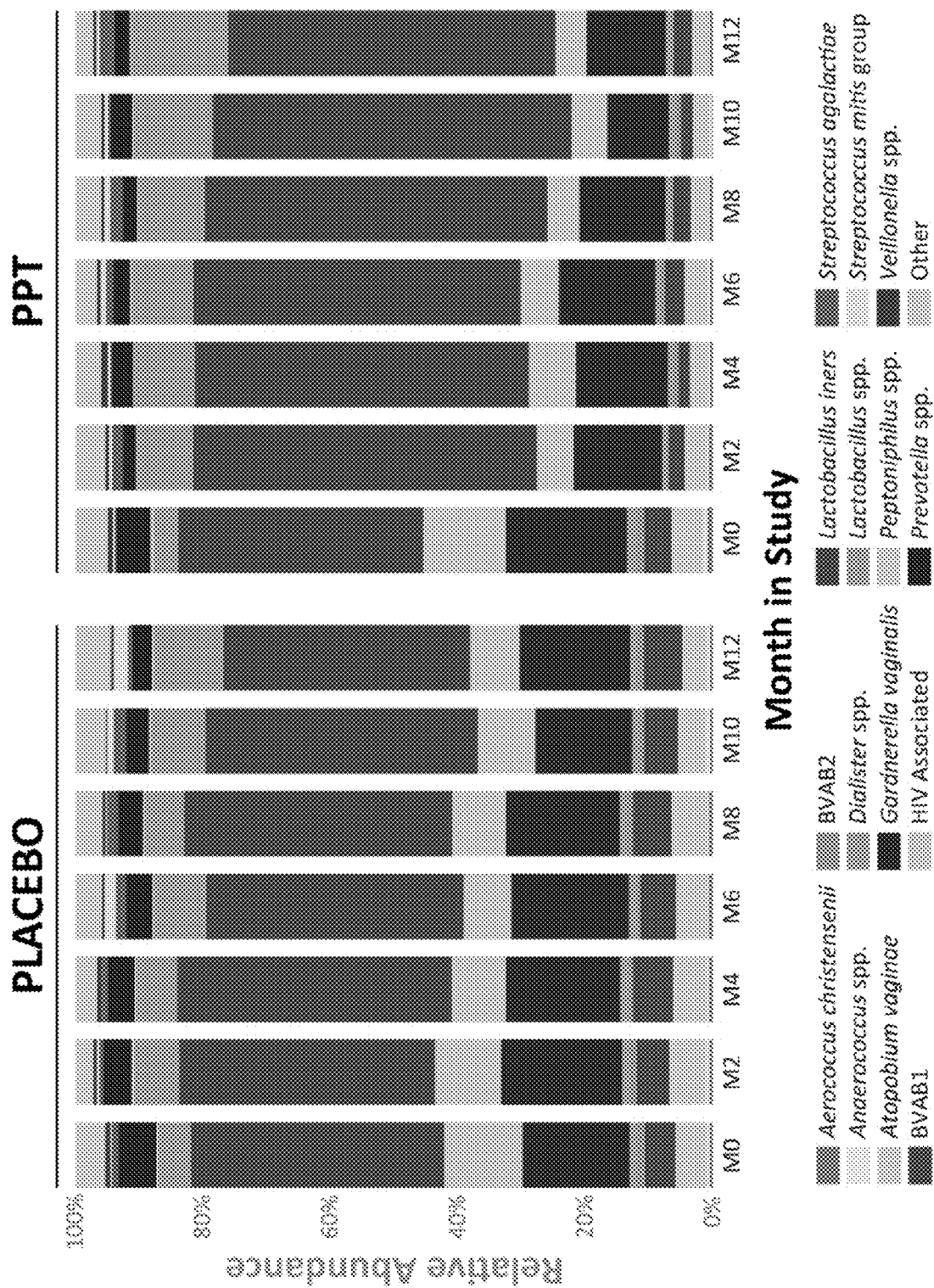
FIG. 13 shows vaginal bacterial community composition in women from all study sites who were randomized to the Placebo and PPT study arms.

The composition of the bacterial community was analyzed in 221 women from all study sites who were randomized to the Placebo and PPT study arms, representing 1456 samples (FIG. 13). An increase in the relative abundances of

Figure 14:
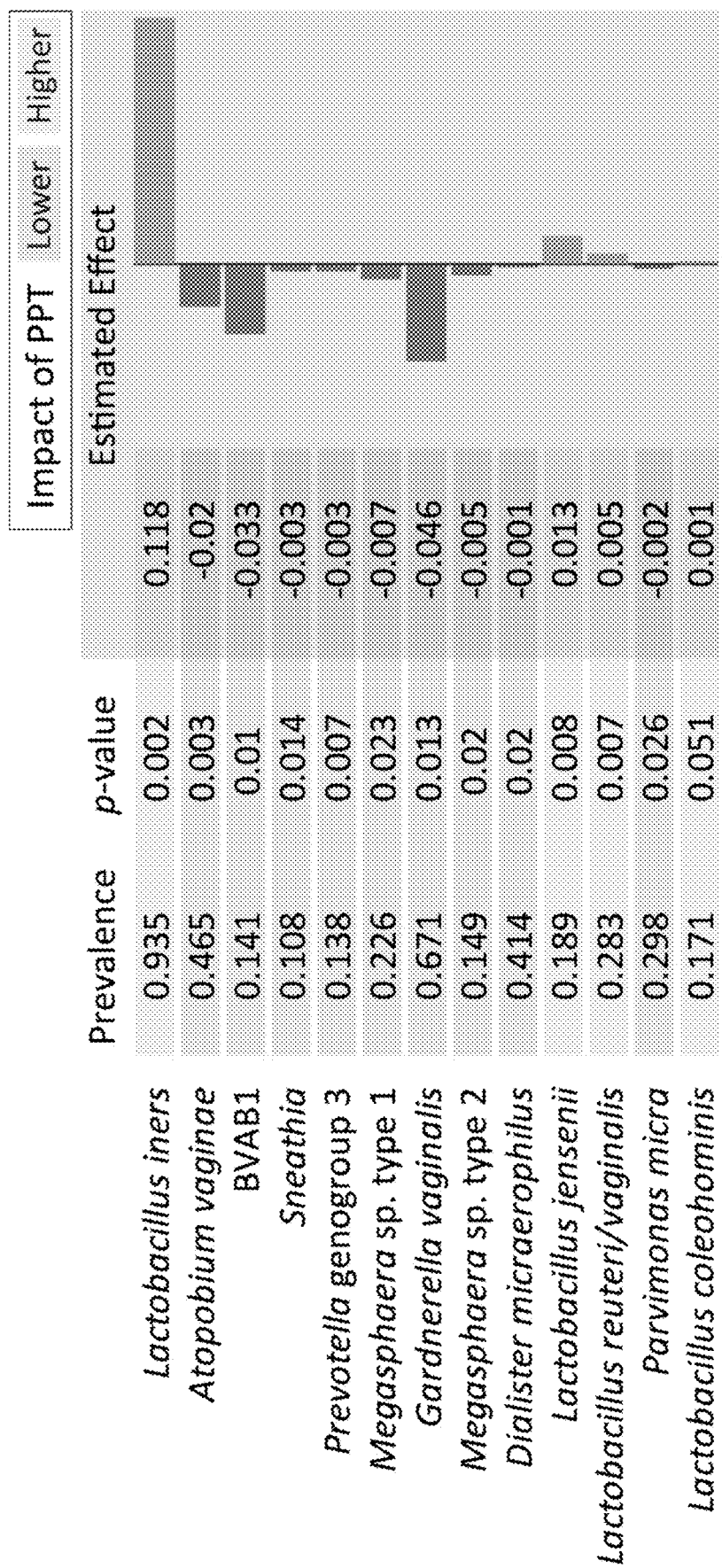
FIG. 14 shows the impact of PPT on individual bacterial taxa in all study participants.

*Lactobacillus iners* and non-*iners* lactobacilli was noted among women in the PPT arm. Decreases in the relative abundance of BVAB-1, HIV-associated bacteria, and *Prevotella* spp were noted in the PPT arm. The impact of PPT on individual bacterial taxa in ALL study participants was assessed in FIG. 14. *Lactobacillus* species including *L. iners, L. jensenii*, and *L. vaginalis* were significantly increased in relative abundance among women in the PPT arm at follow up visits compared to the baseline visit. Several BV associated bacteria were significantly lower among women in the PPT arm at follow up visits compared to baseline.

Figure 15:
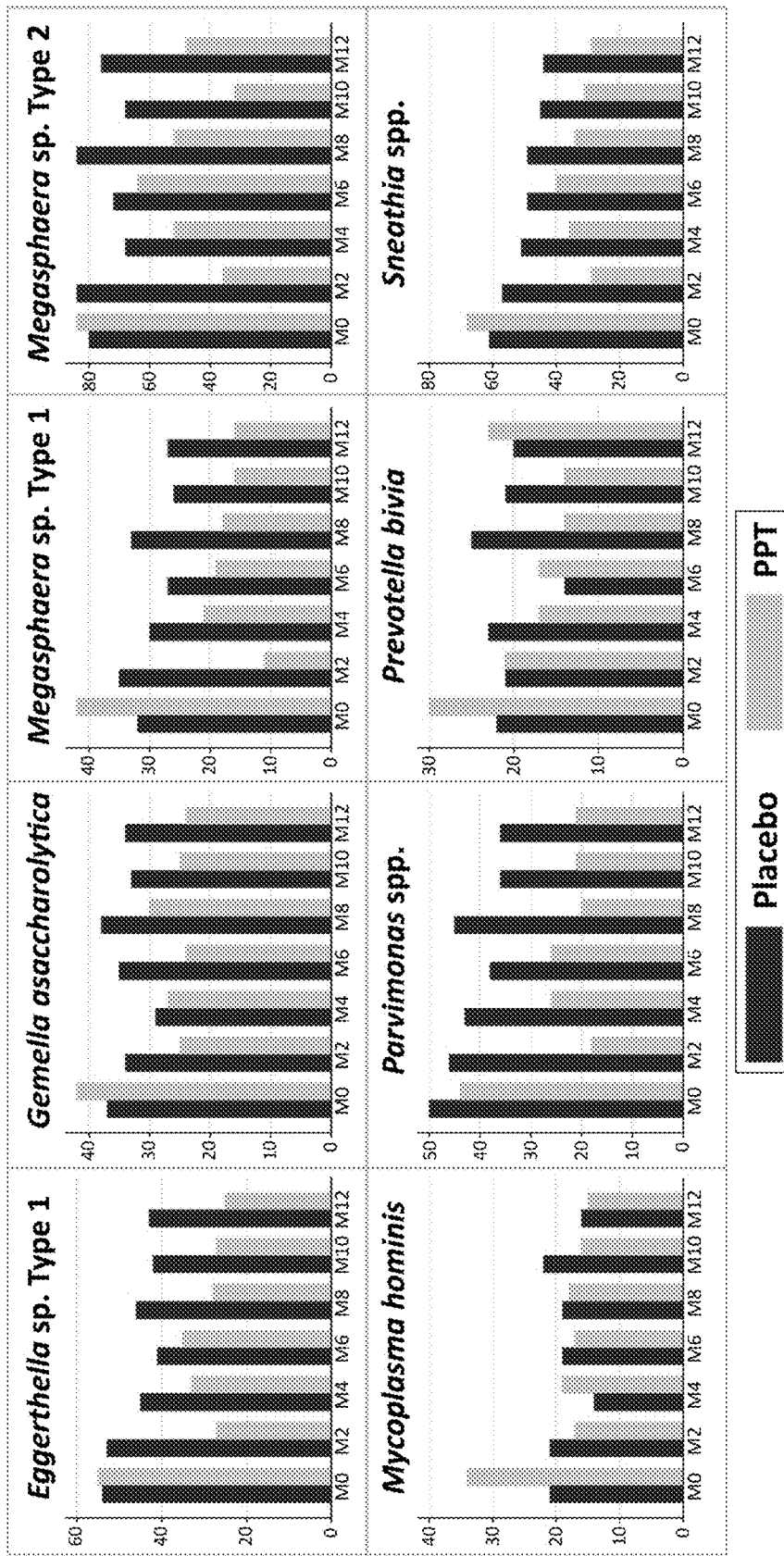
FIG. 15 shows HIV-associated bacterial taxa detection by study arm.
Figure 16:
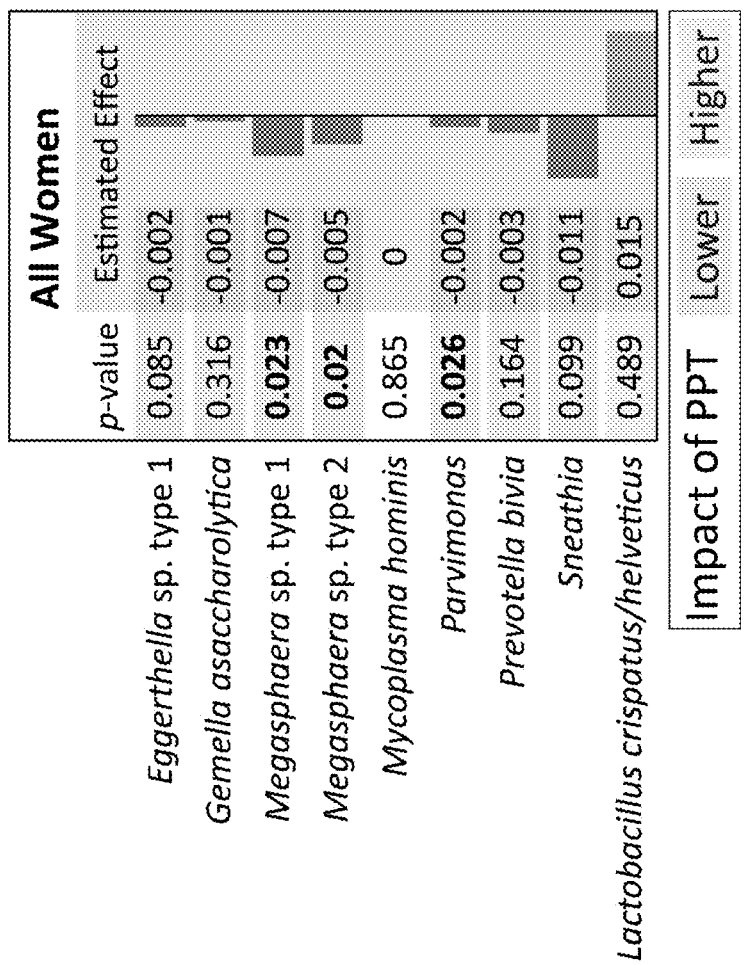
FIG. 16 shows the impact of PPT on abundance of HIV-associated bacterial taxa.
Figure 16:
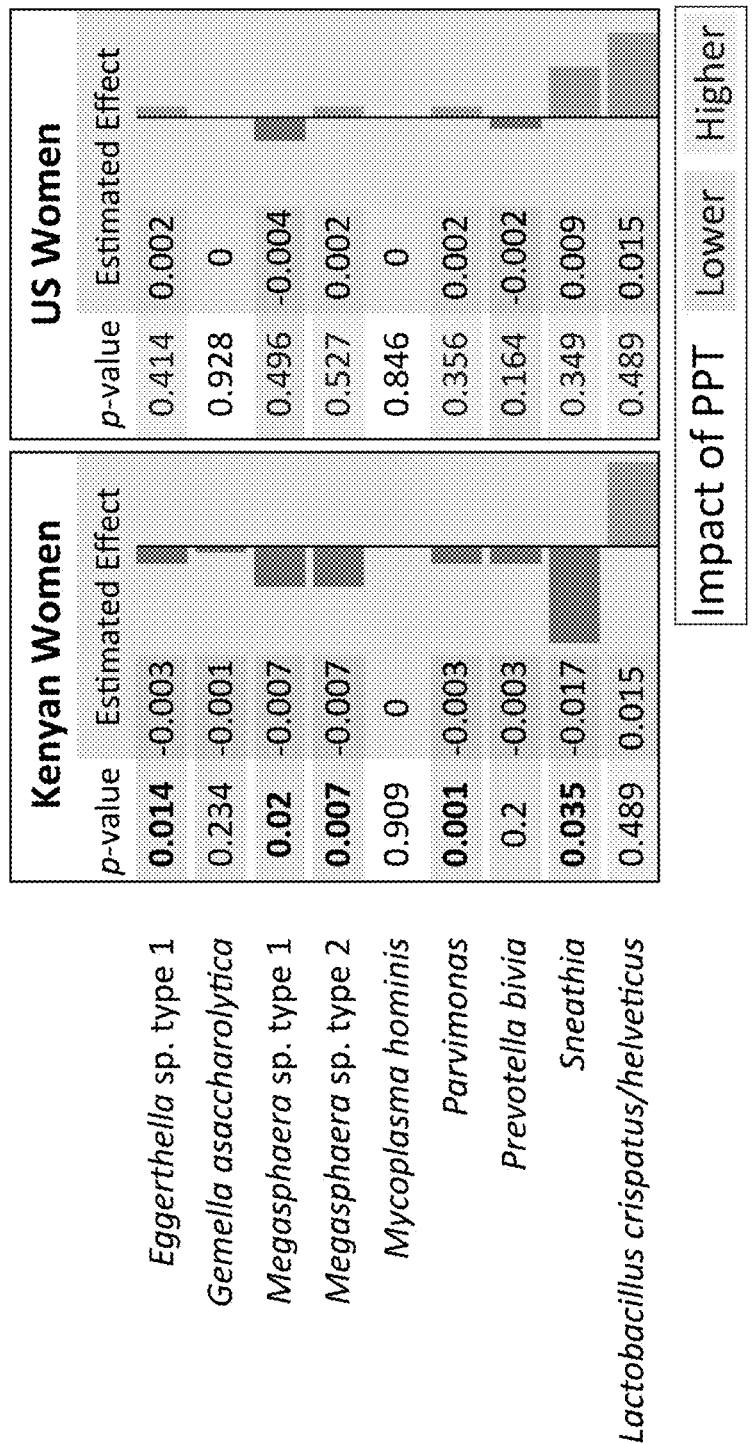

HIV-associated bacterial taxa were characterized as detected by study arm (FIG. 15). All HIV associated bacterial taxa were detected in fewer women in the PPT arm at the end of the study compared to women in placebo arm. The impact of PPT on HIV-associated bacterial taxa was evaluated, as shown in FIG. 16. Relative abundances of *Megasphaera* sp. types 1 ($p=0.023$) and 2 ($p=0.02$) and *Parvimonas* spp. ($p=0.0026$) were significantly lower among all women in the PPT arm (combined analysis of all follow up visits) compared to the placebo arm. In analyses stratified by country, Kenyan women in the PPT arm had significantly lower relative abundances of *Eggerthella* sp. type 1 and *Sneathia* spp. in addition to the bacteria noted above when compared to the placebo. These differences were not noted among US women.

Use of monthly PPT for a year promoted the colonization of *Lactobacillus* species while reducing the colonization of bacteria associated with HIV acquisition. Geographical differences in the vaginal microbiota, differences in adherence to the study product or vaginal hygiene practices may have contributed to the differential impact of PPT among women in Kenya and the US. PPT could play an important role in reducing the risk for HIV acquisition in African women.

Example 9

PPT & Suppressive Antibiotics Targeting Suboptimal Vaginal Bacteria to Improve Genital Mucosal Markers of HIV Susceptibility Screening HIV seronegative female sex workers (FSW) are recruited from a long-term open cohort study and meet inclusion show in Table 31. Subjects without current complaints of abnormal vaginal discharge quantity, color, or odor are recruited. Subjects have blood and urine collected for rapid HIV and pregnancy testing (urine β-hCG). If a subject is HIV-positive or pregnant, screening procedures are concluded. For all other subjects, a standardized interview and pelvic exam with sample collection is performed to assess eligibility, and they are invited to return for lab results and possible enrollment. Screening HIV results are considered valid for 28 days.

Randomization

Randomization takes place after enrollment sample collection. The subjects are divided into three groups, a control arm, a PPT arm, and a suppression arm. The control arm is observed. The PPT arm is instructed to insert a 5 gram dose of metronidazole (MTZ) gel intravaginally just prior to going to sleep for five consecutive nights each month. If one or more doses are missed, continue using the intravaginal gel daily until five doses are completed. The suppression arm is instructed to administer five consecutive doses in month one (same as PPT arm), and to continue using 5 grams intravaginally just prior to going to sleep twice per week on nonconsecutive days.

Subjects in the treatment arm are provided with study product and counseled about its storage and use. Instructions include refraining from intravaginal practices such as vaginal washing for at least 48 hours following product use. All participants are asked to return for a follow-up visit during the next week to assess adherence to the protocol, and instructed to return at any time if they are symptomatic.

Subjects that develop symptomatic genital tract infections or have an etiological STI diagnosis like gonorrhea or *Chlamydia* will be treated according to standard of care regardless of study arm.

Follow-Up Visits

Follow-up Visits are targeted for mid-menstrual cycle at one and two months following enrollment. A structured interview is conducted addressing adherence and collecting time-updated information on time-varying factors measured at the Enrollment Visit such as sexual behaviors and intravaginal practices. Study product is dispensed to women in the active treatment arms after confirming a negative urine β-hCG test.

The effect of cyclic variations in the genital microbiota, immune milieu, and epithelium is minimized by avoiding sample collection during menses and scheduling visits as close as possible to the interval between 12 and 14 days before the expected start of the next menstrual period.

End of Study Evaluation

The End of Study Evaluation occurs three months after enrollment. A structured interview is conducted to collect time-updated information, as detailed for Follow-up Visits. Additional questions examine perceptions, acceptability, barriers and facilitators to using each treatment regimen and the observational control. These data are utilized alongside the other adherence measurements to gain a more holistic understanding of adherence. Rapid HIV testing and a urine pregnancy test are repeated. A blood sample is collected for estradiol and progesterone testing. A general physical and pelvic examination is performed with sample collection as in the Enrollment Visit.

Post-Trial Visits and Samples

Subjects in the PPT and suppression arms continue monthly follow-up visits for an additional three months after the End of Study Visit. Subjects completing the trial in each active arm are randomly assigned to discontinue or continue the regimen. To reduce burden on participants, only monthly visits are conducted during this phase of the study. At the Post-trial Evaluation, participants complete an interview, examination, and sample collection following the same procedures as the End of Study Evaluation.

Laboratory Methods

Several lab procedures are performed following existing SOPs including rigorous internal quality control (GCLP, continuous quality improvement, blinded validation) and external quality assurance (commercial panels). Quantitative PCR is performed by staff blinded to study arm until all lab work is complete.

Quantitative PCR Assays for Vaginal Bacteria

Swabs for bacterial qPCR are batched and transported on dry ice. A Qiagen DNA extraction kit is used to extract DNA from vaginal fluid swabs. This protocol uses bead beating and chaotropic lysis to break apart bacterial cells and recover DNA free of PCR inhibitors. Purified DNA is used for bacterium-specific 16S rRNA gene qPCR assays to determine the presence and concentrations of vaginal bacteria. These assays were developed using primers and probes that target taxonspecific regions of the 16S rRNA gene, and employ a 5' exonuclease (TaqMan) probe capable of detecting 2.5 gene copies of the target plasmid in a PCR without cross-reaction when any of 50 non-target bacterial species or plasmids are added to the PCR at high concentration (1 million copies). Accordingly, these qPCR assays are highly sensitive and specific for the intended bacterium and provide an accurate measurement of bacterial concentrations. A panel of >25 qPCR assays for vaginal bacteria are available. The analysis will be focused on 14 key species that have been associated with increased HIV risk. Standard exogenous jellyfish qPCR amplification control will be employed to assess for PCR inhibitors, as previously described.

Power and Sample Size

The primary analyses compare each active arm to the control arm. In the mediation analysis, a principal component analysis (PCA) is performed to reduce the dimensionality of the qPCR data from 14 bacterial taxa, many of which are correlated with one another. Next, the presence and magnitude of mediation of each intervention effect is examined, compared to control, by one or more of the principal components, each representing concentrations of a distinct set of correlated bacterial taxa.

Example 10

Antibiotics Targeting Vaginal Bacteria to Decrease HIV Acquisition Risk

Most of the vaginal bacteria that are associated with increased risk of HIV acquisition in women are susceptible to nitroimidazole antibiotics such as metronidazole (topical gel-metrogel, oral, or intravenous metronidazole), tinidazole, or secnidazole. Women who have bacterial vaginosis (BV) and are treated with either oral metronidazole or intravaginal metronidazole gel experience rapid declines in concentrations of these vaginal bacteria linked to HIV risk. These data were generated using vaginal samples collected from women enrolled in studies of BV treatment. Both broad-range 16S rRNA gene PCR and species-specific quantitative PCR assays have demonstrated that the abundance and concentrations of these vaginal bacteria rapidly decline with antibiotic therapy (unpublished data), suggesting an approach for reducing risk of HIV acquisition in women by reducing concentrations of vaginal bacterial linked to risk. Other published data also support the view that metronidazole therapy results in rapid declines in bacterial concentrations of relevant bacteria (see, Mayer et al. (2015), J Infect Dis. 212(5):793-802 incorporated herein by reference in its entirety for the teachings regarding the same). Clindamycin and other antibiotics may also have activity since many of the high-risk bacteria are anaerobes susceptible to anti-anaerobe antibiotics like clindamycin. Clindamycin is one antibiotic used to treat BV. Another potential intervention to alter the vaginal microbiota and influence risk of HIV acquisition is use of hormonal contraceptives. Some HIV high-risk bacteria decline in the vagina with use of a contraceptive vaginal ring (unpublished data). Taken together, these data suggest that women at elevated risk of HIV infection can be identified using the diagnostic approaches described in this application, then risk of infection may be modulated using antibiotic or hormonal approaches, with the PCR assays described herein used to monitor eradication and risk reduction.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

Lengthy table referenced here

US11884984-20240130-T00001

Please refer to the end of the specification for access instructions.

Lengthy table referenced here
US11884984-20240130-T00002
Please refer to the end of the specification for access instructions.

Lengthy table referenced here
US11884984-20240130-T00003
Please refer to the end of the specification for access instructions.

Lengthy table referenced here
US11884984-20240130-T00004
Please refer to the end of the specification for access instructions.

Lengthy table referenced here
US11884984-20240130-T00005
Please refer to the end of the specification for access instructions.

Lengthy table referenced here
US11884984-20240130-T00006
Please refer to the end of the specification for access instructions.

Lengthy table referenced here
US11884984-20240130-T00007
Please refer to the end of the specification for access instructions.

Lengthy table referenced here
US11884984-20240130-T00008
Please refer to the end of the specification for access instructions.

Lengthy table referenced here
US11884984-20240130-T00009
Please refer to the end of the specification for access instructions.

Lengthy table referenced here
US11884984-20240130-T00010
Please refer to the end of the specification for access instructions.

Lengthy table referenced here
US11884984-20240130-T00011
Please refer to the end of the specification for access instructions.

Lengthy table referenced here
US11884984-20240130-T00012
Please refer to the end of the specification for access instructions.

Lengthy table referenced here
US11884984-20240130-T00013
Please refer to the end of the specification for access instructions.

Lengthy table referenced here
US11884984-20240130-T00014
Please refer to the end of the specification for access instructions.

Lengthy table referenced here
US11884984-20240130-T00015
Please refer to the end of the specification for access instructions.

Lengthy table referenced here
US11884984-20240130-T00016
Please refer to the end of the specification for access instructions.

Lengthy table referenced here
US11884984-20240130-T00017
Please refer to the end of the specification for access instructions.

Lengthy table referenced here
US11884984-20240130-T00018
Please refer to the end of the specification for access instructions.

Lengthy table referenced here
US11884984-20240130-T00019
Please refer to the end of the specification for access instructions.

Lengthy table referenced here

US11884984-20240130-T00020

Please refer to the end of the specification for access instructions.

Lengthy table referenced here

US11884984-20240130-T00021

Please refer to the end of the specification for access instructions.

Lengthy table referenced here

US11884984-20240130-T00022

Please refer to the end of the specification for access instructions.

Lengthy table referenced here

US11884984-20240130-T00023

Please refer to the end of the specification for access instructions.

Lengthy table referenced here

US11884984-20240130-T00024

Please refer to the end of the specification for access instructions.

Lengthy table referenced here

US11884984-20240130-T00025

Please refer to the end of the specification for access instructions.

Lengthy table referenced here

US11884984-20240130-T00026

Please refer to the end of the specification for access instructions.

Lengthy table referenced here

US11884984-20240130-T00027

Please refer to the end of the specification for access instructions.

Lengthy table referenced here

US11884984-20240130-T00028

Please refer to the end of the specification for access instructions.

Lengthy table referenced here

US11884984-20240130-T00029

Please refer to the end of the specification for access instructions.

Lengthy table referenced here

US11884984-20240130-T00030

Please refer to the end of the specification for access instructions.

Lengthy table referenced here

US11884984-20240130-T00031

Please refer to the end of the specification for access instructions.

Lengthy table referenced here

US11884984-20240130-T00032

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US11884984B2). An electronic copy of the table will also be available from the USPTO upon request and payment of the fee set forth in 37 CFR 1.19(b)(3).

The invention claimed is:

1. A method for
detecting and classifying a nongonococcal urethritis (NGU) infection in a male subject, the method comprising
detecting a pathogen in a urethral sample from the male subject, wherein the pathogen comprises *Haemophilus influenzae, Mycoplasma penetrans*, or both, wherein detecting the pathogen comprises carrying out a quantitative PCR on the urethral sample with a primer set that hybridizes to nucleotide sequences selected from a 16S rRNA gene of *Haemophilus influenzae* or *Mycoplasma penetrans* to generate *Haemophilus influenzae* and/or *Mycoplasma penetrans* specific amplicons, and
classifying the NGU infection based at least in part on detection of the pathogen higher than a baseline level of a reference from healthy individuals.

2. The method of claim 1, further comprising selecting a therapeutic agent to administer to the male subject based on the detection of the pathogen.

3. The method of claim 1, further comprising administering an effective amount of a therapeutic agent to the male subject.

4. The method of claim 3, wherein the therapeutic agent comprises metronidazole, ceftriaxone, doxycycline, azithromycin, ciprofloxacin, or levofloxacin.

5. The method of claim 1, wherein the urethral sample is a urine sample.

6. The method of claim 1, wherein the urethral sample is from a penile or urethral swab.

7. The method of claim 1, wherein detecting the pathogen in the urethral sample further comprises carrying out a polymerase chain reaction (PCR) on the urethral sample with a second primer set that hybridizes to nucleotide sequences of *Haemophilus influenzae* or *Mycoplasma penetrans* to generate *Haemophilus influenzae* and/or *Mycoplasma penetrans* specific amplicons.

8. The method of claim 1, wherein detecting the pathogen in the urethral sample comprises determining a concentration of the pathogen in the urethral sample.

9. The method of claim 8, wherein determining the concentration of the pathogen comprises determining the concentration based on the quantitative PCR on the urethral sample with the primer set that hybridizes to nucleotide sequences selected from a 16S rRNA gene of *Haemophilus influenzae* or *Mycoplasma penetrans* to generate *Haemophilus influenzae* and/or *Mycoplasma penetrans* specific amplicons.

10. The method of claim 1, wherein detecting the pathogen further comprises southern blotting, in situ hybridization, whole genome sequencing, or next-generation sequencing.

11. The method of claim 1, further comprising detecting and determining a concentration of *Lactobacillus iners, Atopobium vaginae, Veillonella atypica*, or a combination thereof, in the urethral sample.

12. The method of claim 11, wherein detecting and determining the concentration of *Lactobacillus iners, Atopobium vaginae, Veillonella atypica*, or a combination thereof, in the urethral sample comprises carrying out a quantitative PCR on the urethral sample with a primer set that hybridizes to nucleotide sequences of *Lactobacillus iners, Atopobium vaginae*, or *Veillonella atypica*, to generate *Lactobacillus iners, Atopobium vaginae*, and/or *Veillonella atypica* specific amplicons.

13. The method of claim 1, wherein detecting and classifying the NGU infection in the male subject further comprises detecting a known pathogen in the urethral sample, the known pathogen comprising *Chlamydia trachomatis; Mycoplasma genitalium; Trichomonas vaginalis*; Adenovirus; Herpes simplex virus (HSV)-1; HSV-2; or a combination thereof.

14. The method of claim 13, wherein detecting the known pathogen in the urethral sample comprises carrying out a PCR on the urethral sample with a primer set that hybridizes to nucleotide sequences in the known pathogen to generate a known pathogen specific amplicon.

15. The method of claim 13, wherein classifying the NGU infection in the male subject further comprises determining a concentration of the known pathogen.

16. The method of claim 13, wherein determining the concentration of the known pathogen in the urethral sample comprises carrying out a quantitative PCR on the urethral sample with a primer set that hybridizes to nucleotide sequences in the known pathogen to generate a known pathogen specific amplicon.

* * * * *

SEQUENCE LISTING

<160> NUMBER OF SEQ ID NOS: 103

<210> SEQ ID NO 1
<211> LENGTH: 20
<212> TYPE: DNA
<213> ORGANISM: Mycoplasma penetrans

<400> SEQUENCE: 1
cggacgaagc acttgtgctt                                                    20

<210> SEQ ID NO 2
<211> LENGTH: 24
<212> TYPE: DNA
<213> ORGANISM: Mycoplasma penetrans

<400> SEQUENCE: 2
ttttctcatg cgatagtaat gtcc                                               24

<210> SEQ ID NO 3
<211> LENGTH: 32
<212> TYPE: DNA
<213> ORGANISM: Artificial sequence
<220> FEATURE:
<223> OTHER INFORMATION: Probe

<400> SEQUENCE: 3
taacatacct tttagtgggg gataactggt tg                                      32

<210> SEQ ID NO 4
<211> LENGTH: 24
<212> TYPE: DNA
<213> ORGANISM: Haemophilus influenzae

<400> SEQUENCE: 4
gcccgtagct aacgtgataa atcg                                               24

<210> SEQ ID NO 5
<211> LENGTH: 26
<212> TYPE: DNA
<213> ORGANISM: Haemophilus influenzae

<400> SEQUENCE: 5
aagctcatct ctgagctctt cttagg                                             26

<210> SEQ ID NO 6
<211> LENGTH: 26
<212> TYPE: DNA
<213> ORGANISM: Artificial sequence
<220> FEATURE:
<223> OTHER INFORMATION: Probe

<400> SEQUENCE: 6
caagcggtgg agcatgtggt ttaatt                                             26

<210> SEQ ID NO 7
<211> LENGTH: 53
<212> TYPE: DNA
<213> ORGANISM: Artificial sequence
<220> FEATURE:
<223> OTHER INFORMATION: Probe

<400> SEQUENCE: 7
tcgtcggcag cgtcagatgt gtataagaga cagaytcctr cgggargcag cag               53

```
<210> SEQ ID NO 8
<211> LENGTH: 51
<212> TYPE: DNA
<213> ORGANISM: Artificial sequence
<220> FEATURE:
<223> OTHER INFORMATION: Probe

<400> SEQUENCE: 8
tcgtcggcag cgtcagatgt gtataagaga cagactccta cgggaggctg c        51

<210> SEQ ID NO 9
<211> LENGTH: 51
<212> TYPE: DNA
<213> ORGANISM: Artificial sequence
<220> FEATURE:
<223> OTHER INFORMATION: Probe

<400> SEQUENCE: 9
tcgtcggcag cgtcagatgt gtataagaga cagacaccta cgggtggcag c         51

<210> SEQ ID NO 10
<211> LENGTH: 54
<212> TYPE: DNA
<213> ORGANISM: Artificial sequence
<220> FEATURE:
<223> OTHER INFORMATION: Probe

<400> SEQUENCE: 10
gtctcgtggg ctcggagatg tgtataagag acagggacta chvgggtatc taat       54

<210> SEQ ID NO 11
<211> LENGTH: 23
<212> TYPE: DNA
<213> ORGANISM: Ureaplasma urealyticum

<400> SEQUENCE: 11
caatttacat catcgacgtt gcc                                         23

<210> SEQ ID NO 12
<211> LENGTH: 26
<212> TYPE: DNA
<213> ORGANISM: Ureaplasma urealyticum

<400> SEQUENCE: 12
gagctaaatc aactttattg atgatg                                      26

<210> SEQ ID NO 13
<211> LENGTH: 18
<212> TYPE: DNA
<213> ORGANISM: Artificial sequence
<220> FEATURE:
<223> OTHER INFORMATION: Probe

<400> SEQUENCE: 13
ctcgtaaagg cggacaag                                               18

<210> SEQ ID NO 14
<211> LENGTH: 22
<212> TYPE: DNA
<213> ORGANISM: Trichomonas vaginalis

<400> SEQUENCE: 14
cattgaccac acggacaaaa ag                                          22

<210> SEQ ID NO 15
```

```
<211> LENGTH: 18
<212> TYPE: DNA
<213> ORGANISM: Trichomonas vaginalis

<400> SEQUENCE: 15
cgaagtgctc gaatgcga                                                    18

<210> SEQ ID NO 16
<211> LENGTH: 23
<212> TYPE: DNA
<213> ORGANISM: Artificial sequence
<220> FEATURE:
<223> OTHER INFORMATION: Probe

<400> SEQUENCE: 16
catttcggat ggtcaagcag cca                                              23

<210> SEQ ID NO 17
<211> LENGTH: 22
<212> TYPE: DNA
<213> ORGANISM: BVAB-2

<400> SEQUENCE: 17
ttaaccttgg ggttcattac aa                                               22

<210> SEQ ID NO 18
<211> LENGTH: 24
<212> TYPE: DNA
<213> ORGANISM: BVAB-2

<400> SEQUENCE: 18
gaatacttat tgtgttaact gcgc                                             24

<210> SEQ ID NO 19
<211> LENGTH: 23
<212> TYPE: DNA
<213> ORGANISM: Artificial sequence
<220> FEATURE:
<223> OTHER INFORMATION: Probe

<400> SEQUENCE: 19
tctccagcac tcaagctaaa cag                                              23

<210> SEQ ID NO 20
<211> LENGTH: 1009
<212> TYPE: DNA
<213> ORGANISM: BVAB-2

<400> SEQUENCE: 20
tggggaatat tgggcaatgg gcgaaagcct gacccagcaa cgccgcgtga gtgatgatgg      60
ccttcgggtt gtaaaactct tggacaggg acgaagaaag tgacggtacc tgtagaacaa     120
gccacggcta actacgtgcc agcagccgcg gtaatacgta ggtggcgagc gttatccgga    180
tttactgggc gtaaagggcg tgtaggcggc tagataagtg tgatgtttaa atccaaggct    240
taaccttggg gttcattaca aactgtttag cttgagtgct ggagaggata gtggaattcc    300
tagtgtagcg gtaaaatgcg tagatattag gaggaacacc ggtggcgaag gcggctatct    360
ggacagtaac tgacgctgag gcgcgaaagc gtggggagca acaggatta gataccctgg    420 tagtccacgc cgtaaacgat gaatactagc tgtaggaggt atcgacccct tctgtggcgc    480
agttaacaca ataagtattc cgcctgggga gtacggccgc aaggttaaaa ctcaaaggaa    540
ttgacgggga cccgcacaag cagtggatta tgtggtttaa ttcgaagcaa cgcgaagaac    600
```

```
cttaccagga cttgacatcc tctgacgatt caggagactg aattttctct tcggagacag    660
agagacaggt ggtgcatggt tgtcgtcagc tcgtgtcgtg agatgttggg ttaagtcccg    720
caacgagcgc aacccctatt gattgttgct aacagtaaga tgagcactca attgagactg    780
ccgttgataa aacggaggaa ggtggggacg acgtcaaatc atcatgcccc ttatgttctg    840
ggctacacac gtaatacaat ggctgtgaca gagggaagca agagggcgac cttaagcgaa    900
tcccaaaacg cagtctcagt tcggattgca ggctgcaact cgcctgcatg aagtcggaat    960
tgctagtaat ggcaggtcag catactgccg tgaatacgtt cccgggtct               1009
```

<210> SEQ ID NO 21
<211> LENGTH: 21
<212> TYPE: DNA
<213> ORGANISM: Eggerthella-like species type 1

<400> SEQUENCE: 21

```
gaccaacctg cctcttacat t                                              21
```

<210> SEQ ID NO 22
<211> LENGTH: 22
<212> TYPE: DNA
<213> ORGANISM: Eggerthella-like species type 1

<400> SEQUENCE: 22

```
gcatacatca tgtgatatgt gc                                             22
```

<210> SEQ ID NO 23
<211> LENGTH: 24
<212> TYPE: DNA
<213> ORGANISM: Artificial sequence
<220> FEATURE:
<223> OTHER INFORMATION: Probe

<400> SEQUENCE: 23

```
aaaagaaatt ctggctaata ccaa                                           24
```

<210> SEQ ID NO 24
<211> LENGTH: 1372
<212> TYPE: DNA
<213> ORGANISM: Eggerthella-like species type 1

<400> SEQUENCE: 24

```
attaaagcac cttcgggtgt gtatagagtg gcgaacgggt gagtaacacg tgaccaacct    60
gcctcttaca ttgggacaac caaagaaatt ctggctaat accaaatact ccgcacatat    120
cacatgatgt atgcgggaaa gcttttgcgg taagagatgg ggtcgcggcc cattaggtag    180
acggcggggt agaagcccac cgtgccgatg atgggtagcc gggttgagag accgaccggc    240
cacattggga ctgagatacg gcccagactc ctacgggagg cagcagtggg gaatattgcg    300
caatggggga aaccctgacg cagcaacgcc gcgtgcggga tgaaggcctt cgggttgtaa    360
accgctttca gcagggaaga catcgacggt acctgcagaa gaagcccgg ctaactacgt    420 gccagcagcc gcggtaatac gtaggggcg agcgttatcc ggattcattg ggcgtaaagc    480
gcgcgcaggc ggttgctcaa gcggaacctc taatctcggg gcttaacctc gagccgggtt    540
ccgaactgga cgactcgagt gcggtagagg cagatggaat tcccggtgta gcggtggaat    600
gcgcagatat cggaagaac accaacgcg aaggcagtct gctgggccgt cactgacgct    660
gaggcgcgaa agctggggga gcgaacagga ttagataccc tggtagtccc agccgtaaac    720
```

```
gatgagcgct gggtgtggga gattacatct tccgtgccga agctaacgca ttaagcgctc    780
cgcctgggga gtacggccgc aaggctaaaa ctcaaaggaa ttgacggggg cccgcacaag    840
cagcggagca tgtggcttaa ttcgaagcaa cgcgaagaac cttaccaggg cttgacatgt    900
aggtgaagcg gcggaaacgt cgtggccgaa aggagcctac acaggtggtg catggctgtc    960
gtcagctcgt gtcgtgagat gttgggttaa gtcccgcaac gagcgcaacc cctgccccgt   1020
gttaccagca tttagttggg gactcgcggg ggactgccgg cgtcaagccg aggaaggcg    1080 gggatgacgt caagtcatca tgccccttat gccctgggcc gcacacgtgc tacaatggcc   1140
ggcacagcgg gctgcaacct agcgatagga agcgaatccc gtaaagccgg tcccagttcg   1200
gattggaggc tgaaacccgc ctccatgaag ccggagttgc tagtaatcgc ggatcagcac   1260
gccgcggtga atgcgttccc gggccttgta cacaccgccc gtcacaccac ccgagtcgtc   1320
tgcacccgaa gccgccggcc gaaccccttt ggggacggag gcgtcgaagg tg           1372
```

<210> SEQ ID NO 25
<211> LENGTH: 25
<212> TYPE: DNA
<213> ORGANISM: Gemella assacharolytica

<400> SEQUENCE: 25

```
ttaccaagtc ttgacataca gtgaa                                            25
```

<210> SEQ ID NO 26
<211> LENGTH: 23
<212> TYPE: DNA
<213> ORGANISM: Gemella assacharolytica

<400> SEQUENCE: 26

```
accacctgta tcagtgttta atg                                              23
```

<210> SEQ ID NO 27
<211> LENGTH: 25
<212> TYPE: DNA
<213> ORGANISM: Artificial sequence
<220> FEATURE:
<223> OTHER INFORMATION: Probe

<400> SEQUENCE: 27

```
ataagaaatt atattgtttt aatgt                                            25
```

<210> SEQ ID NO 28
<211> LENGTH: 1402
<212> TYPE: DNA
<213> ORGANISM: Gemella assacharolytica

<400> SEQUENCE: 28

```
cgaactttaa gagtgcttgc acacttaaag ttagcggcga acgggtgagt aacacgtaaa     60
gaacctacct tatagacagg gacaactatt ggaaacgata gctaatacct gataagaaag    120
aaactcgcat gagagaagtt cgaaagtcgg agcaatctga cactataaga tggctttgcg    180
gtgcattagc tagttggtag ggtaaaagcc taccaaggcg acgatgcata gccgacctga    240
gagggtgatc ggccacattg ggactgagac acggcccaga ctcctacggg aggcagcagt    300
agggaatctt ccgcaatgga cgcaagtctg acggagcaac gccgcgtgag tgaagaagga    360
tttcggttcg taaaactctg ttgttaggga agaaaaaatg tataataact atatacaaaa    420
gagacggtac ctaaccagaa agccacggct aactacgtgc cagcagccgc ggtaatacgt    480
aggtggcaag cgttgtccgg aattattggg cgtaaagcgc gcgcaggtgg tttagaaagt    540
```

-continued

```
ctgatgtgaa agcccacggc tcaaccgtgg agggtcattg gaaactaata aacttgagtg      600
caggagagaa aagtggaatt cctagtgtag cggtgaaatg cgtagagatt aggaggaaca      660
ccggtggcga aagcggcttt ttggcctgca actgacactg aggcgcgaaa gcgtggggag      720
caaacaggat tagataccct ggtagtccac gccgtaaacg atgagtgcta agtgttggag      780
tcaaaagact tcagtgctgc agcaaacgc attaagcact ccgcctgggg agtacgatcg      840
caagattgaa actcaaagga attgacgggg acccgcacaa gcggtggagt atgtggttta      900
attcgaagca acgcgaagaa ccttaccaag tcttgacata cagtgaagat ataagaaatt      960
atattgtttt aatgtttaca ttaaacactg atacaggtgg tgcatggttg tcgtcagctc     1020
gtgtcgtgag atgttgggtt aagtcccgca acgagcgcaa cccttatatc tagttaccag     1080
cagtaagatg gggactctag atagactgcc agtgacaaac tggaggaagg tggggatgac     1140
gtcaaatcat catgcccctt atgacttggg ctacacacgt actacaatgg ataggacaaa     1200
gagaagcgac ctcgcaagag caagccaacc tcagaaaact attctcagtt cggattgtag     1260
gctgcaactc gcctacatga agctggaatc gctagtaatc gcgaatcaga atgtcgcggt     1320
gaatacgttc ccgggtcttg tacacaccgc ccgtcacacc acgagagttt gtaacacctg     1380
aagacggtgg cctaaccgta ag                                              1402
```

<210> SEQ ID NO 29
<211> LENGTH: 23
<212> TYPE: DNA
<213> ORGANISM: Lactobacillus crispatus

<400> SEQUENCE: 29

```
tcttgacatc tagtgccatt tgt                                                23
```

<210> SEQ ID NO 30
<211> LENGTH: 18
<212> TYPE: DNA
<213> ORGANISM: Lactobacillus crispatus

<400> SEQUENCE: 30

```
tgcaccacct gtcttagc                                                      18
```

<210> SEQ ID NO 31
<211> LENGTH: 24
<212> TYPE: DNA
<213> ORGANISM: Artificial sequence
<220> FEATURE:
<223> OTHER INFORMATION: Probe

<400> SEQUENCE: 31

```
ccgaagggaa ctttgtatct ctac                                               24
```

<210> SEQ ID NO 32
<211> LENGTH: 1033
<212> TYPE: DNA
<213> ORGANISM: Lactobacillus crispatus

<400> SEQUENCE: 32

```
tagggaatct tccacaatgg acgcaagtct gatggagcaa cgccgcgtga gtgaagaagg       60
ttttcggatc gtaaagctct gttgttggtg aagaaggata gaggtagtaa ctggccttta      120
tttgacggta atcaaccaga aagtcacggc taactacgtg ccagcagccg cggtaatacg      180
taggtggcaa gcgttgtccg gatttattgg gcgtaaagcg agcgcaggcg gaagaataag      240
```

| | |
|---|---|
| tctgatgtga aagccctcgg cttaaccgag gaactgcatc ggaaactgtt tttcttgagt | 300 |
| gcagaagagg agagtggaac tccatgtgta gcggtggaat gcgtagatat atggaagaac | 360 |
| accagtggcg aaggcggctc tctggtctgc aactgacgct gaggctcgaa agcatgggta | 420 |
| gcgaacagga ttagataccc tggtagtcca tgccgtaaac gatgagtgct aagtgttggg | 480 |
| aggtttccgc ctctcagtgc tgcagctaac gcattaagca ctccgcctgg ggagtacgac | 540 |
| cgcaaggttg aaactcaaag gaattgacgg gggcccgcac aagcggtgga gcatgtggtt | 600 |
| taattcgaag caacgcgaag aaccttacca ggtcttgaca tctagtgcca tttgtagaga | 660 |
| tacaaagttc ccttcgggga cgctaagaca ggtggtgcat ggctgtcgtc agctcgtgtc | 720 |
| gtgagatgtt gggttaagtc cgcaacgagc gcaacccctt gttattagtt gccagcatta | 780 |
| agttgggcac tctaatgaga ctgccggtga caaaccggag gaaggtgggg atgacgtcaa | 840 |
| gtcatcatgc cccttatgac ctgggctaca cacgtgctac aatgggcagt acaacgagaa | 900 |
| gcgagcctgc gaaggcaagc gaatctctga aagctgttct cagttcggac tgcagtctgc | 960 |
| aactcgactg cacgaagctg gaatcgctag taatcgcgga tcagcacgcc gcggtgaata | 1020 |
| cgttcccggg cct | 1033 |

```
<210> SEQ ID NO 33
<211> LENGTH: 23
<212> TYPE: DNA
<213> ORGANISM: Sneathia amnii

<400> SEQUENCE: 33
```

| | |
|---|---|
| aattattggg cttaaagggc atc | 23 |

```
<210> SEQ ID NO 34
<211> LENGTH: 25
<212> TYPE: DNA
<213> ORGANISM: Sneathia amnii

<400> SEQUENCE: 34
```

| | |
|---|---|
| gtactctagt tcaacagttt tgtag | 25 |

```
<210> SEQ ID NO 35
<211> LENGTH: 26
<212> TYPE: DNA
<213> ORGANISM: Sneathia sanguinegens

<400> SEQUENCE: 35
```

| | |
|---|---|
| agtactctag ttatacagtt ttgtag | 26 |

```
<210> SEQ ID NO 36
<211> LENGTH: 26
<212> TYPE: DNA
<213> ORGANISM: Artificial sequence
<220> FEATURE:
<223> OTHER INFORMATION: Probe

<400> SEQUENCE: 36
```

| | |
|---|---|
| acaagttgaa ggtgaaaacc trtggc | 26 |

```
<210> SEQ ID NO 37
<211> LENGTH: 1009
<212> TYPE: DNA
<213> ORGANISM: Sneathia amnii

<400> SEQUENCE: 37
```

| | |
|---|---|
| tggggaatat tggacaatgg agggaactct gatccagcaa ttctgtgtgt gtgaagaagg | 60 |

```
ttttaggact gtaaaacact tttagtaggg aagaaaaaaa tgacggtacc tacagaagaa      120
gcaacggcta aatacgtgcc agcagccgcg gtaatacgta tgttgcgagc gttatccgga      180
attattgggc ttaaagggca tctaggcggt aagacaagtt gaaggtgaaa acctgtggct      240
caaccatagg cttgcctaca aaactgttga actagagtac tggaaaggtg ggtggaacta      300
cacgagtaga ggtgaaattc gtagatatgt gtaggaatgc cgatgatgaa gataactcac      360
tggacagaaa ctgacgctga agtgcgaaag ctaggggagc aaacaggatt agataccctg      420
gtagtcctag ctgtaaacga tgatcactgg gtgtggggat gcgaagtctc tgtgccgaag      480
caaaagcgat aagtgatccg cctggggagt acgttcgcaa gaatgaaact caaaggaatt      540
gacgggggcc cgcacaagtg gtggagcatg tggtttaatt cgacgcaacg cgaggaacct      600
taccagatct tgacatcctc gggagagtat agaagtatac ttgtgccttc gggaaccgag      660
agacaggtgg tgcatggctg tcgacagctc gtgttgtgag atgttgggtt aagtcccgca      720
acgagcgaaa ccctatcat tagttgccat cattaagttg gggactctaa tgaaactgcc       780
tacgaagagt aggaggaagg tggggatgac gtcaagtcat catgcccctt atgatctggg      840
ctacacacgt gctacaatgg gtagtacaaa gagaagcttt gtagcgatac atggcgaaac      900
ttaaaaagct attcttagtt cggattgaag tctgcaactc gacttcatga agttggaatc      960
actagtaatc gtgaatcagc aatgtcacgg tgaatacgtt ctcgggcct                 1009

<210> SEQ ID NO 38
<211> LENGTH: 1008
<212> TYPE: DNA
<213> ORGANISM: Sneathia sanguinegens

<400> SEQUENCE: 38
tggggaatat tggacaatgg aggcaactct gatccagcaa ttctgtgtgt gtgaagaagg       60
ttttaggact gtaaacactt ttagtaggga agaaagaaat gacggtacct acagaagaag      120
cgacggctaa atacgtgcca gcagccgcgg taatacgtat gtcgcgagcg ttatccggaa      180
ttattgggct taaagggcat ctaggcggtt aaacaagttg aaggtgaaaa cctgtggctc      240
aaccataggc ttgcctacaa aactgtataa ctagagtact ggaaaggtgg gtggaactac      300
acgagtagag gtgaaattcg tagatatgtg taggaatgcc gatgatgaag ataactcact      360
ggacagcaac tgacgctgaa gtgcgaaagc taggggagca aacaggatta gataccctgg      420
tagtcctagc tgtaaacgat gatcactggg tgtgggggatt cgaagtctct gtgccgaagc      480
aaaagcgata agtgatccgc tggggagta cgttcgcaag aatgaaactc aaaggaattg       540
acggggaccc gcacaagtgg tggagcatgt ggtttaattc gacgcaacgc gaggaacctt      600
accagatctt gacatcctcc gaagagcata gaagtatgct tgtgcctacg gaacggaga       660 gacaggtggt gcatggctgt cgacagctcg tgttgtgaga tgttgggtta agtcccgcaa      720
cgagcgaaac ccctatcatt agttaccatc attaagttgg ggactctaat gaaactgcct      780
acgaagagta ggaggaaggt ggggatgacg tcaagtcatc atgcccctta tgatctgggc      840
tacacacgtg ctacaatgga tagtacaaag agaagctttg tagcgataca tggcaaaact      900
aagaaagcta ttcttagttc ggattgaagt ctgcaactcg acttcatgaa gttggaatca      960
ctagtaatcg tgaatcagca atgtcacggt gaatacgttc tcgggtct                  1008

<210> SEQ ID NO 39
<211> LENGTH: 26
<212> TYPE: DNA
```

```
<213> ORGANISM: Mycoplasma hominis

<400> SEQUENCE: 39
tgttataagg gaagaacatt tgcaat                                          26

<210> SEQ ID NO 40
<211> LENGTH: 22
<212> TYPE: DNA
<213> ORGANISM: Mycoplasma hominis

<400> SEQUENCE: 40
gttagccatc gctttctgac aa                                              22

<210> SEQ ID NO 41
<211> LENGTH: 18
<212> TYPE: DNA
<213> ORGANISM: Artificial sequence
<220> FEATURE:
<223> OTHER INFORMATION: Probe

<400> SEQUENCE: 41
aaatgattgc agactgac                                                   18

<210> SEQ ID NO 42
<211> LENGTH: 722
<212> TYPE: DNA
<213> ORGANISM: Mycoplasma hominis
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t

<400> SEQUENCE: 42
tgcatgtcga gcgaggttag cantaaccta gcggcgaatg ggtgagtaac acgtgcttaa     60
tctacctttt agattgaata cccattggaa acaatggcta atgccggata cgcatggaac   120
cgcatggttc cgttgtgaaa ggcgctgtaa ggcgccacta aaagatgagg gtgcggaaca   180
ttagttagtt ggtgaggtaa tggcccacca agactatgat gtttagccgg gtcgagagac   240
tgaacggcca cattgggact gagatacggc ccaaactcct acgggaggca gcagtaggga   300
atattccaca atgagcgaaa gcttgatgga gcgacacagc gtgcacgatg aaggtcttcg   360
gattgtaaag tgctgttata agggaagaac atttgcaata ggaaatgatt gcagactgac   420
ggtaccttgt cagaaagcga tggctaacta tgtgccagca gccgcggtaa tacataggtc   480
gcaagcgtta tccggaatta tttgggcgtaa agcgttcgta ggctgtttgt taagtctgga   540
gttaaatccc ggggctcaac cccggctcgc tttggatact agcaaactag agttagatag   600
aggtaagcgg aattccatgt gaagcggtga aatgcgtaga tatatggaag aacaccaaag   660
gcgaangcag cttactgggt ctatactgac gctganggac gaaagcgtgg ggagcaaaca   720
gg                                                                  722

<210> SEQ ID NO 43
<211> LENGTH: 23
<212> TYPE: DNA
<213> ORGANISM: Porphyromonas species Type 1
```

```
<400> SEQUENCE: 43
atagcaatat cttgtgtcgg cga                                              23

<210> SEQ ID NO 44
<211> LENGTH: 18
<212> TYPE: DNA
<213> ORGANISM: Porphyromonas species Type 1

<400> SEQUENCE: 44
gcgccgcatg cccatcct                                                    18

<210> SEQ ID NO 45
<211> LENGTH: 29
<212> TYPE: DNA
<213> ORGANISM: Artificial sequence
<220> FEATURE:
<223> OTHER INFORMATION: Probe

<400> SEQUENCE: 45
tcccatagtc cctgagtttg catgagctt                                        29

<210> SEQ ID NO 46
<211> LENGTH: 1120
<212> TYPE: DNA
<213> ORGANISM: Porphyromonas species Type 1
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (1102)..(1102)
<223> OTHER INFORMATION: n is a, c, g, or t

<400> SEQUENCE: 46
ggggaaagtt ccggcggtag aggatgggca tgcggcgcat tanctggttg gcggggtaac      60
ggcccaccaa ggcgacgatg cgtaggggtt ctgagaggaa ggtcccccac actggtactg     120
agacacggac cagactccta cgggaggcag cagtgaggaa tattggtcaa tgggcgcgag     180
cctgaaccag ccaagtcgcg tgagganga cggtcctacg gattgtaaac ctctttaggc     240
ggggagtaat gtgctctacg agtagagtag tgagagtacc cgcagaataa gcatcggcta     300
actccgtgcc agcagccgcg gtaatacgga ggatgcgagc gttatccgga tttattgggt     360
ttaaagggtg cgcaggctgt gcatcaagtc agcggtaaaa tctcggggct caaccccgtt     420
tagccgttga aactggtgtg ctggagtgtg cgcgaggaag gcggaatgcg cggtgtagcg     480
gtgaaatgca tagatattgc gcagaactcc gattgcgaag gcagccttcc agtgcatgac     540
tgacgctgag gcacgaaagc gtgggtatcg aacaggatta gataccctgg tagtccacgc     600
agtaaacgat gaatactatc tttccgtcgc gnctgagcgg ggggaggaca agcgaaagcg     660
ttaagtattc cacctgggga gtacgccggc aacggtgaaa ctcaaaggaa ttgacggggg     720
cccgcacaag cggaggaaca tgtggtttaa ttcgatgata cgcgaggaac cttacccggg     780
ctcaaacgct gatagatcgg tgtggaaaca cgccttccct tcgggctgt cagcgaggtg     840
```

```
ctgcatggtt gtcgtcagct cgtgccgtga ggtgtcggct taagtgccat aacgagcgca    900
accccatct ccagttgcca tcggttaaag ccgggcactc tggagagact gccggcgcaa     960
gccgtgagga gggcggggat gacgtcaaat cagcacggcc cttacgtccg gggcgacaca   1020
cgtgttacaa tggcggagtt acagcgggaa gccaggcggc gacgtcgagc tgatcccgaa   1080
aatccgtctc agttcggatc gnagtctgca acccgactcc                         1120
```

<210> SEQ ID NO 47
<211> LENGTH: 24
<212> TYPE: DNA
<213> ORGANISM: Porphyromonas uenonis

<400> SEQUENCE: 47

```
aacttacctc ttagtggtga ataa                                            24
```

<210> SEQ ID NO 48
<211> LENGTH: 25
<212> TYPE: DNA
<213> ORGANISM: Porphyromonas uenonis

<400> SEQUENCE: 48

```
tatctcttag cgattaatct ttcct                                           25
```

<210> SEQ ID NO 49
<211> LENGTH: 25
<212> TYPE: DNA
<213> ORGANISM: Artificial sequence
<220> FEATURE:
<223> OTHER INFORMATION: Probe

<400> SEQUENCE: 49

```
accatactct ccttagatca catga                                           25
```

<210> SEQ ID NO 50
<211> LENGTH: 923
<212> TYPE: DNA
<213> ORGANISM: Porphyromonas uenonis
<220> FEATURE:
<221> NAME/KEY: misc_feature
<222> LOCATION: (526)..(526)
<223> OTHER INFORMATION: n is a, c, g, or t

<400> SEQUENCE: 50

```
gtcgagggc agcgagatgt agcaatacgt cgtcggcgac cggcgaatgg gtgagtaaca     60
cgtatgcaac ttacctctta gtggtgaata actcgatgaa agtcggacta atacaccata   120
ctctccttag atcacatgag aagaggagga aagattaatc gctaagagat aggcctgcgt   180
tccattagct agttggtaag gtaacggctt accaaggcaa cgatggatag ggggactgag   240
aggttgaccc cccacattga cactgagata cgggtcaaac tcctacggga ggcagcagtg   300
aggagtattg gtcaatgggc gagagcctga accagccaag tcgcgtgaag gaagactgcc   360
cgcaagggtt gtaaacttct tttgtatggg attaaagtcg tctacgtgta gacgtttgca   420
gttaccatac gaataagcat cggctaactc cgtgccagca gccgcggtaa tacggaggat   480
gcgagcgtta tccggaatta ttgggtttaa agggtgcgta ggttgnaagg gaagtcaggg   540
gtgaaaagct atagctcaac tatggtcttg cctttgaaac tctctagcta gagtgtactg   600
gaggtacgtg gaacgtgtgg tgtagcggtg aaatgcatag atatcacaca gaactccgat   660
tgcgcaggca gcgtactaca ttacaactga cactgaagca cgaaagcgtg ggtatccaac   720
aggattagat accctggtag tccacgcagt aaacgatgaa tactagatct atgcgataca   780
```

```
ctgtatgggt ctaagcgaaa gcgataagta ttccacctgg ggagtacgcc ggcaacggtg    840
aaactcaaag agattggcgg gggtccgcac aagcggagga acatgtggtt taattcgatg    900
atacgcgagg aaccttaccc ggg                                            923
```

<210> SEQ ID NO 51
<211> LENGTH: 1423
<212> TYPE: DNA
<213> ORGANISM: Porphyromonas asaccharolytica

<400> SEQUENCE: 51

```
ggcttaacac atgcaagtcg aggggcagcg agatgtagca atacgtcgtc ggcgaccggc     60
gaatgggtga gtaacacgta tgcaacttac ctcttagtgg tgaataaccc gatgaaagtc    120
ggactaatac accatactct ccttagatca catgagaaga ggaggaaaga ttaatcgcta    180
agagataggc ctgcgttcca ttagctagtt ggtaaggtaa cggcttacca aggcaacgat    240 ggatagggggg actgagaggt tgaccccccca cattgacact gagatacggg tcaaactcct   300
acgggaggca gcagtgagga atattggtca atgggcgaga gcctgaacca gccaagtcgc    360
gtgaaggaag actgcccgca agggttgtaa acttcttttg tatgggatta aagtcaccta    420
cgtgtaggtg tttgcagtta ccatacgaat aagcatcggc taactccgtg ccagcagccg    480
cggtaatacg gaggatgcga gcgttatccg gaattattgg gtttaaaggg tgcgtaggtt    540
gcaagggaag tcagggtga aaagctgtag ctcaactatg gtcttgcctt tgaaactctc    600
tagctagagt gtactggagg tacgtggaac gtgtggtgta gcggtgaaat gcatagatat    660
cacacagaac tccgattgcg caggcagcgt actacattac aactgacact gaagcacgaa    720
agcgtgggta tcaaacagga ttagataccc tggtagtcca cgcagtaaac gatgaatact    780
agatctatgc gatatacagt atgggtctaa gcgaaagcga taagtattcc acctggggag    840
tacgccggca acggtgaaac tcaaagagat tggcgggggt ccgcacaagc ggaggaacat    900
gtggtttaat tcgatgatac gcgaggaacc ttacccggga ttgaaatgta gatgcatgag    960
gctgagaggt ctcttccctt cggggcttct atgtaggtgc tgcatggttg tcgtcagctc   1020
gtgccgtgag gtgtcggctt aagtgccata acgagcgcaa cccgcgtcga tagttactaa   1080
cgagtcaagt cgaggactct atcgagacag ccgtcgtaag acgtgaggaa ggagcggatg   1140
acgtcaaatc agcacggccc ttacatccgg ggcgacacac gtgttacaat ggtagggaca   1200
gcgagcagcc atctggcgac agagagctaa tctataaacc ctatcccagt tcggatcgga   1260
gtctgcaact cgactctgtg aagctggatt cgctagtaat cgcgcatcag ccatggcgcg   1320
gtgaatacgt tcccggacct tgcacacacc gcccgtcaag ccatgggagt cgggggtacc   1380
tgaagagcgt gaccgtcaca ggagcgcttg agggtaaaac tgg                    1423
```

<210> SEQ ID NO 52
<211> LENGTH: 24
<212> TYPE: DNA
<213> ORGANISM: Parvimonas species Type 2

<400> SEQUENCE: 52

```
aacgagagtt agatcgaatg agtt                                            24
```

<210> SEQ ID NO 53
<211> LENGTH: 23
<212> TYPE: DNA
<213> ORGANISM: Parvimonas species Type 2

<400> SEQUENCE: 53
ggtattaatc accgtttcca atg                                             23

<210> SEQ ID NO 54
<211> LENGTH: 29
<212> TYPE: DNA
<213> ORGANISM: Artificial sequence
<220> FEATURE:
<223> OTHER INFORMATION: Probe

<400> SEQUENCE: 54
acaagtgaga tttaacgaaa gtggcgaac                                       29

<210> SEQ ID NO 55
<211> LENGTH: 1412
<212> TYPE: DNA
<213> ORGANISM: Parvimonas species Type 2

<400> SEQUENCE: 55
gcgtgcttaa cacatgcaag tcgaacgaga gttagatcga atgagttttc ggacaagtga      60
gatttaacga aagtggcgaa cgggtgagta acacgtgagc aacctgcctt acacaggggg     120
atagccattg gaaacggtga ttaataccccc ataagaccac aataccgcat ggtaaaaggg    180
taaaagggat accggtgtaa gatgggctcg cgtctgatta gctagttggt ggggtaaagg     240
cctaccaagg cgacgatcag tagccggtct gagaggatga acggccacat tggaactgag    300
acacggtcca aactcctacg ggaggcagca gtggggaata ttgcacaatg ggggaaaccc    360
tgatgcagcg acgccgcgtg agcgaagaag gctttcgagt cgtaaagctc tgtcctatga    420
gaagataatg acggtatcat aggaggaagc cctggctaaa tacgtgccag cagccgcggt    480
aatacgtatg gggcgagcgt tgtccggaat tattgggcgt aaagggtacg taggcggttt    540
tttaagtcag gtgtcaaagc gtggagctta actccattaa gcacttgaaa ctgaaagact    600
tgagtgaagg agaggaaagt ggaattccta gtgtagcggt gaaatgcgta gatattagga    660
ggaataccgg tggcgaaggc gactttctgg acttttactg acgctcaggt acgaaagcgt    720
ggggagcaaa caggattaga taccctggta gtccacgccg taaacgatga atgctaggtg    780
ttgggagtca aatctcggtg ccgaagttaa cacattaagc attccgcctg ggagtacgg    840 tgcaacacact gaaactcaaa ggaattgacg ggacccgca caagcagcgg agcatgtggt    900
ttaattcgaa gcaacgcgaa gaaccttacc aaggcttgac ataagttgag ttattgagaa    960
attgataagt ccctcgggac aactatacag gtggtgcatg gttgtcgtca gctcgtgtcg   1020
tgagatgttg ggttaagtcc cgcaacgagc gcaacccta ttttcagtta ccagcattta   1080
aggtggggac tctgaagaga ctgccgatga caaatcggag gaaggtgggg atgacgtcaa   1140
atcatcatgc cctttatgtc ttgggctaca cacgtgctac aatggtcggt acaacgagaa   1200
gcgagatagt gatgttaagc gaaactctaa aagccgatct cagttcggat tgtaggctgc   1260
aactcgccta catgaagtcg gagttgctag taatcgcgaa tcagaacgtc gcggtgaatg   1320
cgttcccggg tcttgtacac accgcccgtc acaccatggg agcttgtaat acccgaagcc   1380
gtcgatccaa ccgcaaggag gaagacgtcg aa                                 1412

<210> SEQ ID NO 56
<211> LENGTH: 21
<212> TYPE: DNA
<213> ORGANISM: Bulleidia species Type 1

<400> SEQUENCE: 56

| | |
|---|---|
| catggttaaa ttttggggct c | 21 |

<210> SEQ ID NO 57
<211> LENGTH: 21
<212> TYPE: DNA
<213> ORGANISM: Bulleidia species Type 1

<400> SEQUENCE: 57

| | |
|---|---|
| aattccgctt gcctctccaa t | 21 |

<210> SEQ ID NO 58
<211> LENGTH: 26
<212> TYPE: DNA
<213> ORGANISM: Artificial sequence
<220> FEATURE:
<223> OTHER INFORMATION: Probe

<400> SEQUENCE: 58

| | |
|---|---|
| ccattgagcc atggatactg gcagac | 26 |

<210> SEQ ID NO 59
<211> LENGTH: 433
<212> TYPE: DNA
<213> ORGANISM: Bulleidia species Type 1

<400> SEQUENCE: 59

| | |
|---|---|
| agcagtaggg aattttcggc aatgggcgaa agcctgaccg agcaacgccg cgtgagtgat | 60 |
| gacggccttc gggttgtaaa gctctgttgt aagaaaagat aaactagtag agaatattag | 120 |
| ttagacatta tcttaccaga aagccacggc taactacgtg ccagcagccg cggtaatacg | 180 |
| taggtggcga gcgttatccg gaattattgg gcgtaaaggg tgcgtaggcg gtctgttaag | 240 |
| ttcatggtta aattttgggg ctcaacccca ttgagccatg gatactggca gactagagta | 300 |
| ttggagaggc aagcggaatt ccatgtgtag cggtaaaatg cgtagatata tggaggaaca | 360 |
| ccggtggcga aggcggcttg ctagccaaag actgacgctc aggcacgaaa gcgtggggag | 420 |
| caaataggat tag | 433 |

<210> SEQ ID NO 60
<211> LENGTH: 21
<212> TYPE: DNA
<213> ORGANISM: Fusobacterium gonidiaformans

<400> SEQUENCE: 60

| | |
|---|---|
| ctcatagtct gggacaacat c | 21 |

<210> SEQ ID NO 61
<211> LENGTH: 23
<212> TYPE: DNA
<213> ORGANISM: Fusobacterium gonidiaformans

<400> SEQUENCE: 61

| | |
|---|---|
| atagctttca tacttcctcc atg | 23 |

<210> SEQ ID NO 62
<211> LENGTH: 23
<212> TYPE: DNA
<213> ORGANISM: Artificial sequence
<220> FEATURE:
<223> OTHER INFORMATION: Probe

<400> SEQUENCE: 62

```
gctaataccg gatattatgc ttt                                              23
```

<210> SEQ ID NO 63
<211> LENGTH: 1430
<212> TYPE: DNA
<213> ORGANISM: Fusobacterium gonidiaformans

<400> SEQUENCE: 63

```
gatgaacgct gacagaatgc ttaacacatg caagtcgact cgagtcttcg gacttgggtg      60
gcggacgggt gagtaacgcg taaagaactt gcctcatagt ctgggacaac atctggaaac     120
ggatgctaat accggatatt atgctttctt cgcatggagg aagtatgaaa gctatatgcg     180
ctatgagaga gctttgcgtc ccattagcta gttggtgagg taacggccca ccaaggcgat     240
gatgggtagc cggcctgaga gggtgaacgg ccacaagggg actgagacac ggcccttact     300
cctacgggag gcagcagtgg ggaatattgg acaatggacc aaaagtctga tccagcaatt     360
ctgtgtgcac gatgacgttt ttcggaatgt aaagtgcttt cagtcgggaa gaagcaagtg     420
acggtaccga cagaagaagc gacggctaaa tacgtgccag cagccgcggt aatacgtatg     480
tcgcaagcgt tatccggatt tattgggcgt aaagcgcgtc taggcggcaa ggaaagtctg     540
atgtgaaaat gcggggctca actccgtatt gcgttggaaa ctgccttact agagtactgg     600
agaggtaggc ggaactacaa gtgtagaggt gaaattcgta gatatttgta ggaatgccga     660
tggggaagcc agcctactgg acagatactg acgctaaagc gcgaaagcgt gggtagcaaa     720
caggattaga taccctggta gtccacgctg taaacgatga ttactaggtg ttgggggtca     780
aacctcagcg cccaagctaa cgcgataagt aatccgcctg ggagtacgt acgcaagtat     840
gaaactcaaa ggaattgacg ggacccgca caagcggtgg agcatgtggt ttaattcgac     900
gcaacgcgag gaaccttacc agcgtttgac atcctacaaa gagtgcagag atgcgcttgt     960
gcttcttcgg aagaatgtag tgacaggtgg tgcatggctg tcgtcagctc gtgtcgtgag    1020
atgttgggtt aagtcccgca acgagcgcaa cccctatcgt atgttaccag cctttagttg    1080
gggactcatg cgatactgcc tgcgacgagc aggaggaagg tggggatgac gtcaagtcat    1140
catgcccctt atacgctggg ctacacacgt gctacaatgg gtagtacaga gagcggcgaa    1200
cccgcgaggg ggagcaaatc tcagaaaact attcttagtt cggattgtac tctgcaactc    1260
gagtacatga gttggaatc gctagtaatc gcaaatcagc aatgttgcgg tgaatacgtt    1320
ctcgggtctt gtacacaccg cccgtcacac cacgagagtt ggttgcacct gaagtagcag    1380
gcctaaccgt aaggaaggat gctccgaggg tgtggttagc gattggggtg               1430
```

<210> SEQ ID NO 64
<211> LENGTH: 21
<212> TYPE: DNA
<213> ORGANISM: Fusobacterium equinum

<400> SEQUENCE: 64

```
ctcttagtct gggacaacat c                                                21
```

<210> SEQ ID NO 65
<211> LENGTH: 23
<212> TYPE: DNA
<213> ORGANISM: Fusobacterium equinum

<400> SEQUENCE: 65

```
gtagctttca tgctttctcc atg                                              23
```

<210> SEQ ID NO 66
<211> LENGTH: 23
<212> TYPE: DNA
<213> ORGANISM: Artificial sequence
<220> FEATURE:
<223> OTHER INFORMATION: Probe

<400> SEQUENCE: 66

```
gctaataccg gatattatgc ttt                                              23
```

<210> SEQ ID NO 67
<211> LENGTH: 1430
<212> TYPE: DNA
<213> ORGANISM: Fusobacterium equinum

<400> SEQUENCE: 67

```
gatgaacgct gacagaatgc ttaacacatg caagtcaact cgagtcttcg gacttgggtg      60
gcggacgggt gagtaacgcg taaagaactt gcctcttagt ctgggacaac atctggaaac     120
ggatgctaat accggatatt atgctttttt cgcatggaga aagcatgaaa gctacatgcg     180
ctaagagaga gctttgcgtc ccattagctc gttggtgagg taacggctca ccaaggcaat     240
gatgggtacc cggcctgaga gggtgaacgg ccacaagggg actgagacac ggcccttact     300
cctacgggag gcagcagtgg ggaatattgg acaatggacc aaaagtctga tccagcaatt     360
ctgtgtgcac gatgacgttt ttcggaatgt aaagtgcttt cagtcgggaa gaagaaagtg     420
acggtaccga cagaagaagc gacggctaaa tacgtgccag cagccgcggt aatacgtatg     480
tcgcaagcgt tatccggatt tattgggcgt aaagcgcgtc taggcggcaa ggaaagtctg     540
atgtgaaaat gcggggctca actccgtatt gcgttggaaa ctgccttact agagtactgg     600
agaggtaggc ggaactacaa gtgtagaggt gaaattcgta gatatttgta ggaatgccga     660
tggggaagcc agcctactgg acagatactg acgctaaagc gcgaaagcgt gggtagcaaa     720
caggattaga taccctggta gtccacgctg taaacgatga ttactaggtg ttggggtca     780
aacctcagcg cccaagctaa cgcgataagt aatccgcctg gggagtacgt acgcaagtat     840
gaaactcaaa ggaattgacg gggacccgca caagcggtgg agcatgtggt ttaattcgac     900
gcaacgcgag gaaccttacc agcgtttgac atcctacgaa cggtgcagag atgcgccggt     960
gcccccttcgg gggaacgtag tgacaggtgg tgcatggctg tcgtcagctc gtgtcgtgag    1020
atgttgggtt aagtcccgca acgagcgcaa cccctatcgt atgttaccag ccttcagttg    1080
gggactcatg cgatactgcc tgcgacgagc aggaggaagg tggggatgac gtcaagtcat    1140
catgcccctt atacgctggg ctacacacgt gctacaatgg gtagtacaga gagccgcaaa    1200
cccgcgaggg ggagcaaatc tcagaaaact attcttagtt cggattgtac tctgcaactc    1260
gagtacatga agttggaatc gctagtaatc gcaaatcagc aatgttgcgg tgaatacgtt    1320
ctcgggtctt gtacacaccg cccgtcacac cacgagagtg ggttgcacct gaagtagcag    1380
gcctaacctt agggaaggat gctccgaggg tgtggttcgc gattggggtg               1430
```

<210> SEQ ID NO 68
<211> LENGTH: 24
<212> TYPE: DNA
<213> ORGANISM: Megasphaera species Type 2

<400> SEQUENCE: 68

```
aaggtggtaa atagccatca tgag                                             24
```

<210> SEQ ID NO 69

```
<211> LENGTH: 21
<212> TYPE: DNA
<213> ORGANISM: Megasphaera species Type 2

<400> SEQUENCE: 69
ctctccgaca ctcaagtctt c                                              21

<210> SEQ ID NO 70
<211> LENGTH: 22
<212> TYPE: DNA
<213> ORGANISM: Artificial sequence
<220> FEATURE:
<223> OTHER INFORMATION: Probe

<400> SEQUENCE: 70
ccgtggcttt ctcttacggt ac                                             22

<210> SEQ ID NO 71
<211> LENGTH: 1449
<212> TYPE: DNA
<213> ORGANISM: Megasphaera species Type 2
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (1439)..(1439)
<223> OTHER INFORMATION: n is a, c, g, or t

<400> SEQUENCE: 71
cgagaggana tggaaagctt gctttctata aaatctagtg caaacgggt gagtaacgcg      60 taaacaacct gcccttcgga tggggacaac agctggaaac ggctgctaat accgaatacg    120
ttcttttcat cgcatggtga aagaagaaa ggacggcctc tacacaaagc ggtcgccgaa     180
ggaggggttt gcgtctgatt agctagttgg aggggtaacg cccaacaag gcgacgatca     240 gtagccggtc tgagaggatg aacgccaca ttgggactga gacacggccc agactcctac    300
gggaggcagc agtggggaat cttccgcaat ggacgaaagt ctgacggagc aacgccgcgt    360
gagtgaagac ggtcttcgga ttgtaaagct ctgttatacg ggacgaacgg caaggtggta    420
aatagccatc atgagtgacg gtaccgtaag agaaagccac ggctaactac gtgccagcag    480
ccgcggtaat acgtaggtgg caagcgttgt ccggaattat tgggcgtaaa gggcgcgcag    540
gcggtttttt aagtcggtct aaaagtgcg gggcttaacc ccgtgagggg accgaaactg     600
gaagacttga gtgtcggaga ggaaagcgga attcctagtg tagcggtgaa atgcgtagat    660
attaggagga acaccggtgg cgaaagcggc tttctggacg acaactgacg ctgaggcgcg    720
aaagcgtggg gagcaaacag gattagatac cctggtagtc cacgccgtaa acgatggata    780
ctaggtgtag gaggtatcga ctccttctgt gccgtagtta acgctataag tatcccgcct    840
ggggagtacg gccgcaaggt tgaaactcaa aggaattgac ggggcccgc acaagcggtg     900 gagtatgtgg tttaattcga cgcaacgcga agaaccttac caagccttga cattgatcgc    960
aattttcaga gatgagaagt tcctcttcgg aggacgagaa acaggtggt gcacggctgt    1020 cgtcagctcg tgtcgtgaga tgttgggtta agtcccgcaa cgagcgcaac ccctatcttc   1080
tgttaccagc acgtaaaggt ggggactcag gagagactgc cgcagacaat gcggaggaag   1140
gcggggatga cgtcaagtca tcatgccct tatggcttgg gctacacacg tactacaatg    1200
gctcttaata gagggaagcg aaggagtgat ctggagcaaa ccccaaaaac agagtctcag   1260
ttcggattgt aggctgcaac tcgcctacat gaagcaggaa tcgctagtaa tcgcaggtca   1320
```

```
gcatactgcg gtgaatacgt tcccgggcct tgtacacacc gcccgtcaca ccacgaaagt   1380
cattcacacc cgaagccggt gaggtaaccg caaggagcca gccgtcgaag gtaggggtna   1440
tgattgggg                                                           1449
```

<210> SEQ ID NO 72
<211> LENGTH: 23
<212> TYPE: DNA
<213> ORGANISM: Peptoniphilus lacrimalis

<400> SEQUENCE: 72

```
gcttgacata taagagacga act                                             23
```

<210> SEQ ID NO 73
<211> LENGTH: 22
<212> TYPE: DNA
<213> ORGANISM: Peptoniphilus lacrimalis

<400> SEQUENCE: 73

```
ccgaaatgct ggtaactagt aa                                              22
```

<210> SEQ ID NO 74
<211> LENGTH: 28
<212> TYPE: DNA
<213> ORGANISM: Artificial sequence
<220> FEATURE:
<223> OTHER INFORMATION: Probe

<400> SEQUENCE: 74

```
taagttttct tcttcggaag cccttata                                        28
```

<210> SEQ ID NO 75
<211> LENGTH: 1374
<212> TYPE: DNA
<213> ORGANISM: Peptoniphilus lacrimalis

<400> SEQUENCE: 75

```
gcagtcgagc gatgaatctt aacagaaccc ttcggggcga agataagatg gattagcggc     60
ggacgggtga gtaacacgtg agtaacctgc cttttacaca gggatagcct cgggaaaccg    120
ggattaaaac ctgatgaaac tatcaaatca catgattaag aaagttaaaa ctccggtggt    180
aaaagatgga ctcgcgtccc attagctagt tggtgaaggt aacggccac caaggcaacg    240 atgggtagcc ggcctgagag ggtgaacggc cacattggaa ctgagaaacg gtccaaactc    300
ctacgggagg cagcagtggg gaatattgca caatggggga acccctgatg cagcgacgcc    360
gcgtgagcga agaaggcctt cgggtcgtaa agctcttta tatgggaaga taatgacggt    420
accataagaa aaagccccgg ctaactacgt gccagcagcc gcggtaatac gtaggggct    480 agcgttgtcc ggaatcactg ggcgtaaagg gttcgcaggc ggcaatgcaa gtcagatgta    540
aaaggcaaag gctcaacctt tgtaagcatc tgaaactgta tagcttgaga agtgtagagg    600
caagtggaat ttttagtgta gcggtgaaat gcgtagatat aaaaagaat accggtggcg    660 aaggcgactt gctgggcaca atctgacgct gaggaacgaa agcgtgggga gcaaacagga    720
ttagataccc tggtagtcca cgccgtaaac gatgagtgct aggtgtcggt ataaatcggt    780
gccgcagtta acacaataag cactccgcct ggggagtacg tgcgcaagca tgaaactcaa    840
aggaattgac ggggacccgc acaagcagcg gagcatgtgg tttaattcga agcaacgcga    900
agaaccttac cagggcttga catataagag acgaacttag agataagttt tcttcttcgg    960
```

```
aagcccttat acaggtggtg catggttgtc gtcagctcgt gtcgtgagat gttgggttaa    1020
gtcccgcaac gagcgcaacc cttattacta gttaccagca tttcggatgg ggactctaga    1080
aagactgccg atgataaatc ggaggaaggt ggggatgacg tcaaatcatc atgccctata    1140
tgccctgggc aacacacgtg ctacaatggc cgtaacaaag agaagcgaaa tcgcaaggtc    1200
aagcaaacct caaaaagacg gtctcagttc ggattgttct ctgcaactcg agaacatgaa    1260
gtcggagttg ctagtaatcg cagatcagaa tgctgcggtg aatgcgttcc cgggtcttgt    1320
acacaccgcc cgtcacacca tgggagcttg taatacccga agccttgagc taac           1374
```

<210> SEQ ID NO 76
<211> LENGTH: 20
<212> TYPE: DNA
<213> ORGANISM: Bacteroidales species Type 1

<400> SEQUENCE: 76

```
tgtaccaagt cagcggtgaa                                                  20
```

<210> SEQ ID NO 77
<211> LENGTH: 20
<212> TYPE: DNA
<213> ORGANISM: Bacteroidales species Type 1

<400> SEQUENCE: 77

```
cggctcccgt attctagcat                                                  20
```

<210> SEQ ID NO 78
<211> LENGTH: 21
<212> TYPE: DNA
<213> ORGANISM: Artificial sequence
<220> FEATURE:
<223> OTHER INFORMATION: Probe

<400> SEQUENCE: 78

```
aacgcaggct gtgccgttga a                                                21
```

<210> SEQ ID NO 79
<211> LENGTH: 434
<212> TYPE: DNA
<213> ORGANISM: Bacteroidales species Type 1

<400> SEQUENCE: 79

```
agcagtgagg aatattggac aatgggcgga agcctgatcc agccatgccg cgtgaaggaa     60
ggaggtccta tggatcgtaa acttcttttg acgcagagca ataaagtgta cgagtacact    120
gatgagagta tgcgtcgaat aagcatcggc taactccgtg ccagcagccg cggtaatacg    180
gaggatgcga gcgttatccg gatttattgg gtttaaaggg tgcgtaggct gtgtaccaag    240
tcagcggtga atacctgtg cttaacgcag gctgtgccgt tgaaactggc atgctagaat    300 acggagccg tgggaggaat gtgtggtgta gcggtgaaat gcatagatat cacacagaac    360
accgattgcg aaggcatctc acgattccgt aattgacgct taggcacgaa agcgtgggta    420
tcgaacagga ttag                                                       434
```

<210> SEQ ID NO 80
<211> LENGTH: 21
<212> TYPE: DNA
<213> ORGANISM: Vaginal TM7 species Type 1

<400> SEQUENCE: 80

```
tgacatccct agaatttctc c                                                21
```

<210> SEQ ID NO 81
<211> LENGTH: 19
<212> TYPE: DNA
<213> ORGANISM: Vaginal TM7 species Type 1

<400> SEQUENCE: 81
ggatctgtca cctagttct                                                    19

<210> SEQ ID NO 82
<211> LENGTH: 19
<212> TYPE: DNA
<213> ORGANISM: Artificial sequence
<220> FEATURE:
<223> OTHER INFORMATION: Probe

<400> SEQUENCE: 82
aaggagagag tgcttttta                                                    19

<210> SEQ ID NO 83
<211> LENGTH: 997
<212> TYPE: DNA
<213> ORGANISM: Vaginal TM7 species Type 1

<400> SEQUENCE: 83
tgaggaatat tccacaatgg gcgaaagcct gatggagcaa tgccgcgtgc aggatgaagg        60
ccctcgggtc gtaaactgct tttattagag aagaatatga cggtaactaa tgaataaggg      120
acggctaact acgtgccagc agccgcggtc atacgtaggt cccaagcgtt atccggagtg      180
actgggcgta aagagttgcg taggcggcta agtaagcgag taatgaaaac tatcggctca      240
accggtagcc tgttattcga actgcttggc tcgagattat cagaggtcgc tggaattcct      300
agtgtagcag tgaaatgcgt agatattagg aagaacacca atggcgtagg caggcgactg      360
gggtatttct gacgctaagg cacgaaagcg tggggagcga accggattag atacccgggt      420
agtccacgcc gtaaacgatg gatgctaatt gttcggggta tcgacccctt gagtaataaa      480
gctaacgcgt taagcatccc gcctgtggag tacggccgca aggctaaaac ataaaggaat      540
tgacggggac ccgcacaagc ggtggaggat gttctttaat tcgatgataa gcaagaacc       600 ttaccagggc ttgacatccc tagaatttct ccgaaaggag agagtgcttt ttaagaacta      660
ggtgacagat cctgcatggc cgtcgtcagc tcgtgtcgtg agatgtttgg ttaagtccat      720
caacgagcgc aaccccttatc gttagttgta tttttctaac gagactgccc cggtaacggg      780
gaggaaggag gggatgatgt caggtcagta ttggtcttac gtcctgggct agaaacgtcc      840
tacaatggct agtacaatgg cagcgaatc cgcgaggtga agcaaatccc atcaaagcta       900
gtcccagttc ggattgcagg ctgaaactcg cctgcatgaa gtcggaatcg ctagtaatcg      960
cagatcagca cgctgtcggt gaatacgttc ccgggtc                              997

<210> SEQ ID NO 84
<211> LENGTH: 21
<212> TYPE: DNA
<213> ORGANISM: Megasphaera Type 1

<400> SEQUENCE: 84
gatgccaaca gtatccgtcc g                                                 21

<210> SEQ ID NO 85
<211> LENGTH: 22
<212> TYPE: DNA

```
<213> ORGANISM: Megasphaera Type 1

<400> SEQUENCE: 85
cctctccgac actcaagttc ga                                              22

<210> SEQ ID NO 86
<211> LENGTH: 24
<212> TYPE: DNA
<213> ORGANISM: Megasphaera Type 2

<400> SEQUENCE: 86
aaggtggtaa atagccatca tgag                                            24

<210> SEQ ID NO 87
<211> LENGTH: 21
<212> TYPE: DNA
<213> ORGANISM: Megasphaera Type  2

<400> SEQUENCE: 87
ctctccgaca ctcaagtctt c                                               21

<210> SEQ ID NO 88
<211> LENGTH: 22
<212> TYPE: DNA
<213> ORGANISM: Artificial sequence
<220> FEATURE:
<223> OTHER INFORMATION: Probe

<400> SEQUENCE: 88
ccgtggcttt ctcttacggt ac                                              22

<210> SEQ ID NO 89
<211> LENGTH: 24
<212> TYPE: DNA
<213> ORGANISM: Prevotella amnii

<400> SEQUENCE: 89
ggcttgaatt gcagatgttt atat                                            24

<210> SEQ ID NO 90
<211> LENGTH: 21
<212> TYPE: DNA
<213> ORGANISM: Prevotella amnii

<400> SEQUENCE: 90
ccatgcagca ccttcacaaa t                                               21

<210> SEQ ID NO 91
<211> LENGTH: 20
<212> TYPE: DNA
<213> ORGANISM: Artificial sequence
<220> FEATURE:
<223> OTHER INFORMATION: Probe

<400> SEQUENCE: 91
agatgatata ttcccttcgg                                                 20

<210> SEQ ID NO 92
<211> LENGTH: 25
<212> TYPE: DNA
<213> ORGANISM: Parvimonas sp Type 1

<400> SEQUENCE: 92
aacgtgattt ttatggaata gcctt                                           25
```

<210> SEQ ID NO 93
<211> LENGTH: 23
<212> TYPE: DNA
<213> ORGANISM: Parvimonas sp Type 1

<400> SEQUENCE: 93
ggtattaatc gtcgtttcca acg                                    23

<210> SEQ ID NO 94
<211> LENGTH: 29
<212> TYPE: DNA
<213> ORGANISM: Artificial sequence
<220> FEATURE:
<223> OTHER INFORMATION: Probe

<400> SEQUENCE: 94
ataggaaata gaatgaaagt ggcgaacgg                              29

<210> SEQ ID NO 95
<211> LENGTH: 22
<212> TYPE: DNA
<213> ORGANISM: Lactobacillus vaginalis

<400> SEQUENCE: 95
cactggccca actgatatga cg                                     22

<210> SEQ ID NO 96
<211> LENGTH: 21
<212> TYPE: DNA
<213> ORGANISM: Lactobacillus vaginalis

<400> SEQUENCE: 96
cagatgttat cccccgcttc a                                      21

<210> SEQ ID NO 97
<211> LENGTH: 24
<212> TYPE: DNA
<213> ORGANISM: Artificial sequence
<220> FEATURE:
<223> OTHER INFORMATION: Probe

<400> SEQUENCE: 97
tgaattgacg ttggattmcc agtg                                   24

<210> SEQ ID NO 98
<211> LENGTH: 24
<212> TYPE: DNA
<213> ORGANISM: Prevotella bivia

<400> SEQUENCE: 98
gcttgaattg cagatgaacg attt                                   24

<210> SEQ ID NO 99
<211> LENGTH: 24
<212> TYPE: DNA
<213> ORGANISM: Prevotella bivia

<400> SEQUENCE: 99
agcagaacct gatggcaact aaag                                   24

<210> SEQ ID NO 100
<211> LENGTH: 28
<212> TYPE: DNA

```
<213> ORGANISM: Artificial sequence
<220> FEATURE:
<223> OTHER INFORMATION: Probe

<400> SEQUENCE: 100
taatgaggtc cttcgggaca tctgtgaa                                      28

<210> SEQ ID NO 101
<211> LENGTH: 23
<212> TYPE: DNA
<213> ORGANISM: Vaginal Peptostreptococcus sp

<400> SEQUENCE: 101
cgtgaacgat gaaggtcttc gga                                           23

<210> SEQ ID NO 102
<211> LENGTH: 22
<212> TYPE: DNA
<213> ORGANISM: Vaginal Peptostreptococcus sp

<400> SEQUENCE: 102
ttagccgggg cttcctcaca gg                                            22

<210> SEQ ID NO 103
<211> LENGTH: 20
<212> TYPE: DNA
<213> ORGANISM: Artificial sequence
<220> FEATURE:
<223> OTHER INFORMATION: Probe

<400> SEQUENCE: 103
gttctgttgc aggggaagat                                               20
```